US012806205B2

(12) United States Patent
Foegh et al.

(10) Patent No.: US 12,806,205 B2
(45) Date of Patent: Nov. 24, 2026

(54) METHODS FOR TREATING CANCER

(71) Applicant: Allarity Therapeutics, Inc., Boston, MA (US)

(72) Inventors: Marie Foegh, New York, NY (US); Steen Knudsen, Melby (DK)

(73) Assignee: Allarity Therapeutics, Inc., Boston, MA (US)

( * ) Notice: Subject to any disclaimer, the term of this patent is extended or adjusted under 35 U.S.C. 154(b) by 320 days.

(21) Appl. No.: 18/606,590

(22) Filed: Mar. 15, 2024

(65) Prior Publication Data

US 2024/0325396 A1 Oct. 3, 2024

Related U.S. Application Data

(60) Provisional application No. 63/602,480, filed on Nov. 24, 2023, provisional application No. 63/452,795, filed on Mar. 17, 2023.

(51) Int. Cl.

| | |
|---|---|
| ***A61K 31/519*** | (2006.01) |
| ***A61K 9/28*** | (2006.01) |
| ***A61K 9/48*** | (2006.01) |
| ***A61K 31/496*** | (2006.01) |
| ***A61P 35/00*** | (2006.01) |

(52) U.S. Cl.

CPC .............. *A61K 31/519* (2013.01); *A61K 9/28* (2013.01); *A61K 9/4825* (2013.01); *A61K 31/496* (2013.01); *A61P 35/00* (2018.01)

(58) Field of Classification Search

CPC .................................................... A61K 31/519

See application file for complete search history.

(56) References Cited

U.S. PATENT DOCUMENTS

| | | | |
|---|---|---|---|
| 6,911,306 | B1 | 6/2005 | Vertino |
| 7,239,986 | B2 | 7/2007 | Golub et al. |
| 7,268,138 | B2 | 9/2007 | Kalish et al. |
| 7,709,616 | B2 | 5/2010 | Bentwich et al. |
| 8,236,802 | B2 | 8/2012 | Xu et al. |
| 8,445,198 | B2 | 5/2013 | Knudsen |
| 8,894,989 | B2 | 11/2014 | Xu et al. |
| 9,598,734 | B2 | 3/2017 | Knudsen |
| 9,725,769 | B1 | 8/2017 | Knudsen |
| 2001/0051344 | A1 | 12/2001 | Shalon et al. |
| 2002/0164663 | A1 | 11/2002 | Fuqua et al. |
| 2003/0073083 | A1 | 4/2003 | Tamayo et al. |
| 2004/0018525 | A1 | 1/2004 | Wirtz et al. |
| 2004/0072722 | A1 | 4/2004 | Kornblith et al. |
| 2005/0176669 | A1 | 8/2005 | Al-Murrani |
| 2005/0260586 | A1 | 11/2005 | Demuth et al. |
| 2005/0260646 | A1 | 11/2005 | Baker et al. |
| 2006/0105360 | A1 | 5/2006 | Croce et al. |
| 2006/0121511 | A1 | 6/2006 | Lee et al. |
| 2006/0142231 | A1 | 6/2006 | Ashworth et al. |
| 2007/0059720 | A9 | 3/2007 | Fuqua et al. |
| 2007/0172844 | A1 | 7/2007 | Lancaster et al. |
| 2008/0227663 | A1 | 9/2008 | Tisone et al. |
| 2008/0306006 | A1 | 12/2008 | Croce et al. |
| 2009/0023149 | A1 | 1/2009 | Knudsen |
| 2009/0221435 | A1 | 9/2009 | Baskerville et al. |
| 2009/0239223 | A1 | 9/2009 | Gehrmann et al. |
| 2010/0240043 | A1 | 9/2010 | Rotter et al. |
| 2011/0123990 | A1 | 5/2011 | Baker et al. |
| 2012/0046186 | A1 | 2/2012 | Pelham et al. |
| 2012/0177726 | A1 | 7/2012 | Petersen et al. |
| 2012/0214703 | A1 | 8/2012 | Croce et al. |
| 2012/0302626 | A1 | 11/2012 | Dave et al. |
| 2013/0053275 | A1 | 2/2013 | Knudsen |
| 2013/0059015 | A1 | 3/2013 | Lancaster et al. |
| 2014/0294730 | A1 | 10/2014 | Slack-Davis et al. |
| 2015/0141429 | A1 | 5/2015 | Xu et al. |
| 2015/0353928 | A1 | 12/2015 | Weiner |
| 2016/0199399 | A1 | 7/2016 | Knudsen |
| 2017/0100368 | A1 | 4/2017 | Cox et al. |
| 2017/0283884 | A1 | 10/2017 | Knudsen |
| 2018/0087113 | A1 | 3/2018 | Knudsen |
| 2018/0202004 | A1 | 7/2018 | Knudsen |

FOREIGN PATENT DOCUMENTS

| | | | |
|---|---|---|---|
| CA | 2428112 | A1 | 11/2003 |
| CN | 102002490 | A | 4/2011 |
| EP | 1550731 | A1 | 7/2005 |
| EP | 2081950 | B1 | 3/2013 |
| JP | 2001-17171 | A | 1/2001 |
| JP | 2002-531066 | A | 9/2002 |
| JP | 2004-43446 | A | 2/2004 |
| JP | 2005-530784 | A | 10/2005 |
| JP | 2009-513161 | A | 4/2009 |
| RU | 2528247 | C2 | 9/2014 |
| WO | WO-00/31930 | A1 | 6/2000 |

(Continued)

OTHER PUBLICATIONS

Wang et al., "Progress in the research of PARP inhibitors and their mechanisms of action," Chinese Journal of New Drugs. 27(3):306-313 (Feb. 2018).

"Oncology Venture presents LiPlaCis on AACR in New Orleans," Press release issued by Oncology Venture Sweden AB, Hoersholm, Denmark, Mar. 4, 2016 (2 pages).

Abba et al., "Gene expression signature of estrogen receptor alpha status in breast cancer," BMC Genomics. 6:37 (2005) (13 pages).

Affymetrix Expression Probeset Details for HG-U133_PLUS_2:209083_AT, <https://www.affymetrix.com/analysis/netaffx/fullrecord.affx?pk=HG-U133_PLUS_2:209083_AT>, retrieved Nov. 27, 2018 (4 pages).

Agrawal et al., "Long-term effect of fulvestrant on hormone receptors and proliferation marker in breast cancer," EJC Supplements. 8(3):111 (2010).

(Continued)

*Primary Examiner* — John S Kenyon

(74) *Attorney, Agent, or Firm* — Clark & Elbing LLP

(57) ABSTRACT

Described are methods of treating cancer (e.g., solid tumor cancer) using stenoparib monotherapy at BID dosing or a combination therapy including stenoparib (at BID dosing) and dovitinib (at QD dosing).

36 Claims, 8 Drawing Sheets

Specification includes a Sequence Listing.

(56) References Cited

FOREIGN PATENT DOCUMENTS

| | | | |
|---|---|---|---|
| WO | WO-00/35473 A2 | 6/2000 | |
| WO | WO-03/082078 A2 | 10/2003 | |
| WO | WO-2005/005601 A2 | 1/2005 | |
| WO | WO-2005/014856 A1 | 2/2005 | |
| WO | WO-2005/047534 A2 | 5/2005 | |
| WO | WO-2005/066371 A2 | 7/2005 | |
| WO | WO-2005/087948 A2 | 9/2005 | |
| WO | WO-2005/094863 A1 | 10/2005 | |
| WO | WO-2005/100606 A2 | 10/2005 | |
| WO | WO-2006078711 A2 | 7/2006 | |
| WO | WO-2007/053648 A2 | 5/2007 | |
| WO | WO-2007/072225 A2 | 6/2007 | |
| WO | WO-2008/073177 A2 | 6/2008 | |
| WO | WO-2008/073629 A2 | 6/2008 | |
| WO | WO-2008/112283 A2 | 9/2008 | |
| WO | WO-2008/138578 A2 | 11/2008 | |
| WO | WO-2009/036332 A1 | 3/2009 | |
| WO | WO-2009/046205 A1 | 4/2009 | |
| WO | WO-2009/080437 A1 | 7/2009 | |
| WO | WO-2009/100159 A2 | 8/2009 | |
| WO | WO-2009/141450 A2 | 11/2009 | |
| WO | WO-2011/032563 A1 | 3/2011 | |
| WO | WO-2011/047689 A2 | 4/2011 | |
| WO | WO-2011/058367 A2 | 5/2011 | |
| WO | WO-2011/098578 A2 | 8/2011 | |
| WO | WO-2011/135459 A2 | 11/2011 | |
| WO | WO-2012/024543 A1 | 2/2012 | |
| WO | WO-2012/106718 A2 | 8/2012 | |
| WO | WO-2012/109233 A2 | 8/2012 | |
| WO | WO-2012/163541 A1 | 12/2012 | |
| WO | WO-2013/130465 A2 | 9/2013 | |
| WO | WO-2013/133876 A1 | 9/2013 | |
| WO | WO-2014/195032 A1 | 12/2014 | |
| WO | WO-2014/205105 A1 | 12/2014 | |
| WO | WO-2015/135035 A2 | 9/2015 | |
| WO | WO-2015/184145 A1 | 12/2015 | |
| WO | WO-2019219759 A1 * | 11/2019 | ........... C12Q 1/6886 |

OTHER PUBLICATIONS

Arienti et al., "Activity of lipoplatin in tumor and in normal cells in vitro," Anti-Cancer Drugs. 19(10):983-990 (2008) (8 pages).
Baker, "The central role of receiver operating characteristic (ROC) curves in evaluating tests for the early detection of cancer," J Natl Cancer Inst. 95(7):511-5 (2003).
Bild et al., "Oncogenic pathway signatures in human cancers as a guide to targeted therapies," Nature. 439(7074):353-7 (2006).
Boulikas, "Clinical overview on Lipoplatin™: a successful liposomal formulation of cisplatin," Expert Opin Investig Drugs. 18(8):1197-218 (2009) (23 pages).
Buhl et al., "A genetic response profile to predict efficacy of adjuvant 5-FU in colon cancer," Ann Oncol. 25(Suppl. 4):iv167-209 (2014) (1 page).
Casagrande et al., "Preclinical Activity of the Liposomal Cisplatin Lipoplatin in Ovarian Cancer," Clin Cancer Res. 20(21):5496-5506 (12 pages).
Castelli et al., "In silico analysis of microRNAS targeting the HLA-G 3' untranslated region alleles and haplotypes," Hum Immunol. 70(12):1020-5 (2009).
Chow et al., "Increased expression of annexin I is associated with drug-resistance in nasopharyngeal carcinoma and other solid tumors," Proteomics Clin Appl. 3(6):654-62 (2009).
Dahlén et al., "Activation of the GLI oncogene through fusion with the beta-actin gene (ACTB) in a group of distinctive pericytic neoplasms: pericytoma with t(7;12)," Am J Pathol. 164(5):1645-53 (2004).
De Jonge et al., "Early cessation of the clinical development of LiPlaCis, a liposomal cisplatin formulation," Eur J Cancer. 46(16):3016-3021 (2010) (6 pages).
Di Lisio, "MicroRNA expression in B-cell lymphomas," Doctoral Thesis, Facultad de Ciencias, Departamento de Biología Molecular, Universidad Autónoma de Madrid (2012) (223 pages).
Elstrom et al., "Response to second-line therapy defines the potential for cure in patients with recurrent diffuse large B-cell lymphoma: implications for the development of novel therapeutic strategies," Clin Lymphoma Myeloma Leuk. 10(3):192-6 (2010).
Etter et al., "The combination of chemotherapy and intraperitoneal MegaFas Ligand improves treatment of ovarian carcinoma," Gynecol Oncol. 107(1):14-21 (2007).
Fournier et al., "Gene expression signature in organized and growth-arrested mammary acini predicts good outcome in breast cancer," Cancer Res. 66(14):7095-7102 (2006).
Friis-Hansen et al., "Mir-449 inhibits growth of gastric cancer cells partly by inhibiting the expression of met and amphiregulin," Gastroenterology. 136(5):A-165 (2009) (1 page).
Fumagalli et al., "Oral vinorelbine and capecitabine plus bevacizumab in recurrent inflammatory breast cancer: gene profiling and response to treatment," Thirty-Third Annual CTRC-AACR San Antonio Breast Cancer Symposium, Dec. 8-12, San Antonio, TX. Cancer Res. 70(24 Suppl.): Abstract P6-12-06 (2010) (4 pages).
Gallardo et al., "miR-34a as a prognostic marker of relapse in surgically resected non-small-cell lung cancer," Carcinogenesis. 30(11):1903-9 (2009).
Genbank Accession No. AY889152.1. Retrieved on Mar. 5, 2013 (2 pages).
Gerspach et al., "Therapeutic Targeting of CD95 and the TRAIL Death Receptors," Recent Pat Anticancer Drug Discov. 6(3):294-310 (2011).
Grimm et al., "Drugs interfering with apoptosis in breast cancer," Curr Pharm Des. 17(3):272-83 (2011).
Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).
Kinoshita et al. Inhibitor-induced structural change of the active site of human poly(ADP-ribose) polymerase. FEBS Letters,556(1-3):43-46, (2004) (16 pages).
Knudsen et al., "A novel drug specific mRNA biomarker predictor for selection of patients responding to dovitinib treatment of advanced renal cell carcinoma and other solid tumors," Plos One. 18(8):e0290681 (Aug. 2023) (16 pages).
Knudsen et al., "Development and validation of a gene expression score that predicts response to fulvestrant in breast cancer patients," PLoS One. 9(2):e87415 (2014) (12 pages).
Koeppel et al., "Irofulven cytotoxicity depends on transcription-coupled nucleotide excision repair and is correlated with XPG expression in solid tumor cells," Clin Cancer Res. 10(16):5604-13 (2004) (11 pages).
Kornmann et al., "Thymidylate synthase and dihydropyrimidine dehydrogenase mRNA expression levels: predictors for survival in colorectal cancer patients receiving adjuvant 5-fluorouracil," Clinical Cancer Res. 9(11):4116-24 (2003).
Kuter et al., "Dose-dependent change in biomarkers during neoadjuvant endocrine therapy with fulvestrant: results from Newest, a randomized Phase II study," Breast Cancer Res Treat. 133(1):237-46 (2012).
Lee et al., "Cancer pharmacogenomics: powerful tools in cancer chemotherapy and drug development," Oncologist. 10(2):104-11 (2005) (9 pages).
Li et al., "Intronic microRNA: discovery and biological implications," DNA Cell Biol. 26(4):195-207 (2007).
Li et al., "Selection of optimal oligonucleotide probes for microarrays using multiple criteria, global alignment and parameter estimation," Nucleic Acids Res. 33(19):6114-23 (2005).
Liang et al., "Caspase-mediated apoptosis and caspase-independent cell death induced by irofulven in prostate cancer cells," Mol Cancer Ther. 3(11):1385-96 (2004) (13 pages).
Liang et al., "Characterization of microRNA expression profiles in normal human tissues," BMC Genomics. 8(166): (2007) (20 pages).
Liu et al., "Roles of USF, Ikaros and Sp proteins in the transcriptional regulation of the human reduced folate carrier B promoter," Biochem J. 383(Pt 2):249-57 (2004).
López et al., Chapter 11: MicroRNAs in Lymphoma, *MicroRNAs in Cancer Translational Research*. W.C.S. Cho (ed.), 239-67 (2011).

(56) References Cited

OTHER PUBLICATIONS

McCune et al., "Prognosis of hormone-dependent breast cancers: implications of the presence of dysfunctional transcriptional networks activated by insulin via the immune transcription factor T-bet," Cancer Res. 70(2):685-96 (2010).
McGonigle et al., "E7449: A dual inhibitor of PARP1/2 and tankyrase 1/2 inhibits growth of DNA repair deficient tumors and antagonizes Wnt signaling," Oncotarget. 6(38):41307-23 (Dec. 2015).
Medinger et al., "Gene-expression Profiling in Patients with Plasma Cell Myeloma Treated with Novel Agents," Cancer Genomics Proteomics. 13(4):275-9 (2016).
Michels, "The promises and challenges of epigenetic epidemiology," Exp Gerontol. 45(4):297-301 (2010).
Michiels et al., "Prediction of cancer outcome with microarrays: a multiple random validation strategy," Lancet. 365(9458):488-92 (Feb. 2005).
Mizutani et al., "Significance of orotate phosphoribosyltransferase activity in renal cell carcinoma," J Urol. 171(2 Pt 1):605-10 (2004).
Nair et al., "A simple practice guide for dose conversion between animals and human," J Basic Clin Pharm. 7(2):27-31 (2016).
Nakamura et al., "Search of a group of genes involved with sensitivity to anticancer agent Cisplatin (CDDP) using cDNA microarray," Chiba Med J. 80(2):88 (2004) (2 pages).
Narita et al., "Lower expression of activating transcription factors 3 and 4 correlates with shorter progression-free survival in multiple myeloma patients receiving bortezomib plus dexamethasone therapy," Blood Cancer J. 5:e373 (2015) (8 pages).
NCode™ Multi-Species miRNA Microarray Probe Set, Version 2.0 (Cat. # MIRMPS2-01 ), retrieved from <http://www.invitrogen.com/site/us/en/home/Products-and-Services/Applications/epigenetics-noncoding-rna-research/miRNA-Profiling-/miRNA-Probe-Set-Files.html> (2009) (21 pages).
Nielsen et al., "Design of oligonucleotides for microarrays and perspectives for design of multi-transcriptome arrays," Nucleic Acids Res. 31(13):3491-6 (2003).
NIH DailyMed for Fluorouracil Injection, USP, revised May 2010, retrieved Jan. 29, 2019 (2010) (8 pages).
Nikas et al., "Prognosis of treatment response (pathological complete response) in breast cancer," Biomark Insights. 7:59-70 (2012).
Ocio et al., "The Activation of Fas Receptor by APO010, a Recombinant Form of Fas Ligand, Induces In Vitro and In Vivo Antimyeloma Activity," Blood. 110(11):1515 (2007) (4 pages) (Abstract Only).
Okumura et al., "Correlation between chemosensitivity and mRNA expression level of 5-fluorouracil-related metabolic enzymes during liver metastasis of colorectal cancer," Oncol Rep. 15(4):875-82 (2006).
Ooyama et al., "Gene expression analysis using human cancer xenografts to identify novel predictive marker genes for the efficacy of 5-fluorouracil-based drugs," Cancer Sci. 97(6):510-22 (2006).
Oplustilova et al., "Evaluation of candidate biomarkers to predict cancer cell sensitivity or resistance to PARP-1 inhibitor treatment", Cell Cycle 11(20):3837-50 (2012).
Paul et al., "Impact of miRNA deregulation on mRNA expression profiles in response to environmental toxicant, nonylphenol," Mol Cell Toxicol. 7:259-69 (2011).
Plummer et al., "First-in-human study of the PARP/tankyrase inhibitor E7449 in patients with advanced solid tumours and evaluation of a novel drug-response predictor," Br J Cancer. 123(4):525-533 (2020) (9 pages).
Pourhassan et al., "Revisiting the use of sPLA2-sensitive liposomes in cancer therapy," J Control Release. 261:163-173 (2017).
Pradervand et al., "Concordance among digital gene expression, microarrays, and qPCR when measuring differential expression of microRNAs," Biotechniques. 48(3):219-222 (2010).
Reid et al., "Circulating microRNAs: Association with disease and potential use as biomarkers," Crit Rev Oncol Hematol. 80(2):193-208 (2011).
Rouillard et al., "OligoArray 2.0: design of oligonucleotide probes for DNA microarrays using a thermodynamic approach," Nucleic Acids Res. 31(12):3057-62 (2003).
Senzer et al., "Irofulven demonstrates clinical activity against metastatic hormone-refractory prostate cancer in a phase 2 single-agent trial," Am J Clin Oncol. 28(1):36-42 (2005).
Sezaki et al., "Over-expression of the dominant-negative isoform of Ikaros confers resistance to dexamethasone-induced and anti-IgM-induced apoptosis," Br J Haematol. 121(1):165-9 (2003) (Abstract only).
Simon, "Roadmap for developing and validating therapeutically relevant genomic classifiers," J Clin Oncol. 23(29):7332-41 (Oct. 2005).
Slonim, "From patterns to pathways: gene expression data analysis comes of age," Nat Genet. 32 Suppl:502-8 (2002).
Suresh et al., "Resistance/response molecular signature for oral tongue squamous cell carcinoma," Dis Markers. 32(1):51-64 (2012).
The Japanese Journal of Urology, 94(2):159 (APP-105) (2003).
Van't Veer et al., "Gene expression profiling predicts clinical outcome of breast cancer," Nature. 415(6871):530-6 (2002).
Vangsted et al., "APO010 sensitivity in relapsed multiple myeloma patients," Annals of Oncol. 27(Supplement 6): vi15-vi42 (2016) (2 pages) (Abstract only).
Verbrugge et al., "Combining radiotherapy with APO010 in cancer treatment," Clin Cancer Res. 15(6):2031-8 (2009) (9 pages).
Wang et al., "Independent Validation of a Model Using Cell Line Chemosensitivity to Predict Response to Therapy," J Natl Cancer Inst. 105(17): 1284-91 (2013).
Woynarowska et al., "Changes in prostate-specific antigen (PSA) level correlate with growth inhibition of prostate cancer cells treated in vitro with a novel anticancer drug, irofulven," Invest New Drugs. 19(4):283-91 (2001).
Xu et al., "[Association of miRNAs expression profiles with prognosis and relapse in childhood acute lymphoblastic leukemia]," Zhonghua Xue Ye Xue Za Zhi. 32(3):178-81 (Abstract only) (2011).
Yang et al., "The role of microRNA in human lung squamous cell carcinoma," Cancer Genet Cytogenet. 200(2):127-33 (2010).
Yin, "Screening of laryngeal carcinoma multidrug resistance-associated genes and study on reversion by Chinese herbs," China Doctoral Dissertations Full-text Database, Division of Medical and Hygiene Technology. 8:E072-85 (2010) (3 pages) (Abstract only).
Zhang et al., "MicroRNA-650 targets ING4 to promote gastric cancer tumorigenicity," Biochem Biophys Res Commun. 395(2):275-280 (2010).

* cited by examiner

Note: A standard "3 +3" dose escalation design starting at dose 𝒦. The maximum tolerated dose (MTD) is the highest dose at which 0 or 1 dose-limiting toxicities (DLTs) are observed in six subjects. If de-escalation occurs at the first dose level, the study is discontinued.

SEQUENCE LISTING

```
Sequence total quantity: 472
SEQ ID NO: 1           moltype = DNA  length = 25
FEATURE                Location/Qualifiers
source                 1..25
                       mol_type = other DNA
                       organism = synthetic construct
SEQUENCE: 1
gatcaagatc tatctctctt cgtag                                        25

SEQ ID NO: 2           moltype = DNA  length = 25
FEATURE                Location/Qualifiers
source                 1..25
                       mol_type = other DNA
                       organism = synthetic construct
SEQUENCE: 2
gagggacttt gctgatttcc cctct                                        25

SEQ ID NO: 3           moltype = DNA  length = 25
FEATURE                Location/Qualifiers
source                 1..25
                       mol_type = other DNA
                       organism = synthetic construct
SEQUENCE: 3
tcagtgggca cagttcttca gctac                                        25

SEQ ID NO: 4           moltype = DNA  length = 25
```

-continued

```
FEATURE                Location/Qualifiers
source                 1..25
                       mol_type = other DNA
                       organism = synthetic construct
SEQUENCE: 4
cctggagcaa tgcactgtac ctgcc                                        25

SEQ ID NO: 5           moltype = DNA  length = 25
FEATURE                Location/Qualifiers
source                 1..25
                       mol_type = other DNA
                       organism = synthetic construct
SEQUENCE: 5
gtctgtgtct gacaatcgtc acgca                                        25

SEQ ID NO: 6           moltype = DNA  length = 25
FEATURE                Location/Qualifiers
source                 1..25
                       mol_type = other DNA
                       organism = synthetic construct
SEQUENCE: 6
tccccgtaca cgcactggaa gcaga                                        25

SEQ ID NO: 7           moltype = DNA  length = 25
FEATURE                Location/Qualifiers
source                 1..25
                       mol_type = other DNA
                       organism = synthetic construct
SEQUENCE: 7
ttgaagatcc ccgagatgca gctga                                        25

SEQ ID NO: 8           moltype = DNA  length = 25
FEATURE                Location/Qualifiers
source                 1..25
                       mol_type = other DNA
                       organism = synthetic construct
SEQUENCE: 8
gcgtttctgg cgatgcagca attcc                                        25

SEQ ID NO: 9           moltype = DNA  length = 25
FEATURE                Location/Qualifiers
source                 1..25
                       mol_type = other DNA
                       organism = synthetic construct
SEQUENCE: 9
aaccatgcct actaaatgta cagat                                        25

SEQ ID NO: 10          moltype = DNA  length = 25
FEATURE                Location/Qualifiers
source                 1..25
                       mol_type = other DNA
                       organism = synthetic construct
SEQUENCE: 10
agatcattaa aatccgtgcc cagac                                        25

SEQ ID NO: 11          moltype = DNA  length = 25
FEATURE                Location/Qualifiers
source                 1..25
                       mol_type = other DNA
                       organism = synthetic construct
SEQUENCE: 11
ttactcaagt tcaaacctcc agcct                                        25

SEQ ID NO: 12          moltype = DNA  length = 25
FEATURE                Location/Qualifiers
source                 1..25
                       mol_type = other DNA
                       organism = synthetic construct
SEQUENCE: 12
tgttctagat ttcctgtagc tgtga                                        25

SEQ ID NO: 13          moltype = DNA  length = 25
FEATURE                Location/Qualifiers
source                 1..25
                       mol_type = other DNA
                       organism = synthetic construct
SEQUENCE: 13
gtgctttagt tgctagtttg tactg                                        25
```

-continued

```
SEQ ID NO: 14          moltype = DNA  length = 25
FEATURE                Location/Qualifiers
source                 1..25
                       mol_type = other DNA
                       organism = synthetic construct
SEQUENCE: 14
cctgcgagaa gtcatctgca cgtcc                                        25

SEQ ID NO: 15          moltype = DNA  length = 25
FEATURE                Location/Qualifiers
source                 1..25
                       mol_type = other DNA
                       organism = synthetic construct
SEQUENCE: 15
gccattaaca gtgttttctt tccca                                        25

SEQ ID NO: 16          moltype = DNA  length = 25
FEATURE                Location/Qualifiers
source                 1..25
                       mol_type = other DNA
                       organism = synthetic construct
SEQUENCE: 16
cgcagccacg ccgatggtta tacag                                        25

SEQ ID NO: 17          moltype = DNA  length = 25
FEATURE                Location/Qualifiers
source                 1..25
                       mol_type = other DNA
                       organism = synthetic construct
SEQUENCE: 17
tcttgctaaa accggcaatt ctccg                                        25

SEQ ID NO: 18          moltype = DNA  length = 25
FEATURE                Location/Qualifiers
source                 1..25
                       mol_type = other DNA
                       organism = synthetic construct
SEQUENCE: 18
tgactccatt tctgtaagct actct                                        25

SEQ ID NO: 19          moltype = DNA  length = 25
FEATURE                Location/Qualifiers
source                 1..25
                       mol_type = other DNA
                       organism = synthetic construct
SEQUENCE: 19
ggtggtcttt caggttatct tggca                                        25

SEQ ID NO: 20          moltype = DNA  length = 25
FEATURE                Location/Qualifiers
source                 1..25
                       mol_type = other DNA
                       organism = synthetic construct
SEQUENCE: 20
tgtgtcttag atcctcatta tttta                                        25

SEQ ID NO: 21          moltype = DNA  length = 25
FEATURE                Location/Qualifiers
source                 1..25
                       mol_type = other DNA
                       organism = synthetic construct
SEQUENCE: 21
ctgtactctt cgcatggact gggaa                                        25

SEQ ID NO: 22          moltype = DNA  length = 25
FEATURE                Location/Qualifiers
source                 1..25
                       mol_type = other DNA
                       organism = synthetic construct
SEQUENCE: 22
cggctctagc cactgagcgg ctaaa                                        25

SEQ ID NO: 23          moltype = DNA  length = 25
FEATURE                Location/Qualifiers
source                 1..25
                       mol_type = other DNA
                       organism = synthetic construct
SEQUENCE: 23
aagattggtg ctttttgcat gtttg                                        25
```

-continued

```
SEQ ID NO: 24          moltype = DNA  length = 25
FEATURE                Location/Qualifiers
source                 1..25
                       mol_type = other DNA
                       organism = synthetic construct
SEQUENCE: 24
gccgagagag cctgccggat gatga                                        25

SEQ ID NO: 25          moltype = DNA  length = 25
FEATURE                Location/Qualifiers
source                 1..25
                       mol_type = other DNA
                       organism = synthetic construct
SEQUENCE: 25
ggagcaatct ccttggaagg attca                                        25

SEQ ID NO: 26          moltype = DNA  length = 25
FEATURE                Location/Qualifiers
source                 1..25
                       mol_type = other DNA
                       organism = synthetic construct
SEQUENCE: 26
gaaaagtcat ccctatttcc ttgtt                                        25

SEQ ID NO: 27          moltype = DNA  length = 25
FEATURE                Location/Qualifiers
source                 1..25
                       mol_type = other DNA
                       organism = synthetic construct
SEQUENCE: 27
agtgttgatg ggctctactt ctgat                                        25

SEQ ID NO: 28          moltype = DNA  length = 25
FEATURE                Location/Qualifiers
source                 1..25
                       mol_type = other DNA
                       organism = synthetic construct
SEQUENCE: 28
atttacctct aaatttccat atcct                                        25

SEQ ID NO: 29          moltype = DNA  length = 25
FEATURE                Location/Qualifiers
source                 1..25
                       mol_type = other DNA
                       organism = synthetic construct
SEQUENCE: 29
ggccttgtct aacttttgtg aagaa                                        25

SEQ ID NO: 30          moltype = DNA  length = 25
FEATURE                Location/Qualifiers
source                 1..25
                       mol_type = other DNA
                       organism = synthetic construct
SEQUENCE: 30
ccacagaaat ccagcatggc aactc                                        25

SEQ ID NO: 31          moltype = DNA  length = 25
FEATURE                Location/Qualifiers
source                 1..25
                       mol_type = other DNA
                       organism = synthetic construct
SEQUENCE: 31
aagatgaagc tctctttgct cttcc                                        25

SEQ ID NO: 32          moltype = DNA  length = 25
FEATURE                Location/Qualifiers
source                 1..25
                       mol_type = other DNA
                       organism = synthetic construct
SEQUENCE: 32
gagggggagg tttactctgc ggatc                                        25

SEQ ID NO: 33          moltype = DNA  length = 25
FEATURE                Location/Qualifiers
source                 1..25
                       mol_type = other DNA
                       organism = synthetic construct
SEQUENCE: 33
```

```
atcgcatcat gccaacttgt gactt                                      25

SEQ ID NO: 34          moltype = DNA  length = 25
FEATURE                Location/Qualifiers
source                 1..25
                       mol_type = other DNA
                       organism = synthetic construct
SEQUENCE: 34
ttttcctggc cgtggtagtt actca                                      25

SEQ ID NO: 35          moltype = DNA  length = 25
FEATURE                Location/Qualifiers
source                 1..25
                       mol_type = other DNA
                       organism = synthetic construct
SEQUENCE: 35
tcatcctctt agaagcacct gtgaa                                      25

SEQ ID NO: 36          moltype = DNA  length = 25
FEATURE                Location/Qualifiers
source                 1..25
                       mol_type = other DNA
                       organism = synthetic construct
SEQUENCE: 36
ggtagaggcg cttattgccc taacc                                      25

SEQ ID NO: 37          moltype = DNA  length = 25
FEATURE                Location/Qualifiers
source                 1..25
                       mol_type = other DNA
                       organism = synthetic construct
SEQUENCE: 37
tctttccttc agctcctgat gttaa                                      25

SEQ ID NO: 38          moltype = DNA  length = 25
FEATURE                Location/Qualifiers
source                 1..25
                       mol_type = other DNA
                       organism = synthetic construct
SEQUENCE: 38
catccaggac cgtgttcttt acgta                                      25

SEQ ID NO: 39          moltype = DNA  length = 25
FEATURE                Location/Qualifiers
source                 1..25
                       mol_type = other DNA
                       organism = synthetic construct
SEQUENCE: 39
tattccggaa tgagaccctg gacgc                                      25

SEQ ID NO: 40          moltype = DNA  length = 25
FEATURE                Location/Qualifiers
source                 1..25
                       mol_type = other DNA
                       organism = synthetic construct
SEQUENCE: 40
gctgcagctc tgacacaaca taatg                                      25

SEQ ID NO: 41          moltype = DNA  length = 25
FEATURE                Location/Qualifiers
source                 1..25
                       mol_type = other DNA
                       organism = synthetic construct
SEQUENCE: 41
gaggatcttg ttcaatcgga aaccc                                      25

SEQ ID NO: 42          moltype = DNA  length = 25
FEATURE                Location/Qualifiers
source                 1..25
                       mol_type = other DNA
                       organism = synthetic construct
SEQUENCE: 42
tgatgttctc aagcctcgga agtgg                                      25

SEQ ID NO: 43          moltype = DNA  length = 25
FEATURE                Location/Qualifiers
source                 1..25
                       mol_type = other DNA
                       organism = synthetic construct
```

-continued

```
SEQUENCE: 43
ttaactacga catgcctgag gactc                                             25

SEQ ID NO: 44           moltype = DNA  length = 25
FEATURE                 Location/Qualifiers
source                  1..25
                        mol_type = other DNA
                        organism = synthetic construct
SEQUENCE: 44
ccagaggccg acgatctact atgtg                                             25

SEQ ID NO: 45           moltype = DNA  length = 25
FEATURE                 Location/Qualifiers
source                  1..25
                        mol_type = other DNA
                        organism = synthetic construct
SEQUENCE: 45
gctacataca acctagtaca cttga                                             25

SEQ ID NO: 46           moltype = DNA  length = 25
FEATURE                 Location/Qualifiers
source                  1..25
                        mol_type = other DNA
                        organism = synthetic construct
SEQUENCE: 46
aatgcggctg tagaacatgc tgaaa                                             25

SEQ ID NO: 47           moltype = DNA  length = 25
FEATURE                 Location/Qualifiers
source                  1..25
                        mol_type = other DNA
                        organism = synthetic construct
SEQUENCE: 47
ccttctcctt actatagtcg tggag                                             25

SEQ ID NO: 48           moltype = DNA  length = 25
FEATURE                 Location/Qualifiers
source                  1..25
                        mol_type = other DNA
                        organism = synthetic construct
SEQUENCE: 48
cacaggtccc ggggcatcag gagaa                                             25

SEQ ID NO: 49           moltype = DNA  length = 25
FEATURE                 Location/Qualifiers
source                  1..25
                        mol_type = other DNA
                        organism = synthetic construct
SEQUENCE: 49
ccaaggggtg ctgtatgctc taggc                                             25

SEQ ID NO: 50           moltype = DNA  length = 25
FEATURE                 Location/Qualifiers
source                  1..25
                        mol_type = other DNA
                        organism = synthetic construct
SEQUENCE: 50
cagtttccac gagagcacag aaggg                                             25

SEQ ID NO: 51           moltype = DNA  length = 25
FEATURE                 Location/Qualifiers
source                  1..25
                        mol_type = other DNA
                        organism = synthetic construct
SEQUENCE: 51
ggcgccaatg gcgagatctg cgtca                                             25

SEQ ID NO: 52           moltype = DNA  length = 25
FEATURE                 Location/Qualifiers
source                  1..25
                        mol_type = other DNA
                        organism = synthetic construct
SEQUENCE: 52
gagaaggagc ggaggatggc caaca                                             25

SEQ ID NO: 53           moltype = DNA  length = 25
FEATURE                 Location/Qualifiers
source                  1..25
                        mol_type = other DNA
```

```
                       organism = synthetic construct
SEQUENCE: 53
gggtcaatgc attttggggt gagct                                           25

SEQ ID NO: 54          moltype = DNA  length = 25
FEATURE                Location/Qualifiers
source                 1..25
                       mol_type = other DNA
                       organism = synthetic construct
SEQUENCE: 54
caaacctttt cgttttactg atcat                                           25

SEQ ID NO: 55          moltype = DNA  length = 25
FEATURE                Location/Qualifiers
source                 1..25
                       mol_type = other DNA
                       organism = synthetic construct
SEQUENCE: 55
ttggtcaagg ccattacctg tttcc                                           25

SEQ ID NO: 56          moltype = DNA  length = 25
FEATURE                Location/Qualifiers
source                 1..25
                       mol_type = other DNA
                       organism = synthetic construct
SEQUENCE: 56
tatacccttt ctacagagtt gcctc                                           25

SEQ ID NO: 57          moltype = DNA  length = 25
FEATURE                Location/Qualifiers
source                 1..25
                       mol_type = other DNA
                       organism = synthetic construct
SEQUENCE: 57
gctgaacagg cctatcttga acttt                                           25

SEQ ID NO: 58          moltype = DNA  length = 25
FEATURE                Location/Qualifiers
source                 1..25
                       mol_type = other DNA
                       organism = synthetic construct
SEQUENCE: 58
taatggccaa ggctgtttgc atccc                                           25

SEQ ID NO: 59          moltype = DNA  length = 25
FEATURE                Location/Qualifiers
source                 1..25
                       mol_type = other DNA
                       organism = synthetic construct
SEQUENCE: 59
agcgaaagtg cattcagtcc atcct                                           25

SEQ ID NO: 60          moltype = DNA  length = 25
FEATURE                Location/Qualifiers
source                 1..25
                       mol_type = other DNA
                       organism = synthetic construct
SEQUENCE: 60
actgattatg gctcaggcta cccca                                           25

SEQ ID NO: 61          moltype = DNA  length = 25
FEATURE                Location/Qualifiers
source                 1..25
                       mol_type = other DNA
                       organism = synthetic construct
SEQUENCE: 61
gtgatcgagg atgctcgaca cccac                                           25

SEQ ID NO: 62          moltype = DNA  length = 25
FEATURE                Location/Qualifiers
source                 1..25
                       mol_type = other DNA
                       organism = synthetic construct
SEQUENCE: 62
ggcaggcaat tctaagatct tccac                                           25

SEQ ID NO: 63          moltype = DNA  length = 25
FEATURE                Location/Qualifiers
source                 1..25
```

-continued

```
                        mol_type = other DNA
                        organism = synthetic construct
SEQUENCE: 63
gtgatcgtag tcatgcctca gaagc                                             25

SEQ ID NO: 64           moltype = DNA  length = 25
FEATURE                 Location/Qualifiers
source                  1..25
                        mol_type = other DNA
                        organism = synthetic construct
SEQUENCE: 64
gatgggaagc gaaaggccaa ggacc                                             25

SEQ ID NO: 65           moltype = DNA  length = 25
FEATURE                 Location/Qualifiers
source                  1..25
                        mol_type = other DNA
                        organism = synthetic construct
SEQUENCE: 65
acagacatca ccagttgact tctgc                                             25

SEQ ID NO: 66           moltype = DNA  length = 25
FEATURE                 Location/Qualifiers
source                  1..25
                        mol_type = other DNA
                        organism = synthetic construct
SEQUENCE: 66
gtaactaggt ttttgcttct ccagt                                             25

SEQ ID NO: 67           moltype = DNA  length = 25
FEATURE                 Location/Qualifiers
source                  1..25
                        mol_type = other DNA
                        organism = synthetic construct
SEQUENCE: 67
cacagcttcc tagccacagt gataa                                             25

SEQ ID NO: 68           moltype = DNA  length = 25
FEATURE                 Location/Qualifiers
source                  1..25
                        mol_type = other DNA
                        organism = synthetic construct
SEQUENCE: 68
cggcagcgca agatgagggt gaatg                                             25

SEQ ID NO: 69           moltype = DNA  length = 25
FEATURE                 Location/Qualifiers
source                  1..25
                        mol_type = other DNA
                        organism = synthetic construct
SEQUENCE: 69
agatactcag cactagacta acata                                             25

SEQ ID NO: 70           moltype = DNA  length = 25
FEATURE                 Location/Qualifiers
source                  1..25
                        mol_type = other DNA
                        organism = synthetic construct
SEQUENCE: 70
cattgctata tgtgtctgtt ctact                                             25

SEQ ID NO: 71           moltype = DNA  length = 25
FEATURE                 Location/Qualifiers
source                  1..25
                        mol_type = other DNA
                        organism = synthetic construct
SEQUENCE: 71
gagacagctg cattgttgtg gaatt                                             25

SEQ ID NO: 72           moltype = DNA  length = 25
FEATURE                 Location/Qualifiers
source                  1..25
                        mol_type = other DNA
                        organism = synthetic construct
SEQUENCE: 72
gcctgatggg cctggtagtt ttcca                                             25

SEQ ID NO: 73           moltype = DNA  length = 25
FEATURE                 Location/Qualifiers
```

-continued

```
source                1..25
                      mol_type = other DNA
                      organism = synthetic construct
SEQUENCE: 73
gtaaccgtag caaaactgca ttggt                                          25

SEQ ID NO: 74         moltype = DNA  length = 25
FEATURE               Location/Qualifiers
source                1..25
                      mol_type = other DNA
                      organism = synthetic construct
SEQUENCE: 74
agatcggcat agtggagcca gtgct                                          25

SEQ ID NO: 75         moltype = DNA  length = 25
FEATURE               Location/Qualifiers
source                1..25
                      mol_type = other DNA
                      organism = synthetic construct
SEQUENCE: 75
tttgtaaaat gatgcttccc ccttc                                          25

SEQ ID NO: 76         moltype = DNA  length = 25
FEATURE               Location/Qualifiers
source                1..25
                      mol_type = other DNA
                      organism = synthetic construct
SEQUENCE: 76
aaggagatcg gcttgtggtt tcacc                                          25

SEQ ID NO: 77         moltype = DNA  length = 25
FEATURE               Location/Qualifiers
source                1..25
                      mol_type = other DNA
                      organism = synthetic construct
SEQUENCE: 77
acagcattgt acccagagtc tgtcc                                          25

SEQ ID NO: 78         moltype = DNA  length = 25
FEATURE               Location/Qualifiers
source                1..25
                      mol_type = other DNA
                      organism = synthetic construct
SEQUENCE: 78
tgcccaatcg gaagagctct gtgcc                                          25

SEQ ID NO: 79         moltype = DNA  length = 25
FEATURE               Location/Qualifiers
source                1..25
                      mol_type = other DNA
                      organism = synthetic construct
SEQUENCE: 79
aggtgccatt attctttcta gcctc                                          25

SEQ ID NO: 80         moltype = DNA  length = 25
FEATURE               Location/Qualifiers
source                1..25
                      mol_type = other DNA
                      organism = synthetic construct
SEQUENCE: 80
gaagctgtcc acgatgtctt ggatc                                          25

SEQ ID NO: 81         moltype = DNA  length = 25
FEATURE               Location/Qualifiers
source                1..25
                      mol_type = other DNA
                      organism = synthetic construct
SEQUENCE: 81
ggagcataaa agtgtaagac cgtaa                                          25

SEQ ID NO: 82         moltype = DNA  length = 25
FEATURE               Location/Qualifiers
source                1..25
                      mol_type = other DNA
                      organism = synthetic construct
SEQUENCE: 82
gatctttcag attttccatc tctag                                          25

SEQ ID NO: 83         moltype = DNA  length = 25
```

-continued

```
FEATURE                Location/Qualifiers
source                 1..25
                       mol_type = other DNA
                       organism = synthetic construct
SEQUENCE: 83
atgaccactg ttagcccatt atatt                                         25

SEQ ID NO: 84          moltype = DNA  length = 25
FEATURE                Location/Qualifiers
source                 1..25
                       mol_type = other DNA
                       organism = synthetic construct
SEQUENCE: 84
tagtatccag tccattgtac ctgct                                         25

SEQ ID NO: 85          moltype = DNA  length = 25
FEATURE                Location/Qualifiers
source                 1..25
                       mol_type = other DNA
                       organism = synthetic construct
SEQUENCE: 85
agatggtctc atcggagtcg cattt                                         25

SEQ ID NO: 86          moltype = DNA  length = 25
FEATURE                Location/Qualifiers
source                 1..25
                       mol_type = other DNA
                       organism = synthetic construct
SEQUENCE: 86
atatctatga ccactgttag cccat                                         25

SEQ ID NO: 87          moltype = DNA  length = 25
FEATURE                Location/Qualifiers
source                 1..25
                       mol_type = other DNA
                       organism = synthetic construct
SEQUENCE: 87
taaagcctat tctaccagtt aaact                                         25

SEQ ID NO: 88          moltype = DNA  length = 25
FEATURE                Location/Qualifiers
source                 1..25
                       mol_type = other DNA
                       organism = synthetic construct
SEQUENCE: 88
ggagcatcag ggttggcttg ggagc                                         25

SEQ ID NO: 89          moltype = DNA  length = 25
FEATURE                Location/Qualifiers
source                 1..25
                       mol_type = other DNA
                       organism = synthetic construct
SEQUENCE: 89
cattgacctc gagggcaacg tctgc                                         25

SEQ ID NO: 90          moltype = DNA  length = 25
FEATURE                Location/Qualifiers
source                 1..25
                       mol_type = other DNA
                       organism = synthetic construct
SEQUENCE: 90
ttatacgttt atatgctctg tctgc                                         25

SEQ ID NO: 91          moltype = DNA  length = 25
FEATURE                Location/Qualifiers
source                 1..25
                       mol_type = other DNA
                       organism = synthetic construct
SEQUENCE: 91
gttggccaca acattatgat tattc                                         25

SEQ ID NO: 92          moltype = DNA  length = 25
FEATURE                Location/Qualifiers
source                 1..25
                       mol_type = other DNA
                       organism = synthetic construct
SEQUENCE: 92
tcctgtgtgg tgtgtctact gtgag                                         25
```

```
SEQ ID NO: 93          moltype = DNA  length = 25
FEATURE                Location/Qualifiers
source                 1..25
                       mol_type = other DNA
                       organism = synthetic construct
SEQUENCE: 93
agagctgggg ttaggatccg gttgg                                        25

SEQ ID NO: 94          moltype = DNA  length = 25
FEATURE                Location/Qualifiers
source                 1..25
                       mol_type = other DNA
                       organism = synthetic construct
SEQUENCE: 94
tcctttctgt tttgcgagct tgtgt                                        25

SEQ ID NO: 95          moltype = DNA  length = 25
FEATURE                Location/Qualifiers
source                 1..25
                       mol_type = other DNA
                       organism = synthetic construct
SEQUENCE: 95
aaaagcccag tgtgacagtg tcatg                                        25

SEQ ID NO: 96          moltype = DNA  length = 25
FEATURE                Location/Qualifiers
source                 1..25
                       mol_type = other DNA
                       organism = synthetic construct
SEQUENCE: 96
cagtacaagc gctgcggtgt cacct                                        25

SEQ ID NO: 97          moltype = DNA  length = 25
FEATURE                Location/Qualifiers
source                 1..25
                       mol_type = other DNA
                       organism = synthetic construct
SEQUENCE: 97
gaaagccaac agacggtgct tcctc                                        25

SEQ ID NO: 98          moltype = DNA  length = 25
FEATURE                Location/Qualifiers
source                 1..25
                       mol_type = other DNA
                       organism = synthetic construct
SEQUENCE: 98
gtttacctct ggatacacta cttgt                                        25

SEQ ID NO: 99          moltype = DNA  length = 25
FEATURE                Location/Qualifiers
source                 1..25
                       mol_type = other DNA
                       organism = synthetic construct
SEQUENCE: 99
cgctctgccg agaccaggac gagct                                        25

SEQ ID NO: 100         moltype = DNA  length = 25
FEATURE                Location/Qualifiers
source                 1..25
                       mol_type = other DNA
                       organism = synthetic construct
SEQUENCE: 100
caccgacgtc agcaacttcg acgag                                        25

SEQ ID NO: 101         moltype = DNA  length = 25
FEATURE                Location/Qualifiers
source                 1..25
                       mol_type = other DNA
                       organism = synthetic construct
SEQUENCE: 101
aagcctacta gagccattgt atgtg                                        25

SEQ ID NO: 102         moltype = DNA  length = 25
FEATURE                Location/Qualifiers
source                 1..25
                       mol_type = other DNA
                       organism = synthetic construct
SEQUENCE: 102
cttcattact gaacaaaact acggt                                        25
```

```
SEQ ID NO: 103          moltype = DNA  length = 25
FEATURE                 Location/Qualifiers
source                  1..25
                        mol_type = other DNA
                        organism = synthetic construct
SEQUENCE: 103
tgctcatcaa ctgccgcaac aataa                                       25

SEQ ID NO: 104          moltype = DNA  length = 25
FEATURE                 Location/Qualifiers
source                  1..25
                        mol_type = other DNA
                        organism = synthetic construct
SEQUENCE: 104
atcccacctg tgagaatatg aactt                                       25

SEQ ID NO: 105          moltype = DNA  length = 25
FEATURE                 Location/Qualifiers
source                  1..25
                        mol_type = other DNA
                        organism = synthetic construct
SEQUENCE: 105
agctaaacac caatttcttc ctgct                                       25

SEQ ID NO: 106          moltype = DNA  length = 25
FEATURE                 Location/Qualifiers
source                  1..25
                        mol_type = other DNA
                        organism = synthetic construct
SEQUENCE: 106
tagtgagctg cctgatgaga tagac                                       25

SEQ ID NO: 107          moltype = DNA  length = 25
FEATURE                 Location/Qualifiers
source                  1..25
                        mol_type = other DNA
                        organism = synthetic construct
SEQUENCE: 107
gcagctatct taccagactg tgcct                                       25

SEQ ID NO: 108          moltype = DNA  length = 25
FEATURE                 Location/Qualifiers
source                  1..25
                        mol_type = other DNA
                        organism = synthetic construct
SEQUENCE: 108
gaagttcatg gatcaacatc cggag                                       25

SEQ ID NO: 109          moltype = DNA  length = 25
FEATURE                 Location/Qualifiers
source                  1..25
                        mol_type = other DNA
                        organism = synthetic construct
SEQUENCE: 109
ggtgacataa accattcatt gctac                                       25

SEQ ID NO: 110          moltype = DNA  length = 25
FEATURE                 Location/Qualifiers
source                  1..25
                        mol_type = other DNA
                        organism = synthetic construct
SEQUENCE: 110
aagtgcccaa ataagtctga gtgct                                       25

SEQ ID NO: 111          moltype = DNA  length = 25
FEATURE                 Location/Qualifiers
source                  1..25
                        mol_type = other DNA
                        organism = synthetic construct
SEQUENCE: 111
tttgacaagg agactggctt tcaca                                       25

SEQ ID NO: 112          moltype = DNA  length = 25
FEATURE                 Location/Qualifiers
source                  1..25
                        mol_type = other DNA
                        organism = synthetic construct
SEQUENCE: 112
```

```
aagtttgaat agcttctgtc cctct                                        25

SEQ ID NO: 113          moltype = DNA  length = 25
FEATURE                 Location/Qualifiers
source                  1..25
                        mol_type = other DNA
                        organism = synthetic construct
SEQUENCE: 113
tttggagttc tcttacgttt cctgg                                        25

SEQ ID NO: 114          moltype = DNA  length = 25
FEATURE                 Location/Qualifiers
source                  1..25
                        mol_type = other DNA
                        organism = synthetic construct
SEQUENCE: 114
tggcgagaga agcatgtccg gtcac                                        25

SEQ ID NO: 115          moltype = DNA  length = 25
FEATURE                 Location/Qualifiers
source                  1..25
                        mol_type = other DNA
                        organism = synthetic construct
SEQUENCE: 115
aataagtgcc gggagctttg tgaga                                        25

SEQ ID NO: 116          moltype = DNA  length = 25
FEATURE                 Location/Qualifiers
source                  1..25
                        mol_type = other DNA
                        organism = synthetic construct
SEQUENCE: 116
ggccagaaac cttgggtctt ttcat                                        25

SEQ ID NO: 117          moltype = DNA  length = 25
FEATURE                 Location/Qualifiers
source                  1..25
                        mol_type = other DNA
                        organism = synthetic construct
SEQUENCE: 117
ggatgtgggt ctgattgcaa ttcgg                                        25

SEQ ID NO: 118          moltype = DNA  length = 25
FEATURE                 Location/Qualifiers
source                  1..25
                        mol_type = other DNA
                        organism = synthetic construct
SEQUENCE: 118
tggaccatgg tctagcagta gcatc                                        25

SEQ ID NO: 119          moltype = DNA  length = 25
FEATURE                 Location/Qualifiers
source                  1..25
                        mol_type = other DNA
                        organism = synthetic construct
SEQUENCE: 119
gggcattcgc gtggtgaagg acctc                                        25

SEQ ID NO: 120          moltype = DNA  length = 25
FEATURE                 Location/Qualifiers
source                  1..25
                        mol_type = other DNA
                        organism = synthetic construct
SEQUENCE: 120
gctgtacccc aaggaagaca aggag                                        25

SEQ ID NO: 121          moltype = DNA  length = 25
FEATURE                 Location/Qualifiers
source                  1..25
                        mol_type = other DNA
                        organism = synthetic construct
SEQUENCE: 121
aaatctctga actgtgtggg ttttg                                        25

SEQ ID NO: 122          moltype = DNA  length = 25
FEATURE                 Location/Qualifiers
source                  1..25
                        mol_type = other DNA
                        organism = synthetic construct
```

```
SEQUENCE: 122
tgccctcaaa catacagaac ttcca                                    25

SEQ ID NO: 123          moltype = DNA  length = 25
FEATURE                 Location/Qualifiers
source                  1..25
                        mol_type = other DNA
                        organism = synthetic construct
SEQUENCE: 123
tcatctctag cagtatggca tcccc                                    25

SEQ ID NO: 124          moltype = DNA  length = 25
FEATURE                 Location/Qualifiers
source                  1..25
                        mol_type = other DNA
                        organism = synthetic construct
SEQUENCE: 124
gcaaggattg cggcgtgggt ttccg                                    25

SEQ ID NO: 125          moltype = DNA  length = 25
FEATURE                 Location/Qualifiers
source                  1..25
                        mol_type = other DNA
                        organism = synthetic construct
SEQUENCE: 125
tcaatggccg ctggtttgct ggccg                                    25

SEQ ID NO: 126          moltype = DNA  length = 25
FEATURE                 Location/Qualifiers
source                  1..25
                        mol_type = other DNA
                        organism = synthetic construct
SEQUENCE: 126
cacaccagct ctactcttta gtaaa                                    25

SEQ ID NO: 127          moltype = DNA  length = 25
FEATURE                 Location/Qualifiers
source                  1..25
                        mol_type = other DNA
                        organism = synthetic construct
SEQUENCE: 127
agaaactcac cctaaatctg aacgg                                    25

SEQ ID NO: 128          moltype = DNA  length = 25
FEATURE                 Location/Qualifiers
source                  1..25
                        mol_type = other DNA
                        organism = synthetic construct
SEQUENCE: 128
aagtggtaac aggactgatg ccgaa                                    25

SEQ ID NO: 129          moltype = DNA  length = 25
FEATURE                 Location/Qualifiers
source                  1..25
                        mol_type = other DNA
                        organism = synthetic construct
SEQUENCE: 129
tgtttataga tcactgccct ttttg                                    25

SEQ ID NO: 130          moltype = DNA  length = 25
FEATURE                 Location/Qualifiers
source                  1..25
                        mol_type = other DNA
                        organism = synthetic construct
SEQUENCE: 130
aagtcactca ggtcatgggc attgt                                    25

SEQ ID NO: 131          moltype = DNA  length = 25
FEATURE                 Location/Qualifiers
source                  1..25
                        mol_type = other DNA
                        organism = synthetic construct
SEQUENCE: 131
tgattactac ctcaggacca acctc                                    25

SEQ ID NO: 132          moltype = DNA  length = 25
FEATURE                 Location/Qualifiers
source                  1..25
                        mol_type = other DNA
```

-continued

```
                          organism = synthetic construct
SEQUENCE: 132
gtacttggat aggctggcta actcg                                          25

SEQ ID NO: 133            moltype = DNA  length = 25
FEATURE                   Location/Qualifiers
source                    1..25
                          mol_type = other DNA
                          organism = synthetic construct
SEQUENCE: 133
gaagctcgag agcccttaag ttctg                                          25

SEQ ID NO: 134            moltype = DNA  length = 25
FEATURE                   Location/Qualifiers
source                    1..25
                          mol_type = other DNA
                          organism = synthetic construct
SEQUENCE: 134
ccatcgacaa cacaaaccca gacgc                                          25

SEQ ID NO: 135            moltype = DNA  length = 25
FEATURE                   Location/Qualifiers
source                    1..25
                          mol_type = other DNA
                          organism = synthetic construct
SEQUENCE: 135
agcttgttgt tgatcagatt cactg                                          25

SEQ ID NO: 136            moltype = DNA  length = 25
FEATURE                   Location/Qualifiers
source                    1..25
                          mol_type = other DNA
                          organism = synthetic construct
SEQUENCE: 136
gcagagcatt cagtgccacg gttta                                          25

SEQ ID NO: 137            moltype = DNA  length = 25
FEATURE                   Location/Qualifiers
source                    1..25
                          mol_type = other DNA
                          organism = synthetic construct
SEQUENCE: 137
ctcttcagca gcatctactc taggc                                          25

SEQ ID NO: 138            moltype = DNA  length = 25
FEATURE                   Location/Qualifiers
source                    1..25
                          mol_type = other DNA
                          organism = synthetic construct
SEQUENCE: 138
ctgctgtaag gactggttcc agaat                                          25

SEQ ID NO: 139            moltype = DNA  length = 25
FEATURE                   Location/Qualifiers
source                    1..25
                          mol_type = other DNA
                          organism = synthetic construct
SEQUENCE: 139
gaacttgcca catacccagg tataa                                          25

SEQ ID NO: 140            moltype = DNA  length = 25
FEATURE                   Location/Qualifiers
source                    1..25
                          mol_type = other DNA
                          organism = synthetic construct
SEQUENCE: 140
catgaaggca cccttgaacc atcca                                          25

SEQ ID NO: 141            moltype = DNA  length = 25
FEATURE                   Location/Qualifiers
source                    1..25
                          mol_type = other DNA
                          organism = synthetic construct
SEQUENCE: 141
ggagccattg gctgtgaagc tgcag                                          25

SEQ ID NO: 142            moltype = DNA  length = 25
FEATURE                   Location/Qualifiers
source                    1..25
```

```
                        mol_type = other DNA
                        organism = synthetic construct
SEQUENCE: 142
aatctgaccc tatcggaaac tcaaa                                          25

SEQ ID NO: 143          moltype = DNA  length = 25
FEATURE                 Location/Qualifiers
source                  1..25
                        mol_type = other DNA
                        organism = synthetic construct
SEQUENCE: 143
atagcctcag gaacagtcca gactg                                          25

SEQ ID NO: 144          moltype = DNA  length = 25
FEATURE                 Location/Qualifiers
source                  1..25
                        mol_type = other DNA
                        organism = synthetic construct
SEQUENCE: 144
ggtggtgatc aaaactatag tggct                                          25

SEQ ID NO: 145          moltype = DNA  length = 25
FEATURE                 Location/Qualifiers
source                  1..25
                        mol_type = other DNA
                        organism = synthetic construct
SEQUENCE: 145
tgatcaccct gcaatcctat tatgt                                          25

SEQ ID NO: 146          moltype = DNA  length = 25
FEATURE                 Location/Qualifiers
source                  1..25
                        mol_type = other DNA
                        organism = synthetic construct
SEQUENCE: 146
acttagaatc catctcacta ccaat                                          25

SEQ ID NO: 147          moltype = DNA  length = 25
FEATURE                 Location/Qualifiers
source                  1..25
                        mol_type = other DNA
                        organism = synthetic construct
SEQUENCE: 147
tagagactat gtcgctttcc tgagc                                          25

SEQ ID NO: 148          moltype = DNA  length = 25
FEATURE                 Location/Qualifiers
source                  1..25
                        mol_type = other DNA
                        organism = synthetic construct
SEQUENCE: 148
tactgtgatg ggcagaacag ccttt                                          25

SEQ ID NO: 149          moltype = DNA  length = 25
FEATURE                 Location/Qualifiers
source                  1..25
                        mol_type = other DNA
                        organism = synthetic construct
SEQUENCE: 149
tctcatttag gactgggttc cccac                                          25

SEQ ID NO: 150          moltype = DNA  length = 25
FEATURE                 Location/Qualifiers
source                  1..25
                        mol_type = other DNA
                        organism = synthetic construct
SEQUENCE: 150
acagctttta acacagttcc ctgcc                                          25

SEQ ID NO: 151          moltype = DNA  length = 25
FEATURE                 Location/Qualifiers
source                  1..25
                        mol_type = other DNA
                        organism = synthetic construct
SEQUENCE: 151
gatgaaagat gagcccaagt ccacc                                          25

SEQ ID NO: 152          moltype = DNA  length = 25
FEATURE                 Location/Qualifiers
```

```
source                  1..25
                        mol_type = other DNA
                        organism = synthetic construct
SEQUENCE: 152
gatcctctta aaacgtttat attct                                         25

SEQ ID NO: 153          moltype = DNA  length = 25
FEATURE                 Location/Qualifiers
source                  1..25
                        mol_type = other DNA
                        organism = synthetic construct
SEQUENCE: 153
ccctggtcac atgtcatcgg gctgg                                         25

SEQ ID NO: 154          moltype = DNA  length = 25
FEATURE                 Location/Qualifiers
source                  1..25
                        mol_type = other DNA
                        organism = synthetic construct
SEQUENCE: 154
atccacatca gaatcccttg tagga                                         25

SEQ ID NO: 155          moltype = DNA  length = 25
FEATURE                 Location/Qualifiers
source                  1..25
                        mol_type = other DNA
                        organism = synthetic construct
SEQUENCE: 155
actgctttca agctggactg agcca                                         25

SEQ ID NO: 156          moltype = DNA  length = 25
FEATURE                 Location/Qualifiers
source                  1..25
                        mol_type = other DNA
                        organism = synthetic construct
SEQUENCE: 156
taaacattcc gtccctgttt gagac                                         25

SEQ ID NO: 157          moltype = DNA  length = 25
FEATURE                 Location/Qualifiers
source                  1..25
                        mol_type = other DNA
                        organism = synthetic construct
SEQUENCE: 157
gtgagatcaa agctcctcca aagcc                                         25

SEQ ID NO: 158          moltype = DNA  length = 25
FEATURE                 Location/Qualifiers
source                  1..25
                        mol_type = other DNA
                        organism = synthetic construct
SEQUENCE: 158
cctcggtggc cctgactgtc aggga                                         25

SEQ ID NO: 159          moltype = DNA  length = 25
FEATURE                 Location/Qualifiers
source                  1..25
                        mol_type = other DNA
                        organism = synthetic construct
SEQUENCE: 159
tcacgccgat gatggagctg aagcc                                         25

SEQ ID NO: 160          moltype = DNA  length = 25
FEATURE                 Location/Qualifiers
source                  1..25
                        mol_type = other DNA
                        organism = synthetic construct
SEQUENCE: 160
gagttctatt tgagacttcc agccc                                         25

SEQ ID NO: 161          moltype = DNA  length = 25
FEATURE                 Location/Qualifiers
source                  1..25
                        mol_type = other DNA
                        organism = synthetic construct
SEQUENCE: 161
ccaaaggagg cattatgctt ccaga                                         25

SEQ ID NO: 162          moltype = DNA  length = 25
```

```
FEATURE                Location/Qualifiers
source                 1..25
                       mol_type = other DNA
                       organism = synthetic construct
SEQUENCE: 162
gaagtgtgct agtatgctcc ctagt                                         25

SEQ ID NO: 163         moltype = DNA  length = 25
FEATURE                Location/Qualifiers
source                 1..25
                       mol_type = other DNA
                       organism = synthetic construct
SEQUENCE: 163
gttggggttg gagacgtgtg taata                                         25

SEQ ID NO: 164         moltype = DNA  length = 25
FEATURE                Location/Qualifiers
source                 1..25
                       mol_type = other DNA
                       organism = synthetic construct
SEQUENCE: 164
ggaggctaag tattgctttc tacaa                                         25

SEQ ID NO: 165         moltype = DNA  length = 25
FEATURE                Location/Qualifiers
source                 1..25
                       mol_type = other DNA
                       organism = synthetic construct
SEQUENCE: 165
tcattagctc tgccctttt aatta                                          25

SEQ ID NO: 166         moltype = DNA  length = 25
FEATURE                Location/Qualifiers
source                 1..25
                       mol_type = other DNA
                       organism = synthetic construct
SEQUENCE: 166
cacttctcct ttacgctgtg tagag                                         25

SEQ ID NO: 167         moltype = DNA  length = 25
FEATURE                Location/Qualifiers
source                 1..25
                       mol_type = other DNA
                       organism = synthetic construct
SEQUENCE: 167
gtactttgat actgctcatg ctgac                                         25

SEQ ID NO: 168         moltype = DNA  length = 25
FEATURE                Location/Qualifiers
source                 1..25
                       mol_type = other DNA
                       organism = synthetic construct
SEQUENCE: 168
caggggatgg cctgatcgag ctgcg                                         25

SEQ ID NO: 169         moltype = DNA  length = 25
FEATURE                Location/Qualifiers
source                 1..25
                       mol_type = other DNA
                       organism = synthetic construct
SEQUENCE: 169
ccttattcca ttcttaactc tgcat                                         25

SEQ ID NO: 170         moltype = DNA  length = 25
FEATURE                Location/Qualifiers
source                 1..25
                       mol_type = other DNA
                       organism = synthetic construct
SEQUENCE: 170
gcagtcactc tccctgaata agtaa                                         25

SEQ ID NO: 171         moltype = DNA  length = 25
FEATURE                Location/Qualifiers
source                 1..25
                       mol_type = other DNA
                       organism = synthetic construct
SEQUENCE: 171
gaagaagaac tagccagtac tcccc                                         25
```

```
SEQ ID NO: 172         moltype = DNA  length = 25
FEATURE                Location/Qualifiers
source                 1..25
                       mol_type = other DNA
                       organism = synthetic construct
SEQUENCE: 172
ggagtgccaa gtttgcaaac ctgca                                        25

SEQ ID NO: 173         moltype = DNA  length = 25
FEATURE                Location/Qualifiers
source                 1..25
                       mol_type = other DNA
                       organism = synthetic construct
SEQUENCE: 173
aatgggttat cacaggaatg ggact                                        25

SEQ ID NO: 174         moltype = DNA  length = 25
FEATURE                Location/Qualifiers
source                 1..25
                       mol_type = other DNA
                       organism = synthetic construct
SEQUENCE: 174
tgggcagagt gcggcagctc atgcc                                        25

SEQ ID NO: 175         moltype = DNA  length = 25
FEATURE                Location/Qualifiers
source                 1..25
                       mol_type = other DNA
                       organism = synthetic construct
SEQUENCE: 175
tggagtgaga ctgactgcaa gcccc                                        25

SEQ ID NO: 176         moltype = DNA  length = 25
FEATURE                Location/Qualifiers
source                 1..25
                       mol_type = other DNA
                       organism = synthetic construct
SEQUENCE: 176
tttttggatg gcaacgagct caccc                                        25

SEQ ID NO: 177         moltype = DNA  length = 25
FEATURE                Location/Qualifiers
source                 1..25
                       mol_type = other DNA
                       organism = synthetic construct
SEQUENCE: 177
ttattgctta atttctgcct ttccc                                        25

SEQ ID NO: 178         moltype = DNA  length = 25
FEATURE                Location/Qualifiers
source                 1..25
                       mol_type = other DNA
                       organism = synthetic construct
SEQUENCE: 178
gctgccttgt gtgcgactga gatgc                                        25

SEQ ID NO: 179         moltype = DNA  length = 25
FEATURE                Location/Qualifiers
source                 1..25
                       mol_type = other DNA
                       organism = synthetic construct
SEQUENCE: 179
ctacgatgag tttgagtact gctgg                                        25

SEQ ID NO: 180         moltype = DNA  length = 25
FEATURE                Location/Qualifiers
source                 1..25
                       mol_type = other DNA
                       organism = synthetic construct
SEQUENCE: 180
ctcctggact caatcatggc ttgtg                                        25

SEQ ID NO: 181         moltype = DNA  length = 25
FEATURE                Location/Qualifiers
source                 1..25
                       mol_type = other DNA
                       organism = synthetic construct
SEQUENCE: 181
tggagggcgc tcatcaagta gctgc                                        25
```

```
SEQ ID NO: 182          moltype = DNA  length = 25
FEATURE                 Location/Qualifiers
source                  1..25
                        mol_type = other DNA
                        organism = synthetic construct
SEQUENCE: 182
tggtcccagc cagtttggtg ctgac                                       25

SEQ ID NO: 183          moltype = DNA  length = 25
FEATURE                 Location/Qualifiers
source                  1..25
                        mol_type = other DNA
                        organism = synthetic construct
SEQUENCE: 183
gatcctttct gtaggctaat tcctc                                       25

SEQ ID NO: 184          moltype = DNA  length = 25
FEATURE                 Location/Qualifiers
source                  1..25
                        mol_type = other DNA
                        organism = synthetic construct
SEQUENCE: 184
ttcccagaag cggacctgag gaccc                                       25

SEQ ID NO: 185          moltype = DNA  length = 25
FEATURE                 Location/Qualifiers
source                  1..25
                        mol_type = other DNA
                        organism = synthetic construct
SEQUENCE: 185
gaccttcaag ggtcctcgtt ttgat                                       25

SEQ ID NO: 186          moltype = DNA  length = 25
FEATURE                 Location/Qualifiers
source                  1..25
                        mol_type = other DNA
                        organism = synthetic construct
SEQUENCE: 186
gacggtgctt ttcggtgcaa ggaaa                                       25

SEQ ID NO: 187          moltype = DNA  length = 25
FEATURE                 Location/Qualifiers
source                  1..25
                        mol_type = other DNA
                        organism = synthetic construct
SEQUENCE: 187
tgaacttgtt gagatccccg tgtta                                       25

SEQ ID NO: 188          moltype = DNA  length = 25
FEATURE                 Location/Qualifiers
source                  1..25
                        mol_type = other DNA
                        organism = synthetic construct
SEQUENCE: 188
ttctactcag gcacgggcta caagc                                       25

SEQ ID NO: 189          moltype = DNA  length = 25
FEATURE                 Location/Qualifiers
source                  1..25
                        mol_type = other DNA
                        organism = synthetic construct
SEQUENCE: 189
ccggtgtcct tgaccacatg aagaa                                       25

SEQ ID NO: 190          moltype = DNA  length = 25
FEATURE                 Location/Qualifiers
source                  1..25
                        mol_type = other DNA
                        organism = synthetic construct
SEQUENCE: 190
tgatgcactg attccatccc aggaa                                       25

SEQ ID NO: 191          moltype = DNA  length = 25
FEATURE                 Location/Qualifiers
source                  1..25
                        mol_type = other DNA
                        organism = synthetic construct
SEQUENCE: 191
```

```
tgacagtcac tagcttatct tgaac                                        25

SEQ ID NO: 192          moltype = DNA  length = 25
FEATURE                 Location/Qualifiers
source                  1..25
                        mol_type = other DNA
                        organism = synthetic construct
SEQUENCE: 192
ttgtgtgaag tggttcaccc ttgag                                        25

SEQ ID NO: 193          moltype = DNA  length = 25
FEATURE                 Location/Qualifiers
source                  1..25
                        mol_type = other DNA
                        organism = synthetic construct
SEQUENCE: 193
gacttccgga tcctgtcagg gtgtc                                        25

SEQ ID NO: 194          moltype = DNA  length = 25
FEATURE                 Location/Qualifiers
source                  1..25
                        mol_type = other DNA
                        organism = synthetic construct
SEQUENCE: 194
gacaaagatc ttgccttaca gactt                                        25

SEQ ID NO: 195          moltype = DNA  length = 25
FEATURE                 Location/Qualifiers
source                  1..25
                        mol_type = other DNA
                        organism = synthetic construct
SEQUENCE: 195
tggtcgcagc tgtgctgttc atcac                                        25

SEQ ID NO: 196          moltype = DNA  length = 25
FEATURE                 Location/Qualifiers
source                  1..25
                        mol_type = other DNA
                        organism = synthetic construct
SEQUENCE: 196
gtgacttcaa gagcctctgg catct                                        25

SEQ ID NO: 197          moltype = DNA  length = 25
FEATURE                 Location/Qualifiers
source                  1..25
                        mol_type = other DNA
                        organism = synthetic construct
SEQUENCE: 197
gagaacaaca gcattcattt ccatt                                        25

SEQ ID NO: 198          moltype = DNA  length = 25
FEATURE                 Location/Qualifiers
source                  1..25
                        mol_type = other DNA
                        organism = synthetic construct
SEQUENCE: 198
ccctcaccct gagatgggag ccgtc                                        25

SEQ ID NO: 199          moltype = DNA  length = 25
FEATURE                 Location/Qualifiers
source                  1..25
                        mol_type = other DNA
                        organism = synthetic construct
SEQUENCE: 199
caccatcccc aacttgggca tcgtt                                        25

SEQ ID NO: 200          moltype = DNA  length = 25
FEATURE                 Location/Qualifiers
source                  1..25
                        mol_type = other DNA
                        organism = synthetic construct
SEQUENCE: 200
agtaaatgat tcctccttgt tctgt                                        25

SEQ ID NO: 201          moltype = DNA  length = 25
FEATURE                 Location/Qualifiers
source                  1..25
                        mol_type = other DNA
                        organism = synthetic construct
```

```
SEQUENCE: 201
caaaacgggc atcacccagt tgacc                                          25

SEQ ID NO: 202          moltype = DNA  length = 25
FEATURE                 Location/Qualifiers
source                  1..25
                        mol_type = other DNA
                        organism = synthetic construct
SEQUENCE: 202
aaggagggca cctctgtctg agttt                                          25

SEQ ID NO: 203          moltype = DNA  length = 25
FEATURE                 Location/Qualifiers
source                  1..25
                        mol_type = other DNA
                        organism = synthetic construct
SEQUENCE: 203
ttatttatac agtgccttgc tcggg                                          25

SEQ ID NO: 204          moltype = DNA  length = 25
FEATURE                 Location/Qualifiers
source                  1..25
                        mol_type = other DNA
                        organism = synthetic construct
SEQUENCE: 204
ttcggggaca atctggtcac ccgct                                          25

SEQ ID NO: 205          moltype = DNA  length = 25
FEATURE                 Location/Qualifiers
source                  1..25
                        mol_type = other DNA
                        organism = synthetic construct
SEQUENCE: 205
cctcattgag ttcggtgcat ctggc                                          25

SEQ ID NO: 206          moltype = DNA  length = 25
FEATURE                 Location/Qualifiers
source                  1..25
                        mol_type = other DNA
                        organism = synthetic construct
SEQUENCE: 206
tgcttgctac cgtgttcgga gtctc                                          25

SEQ ID NO: 207          moltype = DNA  length = 25
FEATURE                 Location/Qualifiers
source                  1..25
                        mol_type = other DNA
                        organism = synthetic construct
SEQUENCE: 207
ccctgcacat gaagaggcac ctctg                                          25

SEQ ID NO: 208          moltype = DNA  length = 25
FEATURE                 Location/Qualifiers
source                  1..25
                        mol_type = other DNA
                        organism = synthetic construct
SEQUENCE: 208
ggctgtccta gcagttgtgg tcatc                                          25

SEQ ID NO: 209          moltype = DNA  length = 25
FEATURE                 Location/Qualifiers
source                  1..25
                        mol_type = other DNA
                        organism = synthetic construct
SEQUENCE: 209
gtcacacacc agcactttat acact                                          25

SEQ ID NO: 210          moltype = DNA  length = 25
FEATURE                 Location/Qualifiers
source                  1..25
                        mol_type = other DNA
                        organism = synthetic construct
SEQUENCE: 210
gaacactcta ctacatgtga ctggc                                          25

SEQ ID NO: 211          moltype = DNA  length = 25
FEATURE                 Location/Qualifiers
source                  1..25
                        mol_type = other DNA
```

```
                         organism = synthetic construct
SEQUENCE: 211
gaggactact ctggatcagg cttcg                                          25

SEQ ID NO: 212           moltype = DNA  length = 25
FEATURE                  Location/Qualifiers
source                   1..25
                         mol_type = other DNA
                         organism = synthetic construct
SEQUENCE: 212
gagctagtgg atgtgtttgt ctaca                                          25

SEQ ID NO: 213           moltype = DNA  length = 25
FEATURE                  Location/Qualifiers
source                   1..25
                         mol_type = other DNA
                         organism = synthetic construct
SEQUENCE: 213
ttccttcctt atcactgaca caaaa                                          25

SEQ ID NO: 214           moltype = DNA  length = 25
FEATURE                  Location/Qualifiers
source                   1..25
                         mol_type = other DNA
                         organism = synthetic construct
SEQUENCE: 214
ggactctatt ccatctatca agggg                                          25

SEQ ID NO: 215           moltype = DNA  length = 25
FEATURE                  Location/Qualifiers
source                   1..25
                         mol_type = other DNA
                         organism = synthetic construct
SEQUENCE: 215
ccccatcgtg ggcattgttg ctggc                                          25

SEQ ID NO: 216           moltype = DNA  length = 25
FEATURE                  Location/Qualifiers
source                   1..25
                         mol_type = other DNA
                         organism = synthetic construct
SEQUENCE: 216
gcggattctt cagcgagatc tcgca                                          25

SEQ ID NO: 217           moltype = DNA  length = 25
FEATURE                  Location/Qualifiers
source                   1..25
                         mol_type = other DNA
                         organism = synthetic construct
SEQUENCE: 217
ctcaccagtg cttcatatac catga                                          25

SEQ ID NO: 218           moltype = DNA  length = 25
FEATURE                  Location/Qualifiers
source                   1..25
                         mol_type = other DNA
                         organism = synthetic construct
SEQUENCE: 218
gcaagtttca tcagccctag ggaaa                                          25

SEQ ID NO: 219           moltype = DNA  length = 25
FEATURE                  Location/Qualifiers
source                   1..25
                         mol_type = other DNA
                         organism = synthetic construct
SEQUENCE: 219
ctcagcttcc ctcttaagct aagac                                          25

SEQ ID NO: 220           moltype = DNA  length = 25
FEATURE                  Location/Qualifiers
source                   1..25
                         mol_type = other DNA
                         organism = synthetic construct
SEQUENCE: 220
ccccatcgtg ggcattgttg ctggc                                          25

SEQ ID NO: 221           moltype = DNA  length = 25
FEATURE                  Location/Qualifiers
source                   1..25
```

```
                         mol_type = other DNA
                         organism = synthetic construct
SEQUENCE: 221
gaatgttctc caagcagcaa tccaa                                            25

SEQ ID NO: 222           moltype = DNA  length = 25
FEATURE                  Location/Qualifiers
source                   1..25
                         mol_type = other DNA
                         organism = synthetic construct
SEQUENCE: 222
atgtgcgtgt cgtcgctgtt tagac                                            25

SEQ ID NO: 223           moltype = DNA  length = 25
FEATURE                  Location/Qualifiers
source                   1..25
                         mol_type = other DNA
                         organism = synthetic construct
SEQUENCE: 223
cacaagcccc tgaaccatat attgt                                            25

SEQ ID NO: 224           moltype = DNA  length = 25
FEATURE                  Location/Qualifiers
source                   1..25
                         mol_type = other DNA
                         organism = synthetic construct
SEQUENCE: 224
gatgtggacg ttcgggagct actgc                                            25

SEQ ID NO: 225           moltype = DNA  length = 25
FEATURE                  Location/Qualifiers
source                   1..25
                         mol_type = other DNA
                         organism = synthetic construct
SEQUENCE: 225
tcctgttgtt tgctgccatt ggcat                                            25

SEQ ID NO: 226           moltype = DNA  length = 25
FEATURE                  Location/Qualifiers
source                   1..25
                         mol_type = other DNA
                         organism = synthetic construct
SEQUENCE: 226
gtggccagca ctctgaaact gagaa                                            25

SEQ ID NO: 227           moltype = DNA  length = 25
FEATURE                  Location/Qualifiers
source                   1..25
                         mol_type = other DNA
                         organism = synthetic construct
SEQUENCE: 227
agttccgctt gtccaagatc tggtc                                            25

SEQ ID NO: 228           moltype = DNA  length = 25
FEATURE                  Location/Qualifiers
source                   1..25
                         mol_type = other DNA
                         organism = synthetic construct
SEQUENCE: 228
agagccccag tttgtaaatg aacct                                            25

SEQ ID NO: 229           moltype = DNA  length = 25
FEATURE                  Location/Qualifiers
source                   1..25
                         mol_type = other DNA
                         organism = synthetic construct
SEQUENCE: 229
gtccccaagt gtgcaagctc agtat                                            25

SEQ ID NO: 230           moltype = DNA  length = 25
FEATURE                  Location/Qualifiers
source                   1..25
                         mol_type = other DNA
                         organism = synthetic construct
SEQUENCE: 230
gacgtggagc tcgtggagac caggc                                            25

SEQ ID NO: 231           moltype = DNA  length = 25
FEATURE                  Location/Qualifiers
```

```
source                  1..25
                        mol_type = other DNA
                        organism = synthetic construct
SEQUENCE: 231
tttttgcttc aagctctgta gcagg                                         25

SEQ ID NO: 232          moltype = DNA  length = 25
FEATURE                 Location/Qualifiers
source                  1..25
                        mol_type = other DNA
                        organism = synthetic construct
SEQUENCE: 232
tccatttctg gcagcagcct ggagc                                         25

SEQ ID NO: 233          moltype = DNA  length = 25
FEATURE                 Location/Qualifiers
source                  1..25
                        mol_type = other DNA
                        organism = synthetic construct
SEQUENCE: 233
tctaccccag gtcagacgga cagaa                                         25

SEQ ID NO: 234          moltype = DNA  length = 25
FEATURE                 Location/Qualifiers
source                  1..25
                        mol_type = other DNA
                        organism = synthetic construct
SEQUENCE: 234
acgggctgtc cgtgtgcctc ctgtg                                         25

SEQ ID NO: 235          moltype = DNA  length = 25
FEATURE                 Location/Qualifiers
source                  1..25
                        mol_type = other DNA
                        organism = synthetic construct
SEQUENCE: 235
ggtggagtca gtgaccaggt cgtct                                         25

SEQ ID NO: 236          moltype = DNA  length = 25
FEATURE                 Location/Qualifiers
source                  1..25
                        mol_type = other DNA
                        organism = synthetic construct
SEQUENCE: 236
ctaacccacc ggcagagtat ttttg                                         25

SEQ ID NO: 237          moltype = DNA  length = 25
FEATURE                 Location/Qualifiers
source                  1..25
                        mol_type = other DNA
                        organism = synthetic construct
SEQUENCE: 237
gctttcgaag tggccagctg cggcc                                         25

SEQ ID NO: 238          moltype = DNA  length = 25
FEATURE                 Location/Qualifiers
source                  1..25
                        mol_type = other DNA
                        organism = synthetic construct
SEQUENCE: 238
gtgttagaag cagctgtggg ggtcc                                         25

SEQ ID NO: 239          moltype = DNA  length = 25
FEATURE                 Location/Qualifiers
source                  1..25
                        mol_type = other DNA
                        organism = synthetic construct
SEQUENCE: 239
gagtgaggcg atttgacctg ctcaa                                         25

SEQ ID NO: 240          moltype = DNA  length = 25
FEATURE                 Location/Qualifiers
source                  1..25
                        mol_type = other DNA
                        organism = synthetic construct
SEQUENCE: 240
taagggcttg attcctagcc ccgtt                                         25

SEQ ID NO: 241          moltype = DNA  length = 25
```

-continued

```
FEATURE                 Location/Qualifiers
source                  1..25
                        mol_type = other DNA
                        organism = synthetic construct
SEQUENCE: 241
aggggcctct gaacggaaca gtgtc                                            25

SEQ ID NO: 242          moltype = DNA  length = 25
FEATURE                 Location/Qualifiers
source                  1..25
                        mol_type = other DNA
                        organism = synthetic construct
SEQUENCE: 242
tgagcacgct cagttctact gtgtc                                            25

SEQ ID NO: 243          moltype = DNA  length = 25
FEATURE                 Location/Qualifiers
source                  1..25
                        mol_type = other DNA
                        organism = synthetic construct
SEQUENCE: 243
gtcttcgtcc gataccaata agtca                                            25

SEQ ID NO: 244          moltype = DNA  length = 25
FEATURE                 Location/Qualifiers
source                  1..25
                        mol_type = other DNA
                        organism = synthetic construct
SEQUENCE: 244
agctgagcca catcaagaca cggtc                                            25

SEQ ID NO: 245          moltype = DNA  length = 25
FEATURE                 Location/Qualifiers
source                  1..25
                        mol_type = other DNA
                        organism = synthetic construct
SEQUENCE: 245
cttatttacc ggaagcttct gttca                                            25

SEQ ID NO: 246          moltype = DNA  length = 25
FEATURE                 Location/Qualifiers
source                  1..25
                        mol_type = other DNA
                        organism = synthetic construct
SEQUENCE: 246
tgccttcatc ctaactgctg gggaa                                            25

SEQ ID NO: 247          moltype = DNA  length = 25
FEATURE                 Location/Qualifiers
source                  1..25
                        mol_type = other DNA
                        organism = synthetic construct
SEQUENCE: 247
gaggcaccac taaaagatcg cagtt                                            25

SEQ ID NO: 248          moltype = DNA  length = 25
FEATURE                 Location/Qualifiers
source                  1..25
                        mol_type = other DNA
                        organism = synthetic construct
SEQUENCE: 248
taccctgcgg agatcatact gacct                                            25

SEQ ID NO: 249          moltype = DNA  length = 25
FEATURE                 Location/Qualifiers
source                  1..25
                        mol_type = other DNA
                        organism = synthetic construct
SEQUENCE: 249
ggatgggaag tgttgcattg agcat                                            25

SEQ ID NO: 250          moltype = DNA  length = 25
FEATURE                 Location/Qualifiers
source                  1..25
                        mol_type = other DNA
                        organism = synthetic construct
SEQUENCE: 250
cttggagata tttccgtcct ccacc                                            25
```

```
SEQ ID NO: 251          moltype = DNA  length = 25
FEATURE                 Location/Qualifiers
source                  1..25
                        mol_type = other DNA
                        organism = synthetic construct
SEQUENCE: 251
aggcctctca tgacccagga aggcc                                        25

SEQ ID NO: 252          moltype = DNA  length = 25
FEATURE                 Location/Qualifiers
source                  1..25
                        mol_type = other DNA
                        organism = synthetic construct
SEQUENCE: 252
tcatcactat tattgctcac cactg                                        25

SEQ ID NO: 253          moltype = DNA  length = 25
FEATURE                 Location/Qualifiers
source                  1..25
                        mol_type = other DNA
                        organism = synthetic construct
SEQUENCE: 253
aagctgacac ctaagtttac caaca                                        25

SEQ ID NO: 254          moltype = DNA  length = 25
FEATURE                 Location/Qualifiers
source                  1..25
                        mol_type = other DNA
                        organism = synthetic construct
SEQUENCE: 254
taggtgtctg ccttcacaaa tgtca                                        25

SEQ ID NO: 255          moltype = DNA  length = 25
FEATURE                 Location/Qualifiers
source                  1..25
                        mol_type = other DNA
                        organism = synthetic construct
SEQUENCE: 255
atattcccta tgtagcaaca gtggt                                        25

SEQ ID NO: 256          moltype = DNA  length = 25
FEATURE                 Location/Qualifiers
source                  1..25
                        mol_type = other DNA
                        organism = synthetic construct
SEQUENCE: 256
gatcatgctg aaaaccactc aaacg                                        25

SEQ ID NO: 257          moltype = DNA  length = 25
FEATURE                 Location/Qualifiers
source                  1..25
                        mol_type = other DNA
                        organism = synthetic construct
SEQUENCE: 257
aaggtccata aagactgagc ggatg                                        25

SEQ ID NO: 258          moltype = DNA  length = 25
FEATURE                 Location/Qualifiers
source                  1..25
                        mol_type = other DNA
                        organism = synthetic construct
SEQUENCE: 258
ctgaggagtc caacatcacc atgca                                        25

SEQ ID NO: 259          moltype = DNA  length = 25
FEATURE                 Location/Qualifiers
source                  1..25
                        mol_type = other DNA
                        organism = synthetic construct
SEQUENCE: 259
ggacgacacc tctggttttt caata                                        25

SEQ ID NO: 260          moltype = DNA  length = 25
FEATURE                 Location/Qualifiers
source                  1..25
                        mol_type = other DNA
                        organism = synthetic construct
SEQUENCE: 260
ttcactccat ccctatggca gagga                                        25
```

```
SEQ ID NO: 261          moltype = DNA  length = 25
FEATURE                 Location/Qualifiers
source                  1..25
                        mol_type = other DNA
                        organism = synthetic construct
SEQUENCE: 261
gagatgcatt taaggccgat agtga                                         25

SEQ ID NO: 262          moltype = DNA  length = 25
FEATURE                 Location/Qualifiers
source                  1..25
                        mol_type = other DNA
                        organism = synthetic construct
SEQUENCE: 262
tcgttacagg gagtccaaca ccgcc                                         25

SEQ ID NO: 263          moltype = DNA  length = 25
FEATURE                 Location/Qualifiers
source                  1..25
                        mol_type = other DNA
                        organism = synthetic construct
SEQUENCE: 263
gatggtccga atggtttcca ggtgg                                         25

SEQ ID NO: 264          moltype = DNA  length = 25
FEATURE                 Location/Qualifiers
source                  1..25
                        mol_type = other DNA
                        organism = synthetic construct
SEQUENCE: 264
gtttttgtgc tgttactcgg tagag                                         25

SEQ ID NO: 265          moltype = DNA  length = 25
FEATURE                 Location/Qualifiers
source                  1..25
                        mol_type = other DNA
                        organism = synthetic construct
SEQUENCE: 265
gagatgtgag ccttgtgcat gtggg                                         25

SEQ ID NO: 266          moltype = DNA  length = 25
FEATURE                 Location/Qualifiers
source                  1..25
                        mol_type = other DNA
                        organism = synthetic construct
SEQUENCE: 266
tgagatccgt gagatccttc catct                                         25

SEQ ID NO: 267          moltype = DNA  length = 25
FEATURE                 Location/Qualifiers
source                  1..25
                        mol_type = other DNA
                        organism = synthetic construct
SEQUENCE: 267
tattattttc tatgtccgtt gttgt                                         25

SEQ ID NO: 268          moltype = DNA  length = 25
FEATURE                 Location/Qualifiers
source                  1..25
                        mol_type = other DNA
                        organism = synthetic construct
SEQUENCE: 268
tactgggcaa gtgcttgtca agttc                                         25

SEQ ID NO: 269          moltype = DNA  length = 25
FEATURE                 Location/Qualifiers
source                  1..25
                        mol_type = other DNA
                        organism = synthetic construct
SEQUENCE: 269
gaggatgccc caacaaactc atggc                                         25

SEQ ID NO: 270          moltype = DNA  length = 25
FEATURE                 Location/Qualifiers
source                  1..25
                        mol_type = other DNA
                        organism = synthetic construct
SEQUENCE: 270
```

-continued

```
tctgagttgt tggggctaag cctga                                           25

SEQ ID NO: 271          moltype = DNA  length = 25
FEATURE                 Location/Qualifiers
source                  1..25
                        mol_type = other DNA
                        organism = synthetic construct
SEQUENCE: 271
gaaaggtaac aatcttcatt ctaca                                           25

SEQ ID NO: 272          moltype = DNA  length = 25
FEATURE                 Location/Qualifiers
source                  1..25
                        mol_type = other DNA
                        organism = synthetic construct
SEQUENCE: 272
atcgatacag aaaccacgct gccgc                                           25

SEQ ID NO: 273          moltype = DNA  length = 25
FEATURE                 Location/Qualifiers
source                  1..25
                        mol_type = other DNA
                        organism = synthetic construct
SEQUENCE: 273
actcttgagg gttgattatg ctgca                                           25

SEQ ID NO: 274          moltype = DNA  length = 25
FEATURE                 Location/Qualifiers
source                  1..25
                        mol_type = other DNA
                        organism = synthetic construct
SEQUENCE: 274
ccctgagcac cgtgttcatg aatct                                           25

SEQ ID NO: 275          moltype = DNA  length = 25
FEATURE                 Location/Qualifiers
source                  1..25
                        mol_type = other DNA
                        organism = synthetic construct
SEQUENCE: 275
gattgagtca tcgacattca ggatt                                           25

SEQ ID NO: 276          moltype = DNA  length = 25
FEATURE                 Location/Qualifiers
source                  1..25
                        mol_type = other DNA
                        organism = synthetic construct
SEQUENCE: 276
cacccgggac tacttgctgg tgact                                           25

SEQ ID NO: 277          moltype = DNA  length = 25
FEATURE                 Location/Qualifiers
source                  1..25
                        mol_type = other DNA
                        organism = synthetic construct
SEQUENCE: 277
tggagaaaat gacgacccac gacca                                           25

SEQ ID NO: 278          moltype = DNA  length = 25
FEATURE                 Location/Qualifiers
source                  1..25
                        mol_type = other DNA
                        organism = synthetic construct
SEQUENCE: 278
gacagccttt tgccattggt ggctc                                           25

SEQ ID NO: 279          moltype = DNA  length = 25
FEATURE                 Location/Qualifiers
source                  1..25
                        mol_type = other DNA
                        organism = synthetic construct
SEQUENCE: 279
ggcctttcac aactaggact gagaa                                           25

SEQ ID NO: 280          moltype = DNA  length = 25
FEATURE                 Location/Qualifiers
source                  1..25
                        mol_type = other DNA
                        organism = synthetic construct
```

```
SEQUENCE: 280
tatgtaatgt acacctgccc taagg                                         25

SEQ ID NO: 281          moltype = DNA  length = 25
FEATURE                 Location/Qualifiers
source                  1..25
                        mol_type = other DNA
                        organism = synthetic construct
SEQUENCE: 281
gggagagttg accgttttca tcctg                                         25

SEQ ID NO: 282          moltype = DNA  length = 25
FEATURE                 Location/Qualifiers
source                  1..25
                        mol_type = other DNA
                        organism = synthetic construct
SEQUENCE: 282
cataaggcac tgggactcgg atttc                                         25

SEQ ID NO: 283          moltype = DNA  length = 25
FEATURE                 Location/Qualifiers
source                  1..25
                        mol_type = other DNA
                        organism = synthetic construct
SEQUENCE: 283
gcacatctgg gcagttgtac catgc                                         25

SEQ ID NO: 284          moltype = DNA  length = 25
FEATURE                 Location/Qualifiers
source                  1..25
                        mol_type = other DNA
                        organism = synthetic construct
SEQUENCE: 284
cactgacagt gcccagggct ctggg                                         25

SEQ ID NO: 285          moltype = DNA  length = 25
FEATURE                 Location/Qualifiers
source                  1..25
                        mol_type = other DNA
                        organism = synthetic construct
SEQUENCE: 285
gagtgggagc cgtgaatatc tctgt                                         25

SEQ ID NO: 286          moltype = DNA  length = 25
FEATURE                 Location/Qualifiers
source                  1..25
                        mol_type = other DNA
                        organism = synthetic construct
SEQUENCE: 286
aaattatcat actaccggct acatc                                         25

SEQ ID NO: 287          moltype = DNA  length = 25
FEATURE                 Location/Qualifiers
source                  1..25
                        mol_type = other DNA
                        organism = synthetic construct
SEQUENCE: 287
taatttgctt catttccttg ctatt                                         25

SEQ ID NO: 288          moltype = DNA  length = 25
FEATURE                 Location/Qualifiers
source                  1..25
                        mol_type = other DNA
                        organism = synthetic construct
SEQUENCE: 288
aaggtgaatg taccctaacc tgctc                                         25

SEQ ID NO: 289          moltype = DNA  length = 25
FEATURE                 Location/Qualifiers
source                  1..25
                        mol_type = other DNA
                        organism = synthetic construct
SEQUENCE: 289
gagcatcaat cttgttactg ctgat                                         25

SEQ ID NO: 290          moltype = DNA  length = 25
FEATURE                 Location/Qualifiers
source                  1..25
                        mol_type = other DNA
```

```
                        organism = synthetic construct
SEQUENCE: 290
gatccccaag tggtgaatga cacgc                                          25

SEQ ID NO: 291          moltype = DNA  length = 25
FEATURE                 Location/Qualifiers
source                  1..25
                        mol_type = other DNA
                        organism = synthetic construct
SEQUENCE: 291
gttacctact ttgacttttt gcatt                                          25

SEQ ID NO: 292          moltype = DNA  length = 25
FEATURE                 Location/Qualifiers
source                  1..25
                        mol_type = other DNA
                        organism = synthetic construct
SEQUENCE: 292
gaacgggaag gagacgctgc agcgc                                          25

SEQ ID NO: 293          moltype = DNA  length = 25
FEATURE                 Location/Qualifiers
source                  1..25
                        mol_type = other DNA
                        organism = synthetic construct
SEQUENCE: 293
cagactggaa acgggacttt ctatt                                          25

SEQ ID NO: 294          moltype = DNA  length = 25
FEATURE                 Location/Qualifiers
source                  1..25
                        mol_type = other DNA
                        organism = synthetic construct
SEQUENCE: 294
aaccccagag aagtgcttca ttttc                                          25

SEQ ID NO: 295          moltype = DNA  length = 25
FEATURE                 Location/Qualifiers
source                  1..25
                        mol_type = other DNA
                        organism = synthetic construct
SEQUENCE: 295
gacgaggctt ttgagcagct ggtgc                                          25

SEQ ID NO: 296          moltype = DNA  length = 25
FEATURE                 Location/Qualifiers
source                  1..25
                        mol_type = other DNA
                        organism = synthetic construct
SEQUENCE: 296
gcaaaatgcc tttacgttgt tctaa                                          25

SEQ ID NO: 297          moltype = DNA  length = 25
FEATURE                 Location/Qualifiers
source                  1..25
                        mol_type = other DNA
                        organism = synthetic construct
SEQUENCE: 297
gggtctggat cttttctcag agcgt                                          25

SEQ ID NO: 298          moltype = DNA  length = 25
FEATURE                 Location/Qualifiers
source                  1..25
                        mol_type = other DNA
                        organism = synthetic construct
SEQUENCE: 298
ggatttcgtt tgctgtggca ttggt                                          25

SEQ ID NO: 299          moltype = DNA  length = 25
FEATURE                 Location/Qualifiers
source                  1..25
                        mol_type = other DNA
                        organism = synthetic construct
SEQUENCE: 299
aacatctgtg tctttatttt gctgc                                          25

SEQ ID NO: 300          moltype = DNA  length = 25
FEATURE                 Location/Qualifiers
source                  1..25
```

```
                        mol_type = other DNA
                        organism = synthetic construct
SEQUENCE: 300
tccccagtgg tgacctatgt gtgtg                                          25

SEQ ID NO: 301          moltype = DNA  length = 25
FEATURE                 Location/Qualifiers
source                  1..25
                        mol_type = other DNA
                        organism = synthetic construct
SEQUENCE: 301
atgacagttt cacaacctgc attga                                          25

SEQ ID NO: 302          moltype = DNA  length = 25
FEATURE                 Location/Qualifiers
source                  1..25
                        mol_type = other DNA
                        organism = synthetic construct
SEQUENCE: 302
gggaacttac ttctctatag cccac                                          25

SEQ ID NO: 303          moltype = DNA  length = 25
FEATURE                 Location/Qualifiers
source                  1..25
                        mol_type = other DNA
                        organism = synthetic construct
SEQUENCE: 303
gctcctagca cgattatatt tcacc                                          25

SEQ ID NO: 304          moltype = DNA  length = 25
FEATURE                 Location/Qualifiers
source                  1..25
                        mol_type = other DNA
                        organism = synthetic construct
SEQUENCE: 304
cactaactat gcatggtgcc ccagg                                          25

SEQ ID NO: 305          moltype = DNA  length = 25
FEATURE                 Location/Qualifiers
source                  1..25
                        mol_type = other DNA
                        organism = synthetic construct
SEQUENCE: 305
ggcttgctct gggactttta tgctc                                          25

SEQ ID NO: 306          moltype = DNA  length = 25
FEATURE                 Location/Qualifiers
source                  1..25
                        mol_type = other DNA
                        organism = synthetic construct
SEQUENCE: 306
gagaataacc tcatagtacc aacat                                          25

SEQ ID NO: 307          moltype = DNA  length = 25
FEATURE                 Location/Qualifiers
source                  1..25
                        mol_type = other DNA
                        organism = synthetic construct
SEQUENCE: 307
ggctccagaa cgaagatcca cactt                                          25

SEQ ID NO: 308          moltype = DNA  length = 25
FEATURE                 Location/Qualifiers
source                  1..25
                        mol_type = other DNA
                        organism = synthetic construct
SEQUENCE: 308
ggatttttct tatgcactcc tatgc                                          25

SEQ ID NO: 309          moltype = DNA  length = 25
FEATURE                 Location/Qualifiers
source                  1..25
                        mol_type = other DNA
                        organism = synthetic construct
SEQUENCE: 309
aaacatgtac tggcacaatt tgtga                                          25

SEQ ID NO: 310          moltype = DNA  length = 25
FEATURE                 Location/Qualifiers
```

```
source                  1..25
                        mol_type = other DNA
                        organism = synthetic construct
SEQUENCE: 310
aaggcagaca gttttgcttt agtac                                        25

SEQ ID NO: 311          moltype = DNA  length = 25
FEATURE                 Location/Qualifiers
source                  1..25
                        mol_type = other DNA
                        organism = synthetic construct
SEQUENCE: 311
acgggccttt ttcacttaga agctg                                        25

SEQ ID NO: 312          moltype = DNA  length = 25
FEATURE                 Location/Qualifiers
source                  1..25
                        mol_type = other DNA
                        organism = synthetic construct
SEQUENCE: 312
gagtgtctca gaagtgtgct cctct                                        25

SEQ ID NO: 313          moltype = DNA  length = 25
FEATURE                 Location/Qualifiers
source                  1..25
                        mol_type = other DNA
                        organism = synthetic construct
SEQUENCE: 313
gctctgtgct ttccactata cacag                                        25

SEQ ID NO: 314          moltype = DNA  length = 25
FEATURE                 Location/Qualifiers
source                  1..25
                        mol_type = other DNA
                        organism = synthetic construct
SEQUENCE: 314
ggttgaaaca tatctcttat cttac                                        25

SEQ ID NO: 315          moltype = DNA  length = 25
FEATURE                 Location/Qualifiers
source                  1..25
                        mol_type = other DNA
                        organism = synthetic construct
SEQUENCE: 315
tggtacttat cagtgccaag cgtcc                                        25

SEQ ID NO: 316          moltype = DNA  length = 25
FEATURE                 Location/Qualifiers
source                  1..25
                        mol_type = other DNA
                        organism = synthetic construct
SEQUENCE: 316
gtaagagaat tatctgcaac ttgat                                        25

SEQ ID NO: 317          moltype = DNA  length = 25
FEATURE                 Location/Qualifiers
source                  1..25
                        mol_type = other DNA
                        organism = synthetic construct
SEQUENCE: 317
ttcatagtca catcaaggtc atcaa                                        25

SEQ ID NO: 318          moltype = DNA  length = 25
FEATURE                 Location/Qualifiers
source                  1..25
                        mol_type = other DNA
                        organism = synthetic construct
SEQUENCE: 318
ggaactatct gaaatctgct cagag                                        25

SEQ ID NO: 319          moltype = DNA  length = 25
FEATURE                 Location/Qualifiers
source                  1..25
                        mol_type = other DNA
                        organism = synthetic construct
SEQUENCE: 319
gcagttgcca gaccaataaa atacc                                        25

SEQ ID NO: 320          moltype = DNA  length = 25
```

```
FEATURE                Location/Qualifiers
source                 1..25
                       mol_type = other DNA
                       organism = synthetic construct
SEQUENCE: 320
gggagatacc gaagcctact gtggt                                        25

SEQ ID NO: 321         moltype = DNA  length = 25
FEATURE                Location/Qualifiers
source                 1..25
                       mol_type = other DNA
                       organism = synthetic construct
SEQUENCE: 321
tggaagtgta tctcagtcag ccagt                                        25

SEQ ID NO: 322         moltype = DNA  length = 25
FEATURE                Location/Qualifiers
source                 1..25
                       mol_type = other DNA
                       organism = synthetic construct
SEQUENCE: 322
gatctgtaat gttatttcca cttat                                        25

SEQ ID NO: 323         moltype = DNA  length = 25
FEATURE                Location/Qualifiers
source                 1..25
                       mol_type = other DNA
                       organism = synthetic construct
SEQUENCE: 323
ttttctactc tagcctgttc atatg                                        25

SEQ ID NO: 324         moltype = DNA  length = 25
FEATURE                Location/Qualifiers
source                 1..25
                       mol_type = other DNA
                       organism = synthetic construct
SEQUENCE: 324
ggcttcccag ataagcagcc cagga                                        25

SEQ ID NO: 325         moltype = DNA  length = 25
FEATURE                Location/Qualifiers
source                 1..25
                       mol_type = other DNA
                       organism = synthetic construct
SEQUENCE: 325
gtggactaaa cctgagaatc tcgat                                        25

SEQ ID NO: 326         moltype = DNA  length = 25
FEATURE                Location/Qualifiers
source                 1..25
                       mol_type = other DNA
                       organism = synthetic construct
SEQUENCE: 326
gtggtttgac ccaagaccac aacca                                        25

SEQ ID NO: 327         moltype = DNA  length = 25
FEATURE                Location/Qualifiers
source                 1..25
                       mol_type = other DNA
                       organism = synthetic construct
SEQUENCE: 327
ggtgagctca gatagtctct ttctc                                        25

SEQ ID NO: 328         moltype = DNA  length = 25
FEATURE                Location/Qualifiers
source                 1..25
                       mol_type = other DNA
                       organism = synthetic construct
SEQUENCE: 328
tcgtctctaa ccacgcctat taagc                                        25

SEQ ID NO: 329         moltype = DNA  length = 25
FEATURE                Location/Qualifiers
source                 1..25
                       mol_type = other DNA
                       organism = synthetic construct
SEQUENCE: 329
gcataggcag tattttcctg tcagc                                        25
```

```
SEQ ID NO: 330         moltype = DNA  length = 25
FEATURE                Location/Qualifiers
source                 1..25
                       mol_type = other DNA
                       organism = synthetic construct
SEQUENCE: 330
aatgaggact ctctacagga cccga                                        25

SEQ ID NO: 331         moltype = DNA  length = 25
FEATURE                Location/Qualifiers
source                 1..25
                       mol_type = other DNA
                       organism = synthetic construct
SEQUENCE: 331
caagtacagc gagttcttca cgggc                                        25

SEQ ID NO: 332         moltype = DNA  length = 25
FEATURE                Location/Qualifiers
source                 1..25
                       mol_type = other DNA
                       organism = synthetic construct
SEQUENCE: 332
gatgggacgc ataatcatta cctta                                        25

SEQ ID NO: 333         moltype = DNA  length = 25
FEATURE                Location/Qualifiers
source                 1..25
                       mol_type = other DNA
                       organism = synthetic construct
SEQUENCE: 333
cgatcatctt tcctgttcca gagag                                        25

SEQ ID NO: 334         moltype = DNA  length = 25
FEATURE                Location/Qualifiers
source                 1..25
                       mol_type = other DNA
                       organism = synthetic construct
SEQUENCE: 334
gagctccaga gggtccagaa ggtcc                                        25

SEQ ID NO: 335         moltype = DNA  length = 25
FEATURE                Location/Qualifiers
source                 1..25
                       mol_type = other DNA
                       organism = synthetic construct
SEQUENCE: 335
tcagcaacaa ctgcctgggg gacgc                                        25

SEQ ID NO: 336         moltype = DNA  length = 25
FEATURE                Location/Qualifiers
source                 1..25
                       mol_type = other DNA
                       organism = synthetic construct
SEQUENCE: 336
aggggtgata aatgcgttca tgctc                                        25

SEQ ID NO: 337         moltype = DNA  length = 25
FEATURE                Location/Qualifiers
source                 1..25
                       mol_type = other DNA
                       organism = synthetic construct
SEQUENCE: 337
tgcgtagatt cttgaccatg tagta                                        25

SEQ ID NO: 338         moltype = DNA  length = 25
FEATURE                Location/Qualifiers
source                 1..25
                       mol_type = other DNA
                       organism = synthetic construct
SEQUENCE: 338
aagctgtgtt catggccgag accaa                                        25

SEQ ID NO: 339         moltype = DNA  length = 25
FEATURE                Location/Qualifiers
source                 1..25
                       mol_type = other DNA
                       organism = synthetic construct
SEQUENCE: 339
tgttcacggc ggattctttg tttta                                        25
```

```
SEQ ID NO: 340          moltype = DNA  length = 25
FEATURE                 Location/Qualifiers
source                  1..25
                        mol_type = other DNA
                        organism = synthetic construct
SEQUENCE: 340
gaacatcttt gacactctgc agact                                         25

SEQ ID NO: 341          moltype = DNA  length = 25
FEATURE                 Location/Qualifiers
source                  1..25
                        mol_type = other DNA
                        organism = synthetic construct
SEQUENCE: 341
ttcccacggg tgccatgaag tgtgt                                         25

SEQ ID NO: 342          moltype = DNA  length = 25
FEATURE                 Location/Qualifiers
source                  1..25
                        mol_type = other DNA
                        organism = synthetic construct
SEQUENCE: 342
ggtcccacca acagttcaga aacct                                         25

SEQ ID NO: 343          moltype = DNA  length = 25
FEATURE                 Location/Qualifiers
source                  1..25
                        mol_type = other DNA
                        organism = synthetic construct
SEQUENCE: 343
gaggcatcaa agcacctgtc gcctc                                         25

SEQ ID NO: 344          moltype = DNA  length = 25
FEATURE                 Location/Qualifiers
source                  1..25
                        mol_type = other DNA
                        organism = synthetic construct
SEQUENCE: 344
aacattccct tgatctcatc agttc                                         25

SEQ ID NO: 345          moltype = DNA  length = 25
FEATURE                 Location/Qualifiers
source                  1..25
                        mol_type = other DNA
                        organism = synthetic construct
SEQUENCE: 345
caacaacgaa ggacttttct ccctg                                         25

SEQ ID NO: 346          moltype = DNA  length = 25
FEATURE                 Location/Qualifiers
source                  1..25
                        mol_type = other DNA
                        organism = synthetic construct
SEQUENCE: 346
tgtgtagaca ccctcttggg tccaa                                         25

SEQ ID NO: 347          moltype = DNA  length = 25
FEATURE                 Location/Qualifiers
source                  1..25
                        mol_type = other DNA
                        organism = synthetic construct
SEQUENCE: 347
ccacaagaag ccttatccta cgtcc                                         25

SEQ ID NO: 348          moltype = DNA  length = 25
FEATURE                 Location/Qualifiers
source                  1..25
                        mol_type = other DNA
                        organism = synthetic construct
SEQUENCE: 348
tgagtgcaca cactaccaat cgttc                                         25

SEQ ID NO: 349          moltype = DNA  length = 25
FEATURE                 Location/Qualifiers
source                  1..25
                        mol_type = other DNA
                        organism = synthetic construct
SEQUENCE: 349
```

```
gatgcggttc cgctgcgaag atggg                                         25

SEQ ID NO: 350          moltype = DNA  length = 25
FEATURE                 Location/Qualifiers
source                  1..25
                        mol_type = other DNA
                        organism = synthetic construct
SEQUENCE: 350
gtcagtaggg atgtgtgcct ggctg                                         25

SEQ ID NO: 351          moltype = DNA  length = 25
FEATURE                 Location/Qualifiers
source                  1..25
                        mol_type = other DNA
                        organism = synthetic construct
SEQUENCE: 351
ctctctagtt agatatctga cttgg                                         25

SEQ ID NO: 352          moltype = DNA  length = 25
FEATURE                 Location/Qualifiers
source                  1..25
                        mol_type = other DNA
                        organism = synthetic construct
SEQUENCE: 352
acagggccca gttaatggca gagca                                         25

SEQ ID NO: 353          moltype = DNA  length = 25
FEATURE                 Location/Qualifiers
source                  1..25
                        mol_type = other DNA
                        organism = synthetic construct
SEQUENCE: 353
gaagcgatga atttggagac tctgt                                         25

SEQ ID NO: 354          moltype = DNA  length = 25
FEATURE                 Location/Qualifiers
source                  1..25
                        mol_type = other DNA
                        organism = synthetic construct
SEQUENCE: 354
gggtcccaga ggaacgctgg agcca                                         25

SEQ ID NO: 355          moltype = DNA  length = 25
FEATURE                 Location/Qualifiers
source                  1..25
                        mol_type = other DNA
                        organism = synthetic construct
SEQUENCE: 355
ggagcacatg ttactgcttc atttt                                         25

SEQ ID NO: 356          moltype = DNA  length = 25
FEATURE                 Location/Qualifiers
source                  1..25
                        mol_type = other DNA
                        organism = synthetic construct
SEQUENCE: 356
atcattatta ttgctctcca ctgta                                         25

SEQ ID NO: 357          moltype = DNA  length = 25
FEATURE                 Location/Qualifiers
source                  1..25
                        mol_type = other DNA
                        organism = synthetic construct
SEQUENCE: 357
catgggaaga cgaggccctc gggcc                                         25

SEQ ID NO: 358          moltype = DNA  length = 25
FEATURE                 Location/Qualifiers
source                  1..25
                        mol_type = other DNA
                        organism = synthetic construct
SEQUENCE: 358
taccagggac tatctttgct gcaga                                         25

SEQ ID NO: 359          moltype = DNA  length = 25
FEATURE                 Location/Qualifiers
source                  1..25
                        mol_type = other DNA
                        organism = synthetic construct
```

```
SEQUENCE: 359
gtgaggccac agtcattgag gccct                                        25

SEQ ID NO: 360          moltype = DNA  length = 25
FEATURE                 Location/Qualifiers
source                  1..25
                        mol_type = other DNA
                        organism = synthetic construct
SEQUENCE: 360
gagcccactt gcattttcat agttt                                        25

SEQ ID NO: 361          moltype = DNA  length = 25
FEATURE                 Location/Qualifiers
source                  1..25
                        mol_type = other DNA
                        organism = synthetic construct
SEQUENCE: 361
cactgcactg ccattgtctt ttggt                                        25

SEQ ID NO: 362          moltype = DNA  length = 25
FEATURE                 Location/Qualifiers
source                  1..25
                        mol_type = other DNA
                        organism = synthetic construct
SEQUENCE: 362
gatcaaagag ttcgccgcgg gctac                                        25

SEQ ID NO: 363          moltype = DNA  length = 25
FEATURE                 Location/Qualifiers
source                  1..25
                        mol_type = other DNA
                        organism = synthetic construct
SEQUENCE: 363
aagaaaatcc tgagctttcc tgtcc                                        25

SEQ ID NO: 364          moltype = DNA  length = 25
FEATURE                 Location/Qualifiers
source                  1..25
                        mol_type = other DNA
                        organism = synthetic construct
SEQUENCE: 364
gatcgtcgcc cgatcagtgt tttga                                        25

SEQ ID NO: 365          moltype = DNA  length = 25
FEATURE                 Location/Qualifiers
source                  1..25
                        mol_type = other DNA
                        organism = synthetic construct
SEQUENCE: 365
gctaccgagg ctgtgtgttg aggtc                                        25

SEQ ID NO: 366          moltype = DNA  length = 25
FEATURE                 Location/Qualifiers
source                  1..25
                        mol_type = other DNA
                        organism = synthetic construct
SEQUENCE: 366
tatcggccta atcttagccc tgaag                                        25

SEQ ID NO: 367          moltype = DNA  length = 25
FEATURE                 Location/Qualifiers
source                  1..25
                        mol_type = other DNA
                        organism = synthetic construct
SEQUENCE: 367
cgtcgaccaa tgccaggatt cagag                                        25

SEQ ID NO: 368          moltype = DNA  length = 25
FEATURE                 Location/Qualifiers
source                  1..25
                        mol_type = other DNA
                        organism = synthetic construct
SEQUENCE: 368
cagacaagca acccaaactg aaccc                                        25

SEQ ID NO: 369          moltype = DNA  length = 25
FEATURE                 Location/Qualifiers
source                  1..25
                        mol_type = other DNA
```

-continued

```
                        organism = synthetic construct
SEQUENCE: 369
tctccttagt cttctcatag catta                                          25

SEQ ID NO: 370          moltype = DNA  length = 25
FEATURE                 Location/Qualifiers
source                  1..25
                        mol_type = other DNA
                        organism = synthetic construct
SEQUENCE: 370
ttcaccacct gactttgaat ttgtc                                          25

SEQ ID NO: 371          moltype = DNA  length = 25
FEATURE                 Location/Qualifiers
source                  1..25
                        mol_type = other DNA
                        organism = synthetic construct
SEQUENCE: 371
tggtgaatgt ctgttcagct cttct                                          25

SEQ ID NO: 372          moltype = DNA  length = 25
FEATURE                 Location/Qualifiers
source                  1..25
                        mol_type = other DNA
                        organism = synthetic construct
SEQUENCE: 372
ttccctcgtg acagtggtgt gtggt                                          25

SEQ ID NO: 373          moltype = DNA  length = 25
FEATURE                 Location/Qualifiers
source                  1..25
                        mol_type = other DNA
                        organism = synthetic construct
SEQUENCE: 373
gacattctta tgcttctttt acaac                                          25

SEQ ID NO: 374          moltype = DNA  length = 25
FEATURE                 Location/Qualifiers
source                  1..25
                        mol_type = other DNA
                        organism = synthetic construct
SEQUENCE: 374
cccccttcc tacagcaata tgttc                                           25

SEQ ID NO: 375          moltype = DNA  length = 25
FEATURE                 Location/Qualifiers
source                  1..25
                        mol_type = other DNA
                        organism = synthetic construct
SEQUENCE: 375
agacatcaag tcccattatg ccttc                                          25

SEQ ID NO: 376          moltype = DNA  length = 25
FEATURE                 Location/Qualifiers
source                  1..25
                        mol_type = other DNA
                        organism = synthetic construct
SEQUENCE: 376
gaacaagtga ctctgaccag caggc                                          25

SEQ ID NO: 377          moltype = DNA  length = 25
FEATURE                 Location/Qualifiers
source                  1..25
                        mol_type = other DNA
                        organism = synthetic construct
SEQUENCE: 377
gacctggctg aaactcttaa aaaag                                          25

SEQ ID NO: 378          moltype = DNA  length = 25
FEATURE                 Location/Qualifiers
source                  1..25
                        mol_type = other DNA
                        organism = synthetic construct
SEQUENCE: 378
tcttctggag cctgtgtact gcgga                                          25

SEQ ID NO: 379          moltype = DNA  length = 25
FEATURE                 Location/Qualifiers
source                  1..25
```

```
                        mol_type = other DNA
                        organism = synthetic construct
SEQUENCE: 379
gattcccaaa cgtggttaca ttagc                                          25

SEQ ID NO: 380          moltype = DNA  length = 25
FEATURE                 Location/Qualifiers
source                  1..25
                        mol_type = other DNA
                        organism = synthetic construct
SEQUENCE: 380
agcaagctgc cgaaccaaaa gaatt                                          25

SEQ ID NO: 381          moltype = DNA  length = 25
FEATURE                 Location/Qualifiers
source                  1..25
                        mol_type = other DNA
                        organism = synthetic construct
SEQUENCE: 381
ggattctcaa tgtataagtt gcctt                                          25

SEQ ID NO: 382          moltype = DNA  length = 25
FEATURE                 Location/Qualifiers
source                  1..25
                        mol_type = other DNA
                        organism = synthetic construct
SEQUENCE: 382
agctactctc aggctgcagt gtgag                                          25

SEQ ID NO: 383          moltype = DNA  length = 25
FEATURE                 Location/Qualifiers
source                  1..25
                        mol_type = other DNA
                        organism = synthetic construct
SEQUENCE: 383
ttagccttta cctgtgaagt gttac                                          25

SEQ ID NO: 384          moltype = DNA  length = 25
FEATURE                 Location/Qualifiers
source                  1..25
                        mol_type = other DNA
                        organism = synthetic construct
SEQUENCE: 384
gtttgctctg catttttgat gatgg                                          25

SEQ ID NO: 385          moltype = DNA  length = 25
FEATURE                 Location/Qualifiers
source                  1..25
                        mol_type = other DNA
                        organism = synthetic construct
SEQUENCE: 385
ggcctgacgt aattcactcg tttcc                                          25

SEQ ID NO: 386          moltype = DNA  length = 25
FEATURE                 Location/Qualifiers
source                  1..25
                        mol_type = other DNA
                        organism = synthetic construct
SEQUENCE: 386
ctgcctacca tggtctgggg cttga                                          25

SEQ ID NO: 387          moltype = DNA  length = 25
FEATURE                 Location/Qualifiers
source                  1..25
                        mol_type = other DNA
                        organism = synthetic construct
SEQUENCE: 387
tctgccattg cggctgtcat tgcga                                          25

SEQ ID NO: 388          moltype = DNA  length = 25
FEATURE                 Location/Qualifiers
source                  1..25
                        mol_type = other DNA
                        organism = synthetic construct
SEQUENCE: 388
atcagaccct gacgaagcca agttg                                          25

SEQ ID NO: 389          moltype = DNA  length = 25
FEATURE                 Location/Qualifiers
```

-continued

```
source                1..25
                      mol_type = other DNA
                      organism = synthetic construct
SEQUENCE: 389
gaacatgtgt ctatctgctt ttgcc                                         25

SEQ ID NO: 390        moltype = DNA  length = 25
FEATURE               Location/Qualifiers
source                1..25
                      mol_type = other DNA
                      organism = synthetic construct
SEQUENCE: 390
tcagggtgca agctgctggt gaggt                                         25

SEQ ID NO: 391        moltype = DNA  length = 25
FEATURE               Location/Qualifiers
source                1..25
                      mol_type = other DNA
                      organism = synthetic construct
SEQUENCE: 391
ctgcgaggcc agggaagccc tgagt                                         25

SEQ ID NO: 392        moltype = DNA  length = 25
FEATURE               Location/Qualifiers
source                1..25
                      mol_type = other DNA
                      organism = synthetic construct
SEQUENCE: 392
ttgtctctgc agtgattcgg tttct                                         25

SEQ ID NO: 393        moltype = DNA  length = 25
FEATURE               Location/Qualifiers
source                1..25
                      mol_type = other DNA
                      organism = synthetic construct
SEQUENCE: 393
gactggcatt ttacttctgt gtttt                                         25

SEQ ID NO: 394        moltype = DNA  length = 25
FEATURE               Location/Qualifiers
source                1..25
                      mol_type = other DNA
                      organism = synthetic construct
SEQUENCE: 394
atcattgagg ccaggagctc tgccc                                         25

SEQ ID NO: 395        moltype = DNA  length = 25
FEATURE               Location/Qualifiers
source                1..25
                      mol_type = other DNA
                      organism = synthetic construct
SEQUENCE: 395
actggctgcg agtgttcctg agagt                                         25

SEQ ID NO: 396        moltype = DNA  length = 25
FEATURE               Location/Qualifiers
source                1..25
                      mol_type = other DNA
                      organism = synthetic construct
SEQUENCE: 396
gtgaagctga aggggcctgt gtccc                                         25

SEQ ID NO: 397        moltype = DNA  length = 25
FEATURE               Location/Qualifiers
source                1..25
                      mol_type = other DNA
                      organism = synthetic construct
SEQUENCE: 397
tgatcagtgt tgttgctcta ggaag                                         25

SEQ ID NO: 398        moltype = DNA  length = 25
FEATURE               Location/Qualifiers
source                1..25
                      mol_type = other DNA
                      organism = synthetic construct
SEQUENCE: 398
gtgcatgcta gaatttggga caggc                                         25

SEQ ID NO: 399        moltype = DNA  length = 25
```

```
FEATURE                Location/Qualifiers
source                 1..25
                       mol_type = other DNA
                       organism = synthetic construct
SEQUENCE: 399
ctctactctt tgccgaacta tttgt                                        25

SEQ ID NO: 400         moltype = DNA  length = 25
FEATURE                Location/Qualifiers
source                 1..25
                       mol_type = other DNA
                       organism = synthetic construct
SEQUENCE: 400
cgccctttca cttagttcag tgcca                                        25

SEQ ID NO: 401         moltype = DNA  length = 25
FEATURE                Location/Qualifiers
source                 1..25
                       mol_type = other DNA
                       organism = synthetic construct
SEQUENCE: 401
attggtccaa gattccggat cctaa                                        25

SEQ ID NO: 402         moltype = DNA  length = 25
FEATURE                Location/Qualifiers
source                 1..25
                       mol_type = other DNA
                       organism = synthetic construct
SEQUENCE: 402
tgttcgtggt gagctacgcc aagga                                        25

SEQ ID NO: 403         moltype = DNA  length = 25
FEATURE                Location/Qualifiers
source                 1..25
                       mol_type = other DNA
                       organism = synthetic construct
SEQUENCE: 403
cagtattggg tctgcaactc atccg                                        25

SEQ ID NO: 404         moltype = DNA  length = 25
FEATURE                Location/Qualifiers
source                 1..25
                       mol_type = other DNA
                       organism = synthetic construct
SEQUENCE: 404
ctgttctgct tcgaagtatt caata                                        25

SEQ ID NO: 405         moltype = DNA  length = 25
FEATURE                Location/Qualifiers
source                 1..25
                       mol_type = other DNA
                       organism = synthetic construct
SEQUENCE: 405
ttgtatttta caaatctccc tcttc                                        25

SEQ ID NO: 406         moltype = DNA  length = 25
FEATURE                Location/Qualifiers
source                 1..25
                       mol_type = other DNA
                       organism = synthetic construct
SEQUENCE: 406
gtgtcataat tccccgggca agggc                                        25

SEQ ID NO: 407         moltype = DNA  length = 25
FEATURE                Location/Qualifiers
source                 1..25
                       mol_type = other DNA
                       organism = synthetic construct
SEQUENCE: 407
gttgcatttt ccaggctgag agctg                                        25

SEQ ID NO: 408         moltype = DNA  length = 25
FEATURE                Location/Qualifiers
source                 1..25
                       mol_type = other DNA
                       organism = synthetic construct
SEQUENCE: 408
gttgcctgtc agtgtttaca aacta                                        25
```

-continued

```
SEQ ID NO: 409         moltype = DNA  length = 25
FEATURE                Location/Qualifiers
source                 1..25
                       mol_type = other DNA
                       organism = synthetic construct
SEQUENCE: 409
taaaagggcc cacaatgctc caatt                                         25

SEQ ID NO: 410         moltype = DNA  length = 25
FEATURE                Location/Qualifiers
source                 1..25
                       mol_type = other DNA
                       organism = synthetic construct
SEQUENCE: 410
accgttatgc attactctgt gtcta                                         25

SEQ ID NO: 411         moltype = DNA  length = 25
FEATURE                Location/Qualifiers
source                 1..25
                       mol_type = other DNA
                       organism = synthetic construct
SEQUENCE: 411
gtgtctgtgt tccaaccact gaatc                                         25

SEQ ID NO: 412         moltype = DNA  length = 25
FEATURE                Location/Qualifiers
source                 1..25
                       mol_type = other DNA
                       organism = synthetic construct
SEQUENCE: 412
gagctatgat tgcacactgt actct                                         25

SEQ ID NO: 413         moltype = DNA  length = 25
FEATURE                Location/Qualifiers
source                 1..25
                       mol_type = other DNA
                       organism = synthetic construct
SEQUENCE: 413
tagatcgtgg cccttcaatt tagaa                                         25

SEQ ID NO: 414         moltype = DNA  length = 25
FEATURE                Location/Qualifiers
source                 1..25
                       mol_type = other DNA
                       organism = synthetic construct
SEQUENCE: 414
gcaagctctt gtcaaatttt agttt                                         25

SEQ ID NO: 415         moltype = DNA  length = 25
FEATURE                Location/Qualifiers
source                 1..25
                       mol_type = other DNA
                       organism = synthetic construct
SEQUENCE: 415
ggcagctatc ttacagacgc atgaa                                         25

SEQ ID NO: 416         moltype = DNA  length = 25
FEATURE                Location/Qualifiers
source                 1..25
                       mol_type = other DNA
                       organism = synthetic construct
SEQUENCE: 416
gtccagcgaa tgacgtctgt ggcca                                         25

SEQ ID NO: 417         moltype = DNA  length = 25
FEATURE                Location/Qualifiers
source                 1..25
                       mol_type = other DNA
                       organism = synthetic construct
SEQUENCE: 417
agtcaatgag tcgcttgtga attct                                         25

SEQ ID NO: 418         moltype = DNA  length = 25
FEATURE                Location/Qualifiers
source                 1..25
                       mol_type = other DNA
                       organism = synthetic construct
SEQUENCE: 418
gagctgcgac aactggatga acatt                                         25
```

```
SEQ ID NO: 419          moltype = DNA  length = 25
FEATURE                 Location/Qualifiers
source                  1..25
                        mol_type = other DNA
                        organism = synthetic construct
SEQUENCE: 419
tattttggta cctgtgcttg ccaca                                        25

SEQ ID NO: 420          moltype = DNA  length = 25
FEATURE                 Location/Qualifiers
source                  1..25
                        mol_type = other DNA
                        organism = synthetic construct
SEQUENCE: 420
caacacagtt ttcttgtacc ctggg                                        25

SEQ ID NO: 421          moltype = DNA  length = 25
FEATURE                 Location/Qualifiers
source                  1..25
                        mol_type = other DNA
                        organism = synthetic construct
SEQUENCE: 421
tgaggtcaaa ttttatcttt tcact                                        25

SEQ ID NO: 422          moltype = DNA  length = 25
FEATURE                 Location/Qualifiers
source                  1..25
                        mol_type = other DNA
                        organism = synthetic construct
SEQUENCE: 422
tcattacttt ctgcttgacc ggaag                                        25

SEQ ID NO: 423          moltype = DNA  length = 25
FEATURE                 Location/Qualifiers
source                  1..25
                        mol_type = other DNA
                        organism = synthetic construct
SEQUENCE: 423
gagtggatct gcggtgaagc caagc                                        25

SEQ ID NO: 424          moltype = DNA  length = 25
FEATURE                 Location/Qualifiers
source                  1..25
                        mol_type = other DNA
                        organism = synthetic construct
SEQUENCE: 424
caataagtct ttctctccga aaccg                                        25

SEQ ID NO: 425          moltype = DNA  length = 25
FEATURE                 Location/Qualifiers
source                  1..25
                        mol_type = other DNA
                        organism = synthetic construct
SEQUENCE: 425
aatgcgggca tttaagtctg tccat                                        25

SEQ ID NO: 426          moltype = DNA  length = 25
FEATURE                 Location/Qualifiers
source                  1..25
                        mol_type = other DNA
                        organism = synthetic construct
SEQUENCE: 426
aaagccctgg tcgatgttgg agtgg                                        25

SEQ ID NO: 427          moltype = DNA  length = 25
FEATURE                 Location/Qualifiers
source                  1..25
                        mol_type = other DNA
                        organism = synthetic construct
SEQUENCE: 427
agaatgatgt ccccgttgta tgtat                                        25

SEQ ID NO: 428          moltype = DNA  length = 25
FEATURE                 Location/Qualifiers
source                  1..25
                        mol_type = other DNA
                        organism = synthetic construct
SEQUENCE: 428
```

```
tagaaagttt cttccactct ttgac                                        25

SEQ ID NO: 429          moltype = DNA  length = 25
FEATURE                 Location/Qualifiers
source                  1..25
                        mol_type = other DNA
                        organism = synthetic construct
SEQUENCE: 429
ggagacctgg ttgtgtgtgt gtgag                                        25

SEQ ID NO: 430          moltype = DNA  length = 25
FEATURE                 Location/Qualifiers
source                  1..25
                        mol_type = other DNA
                        organism = synthetic construct
SEQUENCE: 430
aagagccacc tgcaagatgg acacg                                        25

SEQ ID NO: 431          moltype = DNA  length = 25
FEATURE                 Location/Qualifiers
source                  1..25
                        mol_type = other DNA
                        organism = synthetic construct
SEQUENCE: 431
tgttcgtggt gagctacgcc aagga                                        25

SEQ ID NO: 432          moltype = DNA  length = 25
FEATURE                 Location/Qualifiers
source                  1..25
                        mol_type = other DNA
                        organism = synthetic construct
SEQUENCE: 432
gaattctaca tactaaatct ctctc                                        25

SEQ ID NO: 433          moltype = DNA  length = 25
FEATURE                 Location/Qualifiers
source                  1..25
                        mol_type = other DNA
                        organism = synthetic construct
SEQUENCE: 433
gatgagcaga cttctcggaa ttcat                                        25

SEQ ID NO: 434          moltype = DNA  length = 25
FEATURE                 Location/Qualifiers
source                  1..25
                        mol_type = other DNA
                        organism = synthetic construct
SEQUENCE: 434
aactaggaca ctaactgggt tccat                                        25

SEQ ID NO: 435          moltype = DNA  length = 25
FEATURE                 Location/Qualifiers
source                  1..25
                        mol_type = other DNA
                        organism = synthetic construct
SEQUENCE: 435
gtcccctgct tgaacactga agggc                                        25

SEQ ID NO: 436          moltype = DNA  length = 25
FEATURE                 Location/Qualifiers
source                  1..25
                        mol_type = other DNA
                        organism = synthetic construct
SEQUENCE: 436
aaatgttgct ctaatcagat tgctt                                        25

SEQ ID NO: 437          moltype = DNA  length = 25
FEATURE                 Location/Qualifiers
source                  1..25
                        mol_type = other DNA
                        organism = synthetic construct
SEQUENCE: 437
gacacctgtg tttcagcatt tggag                                        25

SEQ ID NO: 438          moltype = DNA  length = 25
FEATURE                 Location/Qualifiers
source                  1..25
                        mol_type = other DNA
                        organism = synthetic construct
```

```
SEQUENCE: 438
gacccatgag tggaggaact ttcag                                          25

SEQ ID NO: 439          moltype = DNA  length = 25
FEATURE                 Location/Qualifiers
source                  1..25
                        mol_type = other DNA
                        organism = synthetic construct
SEQUENCE: 439
atgacctgca gaaacagaac tgttc                                          25

SEQ ID NO: 440          moltype = DNA  length = 25
FEATURE                 Location/Qualifiers
source                  1..25
                        mol_type = other DNA
                        organism = synthetic construct
SEQUENCE: 440
gctggcacct tagttgcatg accac                                          25

SEQ ID NO: 441          moltype = DNA  length = 25
FEATURE                 Location/Qualifiers
source                  1..25
                        mol_type = other DNA
                        organism = synthetic construct
SEQUENCE: 441
tctgcccaac tgtcaacctt gacaa                                          25

SEQ ID NO: 442          moltype = DNA  length = 25
FEATURE                 Location/Qualifiers
source                  1..25
                        mol_type = other DNA
                        organism = synthetic construct
SEQUENCE: 442
gttataccat ttaaagctgg cacca                                          25

SEQ ID NO: 443          moltype = DNA  length = 25
FEATURE                 Location/Qualifiers
source                  1..25
                        mol_type = other DNA
                        organism = synthetic construct
SEQUENCE: 443
aaaggtatct gctgcatcga acttt                                          25

SEQ ID NO: 444          moltype = DNA  length = 25
FEATURE                 Location/Qualifiers
source                  1..25
                        mol_type = other DNA
                        organism = synthetic construct
SEQUENCE: 444
ttaagttcat tgacaccacc tccaa                                          25

SEQ ID NO: 445          moltype = DNA  length = 25
FEATURE                 Location/Qualifiers
source                  1..25
                        mol_type = other DNA
                        organism = synthetic construct
SEQUENCE: 445
ctgctctggt ggtgccgaag ggcaa                                          25

SEQ ID NO: 446          moltype = DNA  length = 25
FEATURE                 Location/Qualifiers
source                  1..25
                        mol_type = other DNA
                        organism = synthetic construct
SEQUENCE: 446
gattgactgt caggcatggc tttgt                                          25

SEQ ID NO: 447          moltype = DNA  length = 25
FEATURE                 Location/Qualifiers
source                  1..25
                        mol_type = other DNA
                        organism = synthetic construct
SEQUENCE: 447
ctgatttacc ctacagcttc aggcc                                          25

SEQ ID NO: 448          moltype = DNA  length = 25
FEATURE                 Location/Qualifiers
source                  1..25
                        mol_type = other DNA
```

```
                        organism = synthetic construct
SEQUENCE: 448
tagcttctgg tgttgttcct ttact                                   25

SEQ ID NO: 449          moltype = DNA  length = 25
FEATURE                 Location/Qualifiers
source                  1..25
                        mol_type = other DNA
                        organism = synthetic construct
SEQUENCE: 449
gagctactca cattagatgc atcct                                   25

SEQ ID NO: 450          moltype = DNA  length = 25
FEATURE                 Location/Qualifiers
source                  1..25
                        mol_type = other DNA
                        organism = synthetic construct
SEQUENCE: 450
gaaagttcag ccagaatctt cgtcc                                   25

SEQ ID NO: 451          moltype = DNA  length = 25
FEATURE                 Location/Qualifiers
source                  1..25
                        mol_type = other DNA
                        organism = synthetic construct
SEQUENCE: 451
atacagcagt tcgaaagccg cgtcc                                   25

SEQ ID NO: 452          moltype = DNA  length = 25
FEATURE                 Location/Qualifiers
source                  1..25
                        mol_type = other DNA
                        organism = synthetic construct
SEQUENCE: 452
ttcatctacc tctaccaacg gtgga                                   25

SEQ ID NO: 453          moltype = DNA  length = 25
FEATURE                 Location/Qualifiers
source                  1..25
                        mol_type = other DNA
                        organism = synthetic construct
SEQUENCE: 453
aggaggctcc gttttgcaaa gtgga                                   25

SEQ ID NO: 454          moltype = DNA  length = 25
FEATURE                 Location/Qualifiers
source                  1..25
                        mol_type = other DNA
                        organism = synthetic construct
SEQUENCE: 454
ctcagtagta ggtttctgtt ctatt                                   25

SEQ ID NO: 455          moltype = DNA  length = 25
FEATURE                 Location/Qualifiers
source                  1..25
                        mol_type = other DNA
                        organism = synthetic construct
SEQUENCE: 455
cattacgggt gttgaaggtg tcttc                                   25

SEQ ID NO: 456          moltype = DNA  length = 25
FEATURE                 Location/Qualifiers
source                  1..25
                        mol_type = other DNA
                        organism = synthetic construct
SEQUENCE: 456
ctgctagtct taagaactgc tttct                                   25

SEQ ID NO: 457          moltype = DNA  length = 25
FEATURE                 Location/Qualifiers
source                  1..25
                        mol_type = other DNA
                        organism = synthetic construct
SEQUENCE: 457
ggaaaacggg cagtctgctc tgctg                                   25

SEQ ID NO: 458          moltype = DNA  length = 25
FEATURE                 Location/Qualifiers
source                  1..25
```

```
                        mol_type = other DNA
                        organism = synthetic construct
SEQUENCE: 458
gccgttcagc ctggttagtt ttcta                                           25

SEQ ID NO: 459          moltype = DNA  length = 25
FEATURE                 Location/Qualifiers
source                  1..25
                        mol_type = other DNA
                        organism = synthetic construct
SEQUENCE: 459
gactgtcttg aacatcccaa atgcc                                           25

SEQ ID NO: 460          moltype = DNA  length = 25
FEATURE                 Location/Qualifiers
source                  1..25
                        mol_type = other DNA
                        organism = synthetic construct
SEQUENCE: 460
tcgcccacca accaagtgtt acaag                                           25

SEQ ID NO: 461          moltype = DNA  length = 25
FEATURE                 Location/Qualifiers
source                  1..25
                        mol_type = other DNA
                        organism = synthetic construct
SEQUENCE: 461
cgctttccac agtttgttac ctgca                                           25

SEQ ID NO: 462          moltype = DNA  length = 25
FEATURE                 Location/Qualifiers
source                  1..25
                        mol_type = other DNA
                        organism = synthetic construct
SEQUENCE: 462
ggacaaactg ccagttttgt ttcct                                           25

SEQ ID NO: 463          moltype = DNA  length = 25
FEATURE                 Location/Qualifiers
source                  1..25
                        mol_type = other DNA
                        organism = synthetic construct
SEQUENCE: 463
ctctcagata tggcctctta cagta                                           25

SEQ ID NO: 464          moltype = DNA  length = 25
FEATURE                 Location/Qualifiers
source                  1..25
                        mol_type = other DNA
                        organism = synthetic construct
SEQUENCE: 464
cttaagcaaa atactcccag gtctc                                           25

SEQ ID NO: 465          moltype = DNA  length = 25
FEATURE                 Location/Qualifiers
source                  1..25
                        mol_type = other DNA
                        organism = synthetic construct
SEQUENCE: 465
gcacagctgc ggtgatcgtc atgga                                           25

SEQ ID NO: 466          moltype = DNA  length = 25
FEATURE                 Location/Qualifiers
source                  1..25
                        mol_type = other DNA
                        organism = synthetic construct
SEQUENCE: 466
gtggtatgcc tgccaagaga cgcaa                                           25

SEQ ID NO: 467          moltype = DNA  length = 25
FEATURE                 Location/Qualifiers
source                  1..25
                        mol_type = other DNA
                        organism = synthetic construct
SEQUENCE: 467
tattcttgga ctgtactctt cgcat                                           25

SEQ ID NO: 468          moltype = DNA  length = 25
FEATURE                 Location/Qualifiers
```

-continued

```
source                  1..25
                        mol_type = other DNA
                        organism = synthetic construct
SEQUENCE: 468
gaaatcattg tgtctgcatt ggtca                                         25

SEQ ID NO: 469          moltype = DNA  length = 25
FEATURE                 Location/Qualifiers
source                  1..25
                        mol_type = other DNA
                        organism = synthetic construct
SEQUENCE: 469
gtaggggtta caattcacat tcctt                                         25

SEQ ID NO: 470          moltype = DNA  length = 25
FEATURE                 Location/Qualifiers
source                  1..25
                        mol_type = other DNA
                        organism = synthetic construct
SEQUENCE: 470
ggtctaggag atctgtccct tttag                                         25

SEQ ID NO: 471          moltype = DNA  length = 25
FEATURE                 Location/Qualifiers
source                  1..25
                        mol_type = other DNA
                        organism = synthetic construct
SEQUENCE: 471
ccataccacc actgagatct cattt                                         25

SEQ ID NO: 472          moltype = DNA  length = 25
FEATURE                 Location/Qualifiers
source                  1..25
                        mol_type = other DNA
                        organism = synthetic construct
SEQUENCE: 472
gaagcgaggc acaggcggtg tggac                                         25
```

METHODS FOR TREATING CANCER

SEQUENCE LISTING

The instant application contains a Sequence Listing which has been submitted electronically in XML format and is hereby incorporated by reference in its entirety. Said XML copy, created on Mar. 13, 2024, is named 51167-027003_Sequence_Listing_3_13_24 and is 418,920 bytes in size.

BACKGROUND OF THE DISCLOSURE

Cancer is responsible for about 25% of all deaths in the U.S. and is a major public health problem in many parts of the world. Estimates are that in 2018, 18.1 million new cases of cancer and 9.6 million deaths occur globally.

Stenoparib (also referred to as 2X-121 or E7449) is an orally bioavailable, brain penetrable, potent small molecule inhibitor of poly (ADP-ribose) polymerase (PARP) 1 and PARP2 activity that has been used for treating cancer.

Dovitinib (also referred to as TKI258), a pan-targeted kinase inhibitor (pan-TKI), is an inhibitor of type III-V receptor tyrosine kinases (RTKs) that mediate both endothelial and tumor cell proliferation and survival.

There exists a need for improved methods for treating cancer.

SUMMARY OF THE DISCLOSURE

In one aspect, featured is a method of treating a cancer in a subject in need thereof including administering to the subject a dosing regimen including a first dose and a second dose of a composition including stenoparib or a pharmaceutically acceptable salt thereof or a hydrate thereof per day.

In some embodiments, the dosing regimen includes a dosing cycle including administration of the composition for 28 days±1 to 5 days.

In some embodiments, the dosing regimen includes more than one dosing cycle.

In some embodiments, the dosing regimen includes 2 to 100 dosing cycles.

In some embodiments, the dosing regimen includes 2 to 8 dosing cycles.

In some embodiments, an amount of stenoparib or the pharmaceutically acceptable salt thereof or the hydrate thereof administered in the first dose is less than or equal to an amount of stenoparib or the pharmaceutically acceptable salt thereof or the hydrate thereof administered in the second dose.

In some embodiments, the first dose includes between about 200 mg to about 400 mg of stenoparib or the pharmaceutically acceptable salt thereof or the hydrate thereof (or any dosage between 200 mg and 400 mg).

In some embodiments, the second dose includes between about 400 mg to about 600 mg of stenoparib or the pharmaceutically acceptable salt thereof or the hydrate thereof (or any dosage between 400 mg and 600 mg).

In some embodiments, the first dose includes about 200 mg of stenoparib or the pharmaceutically acceptable salt thereof or the hydrate thereof and the second dose includes about 400 mg of stenoparib or the pharmaceutically acceptable salt thereof or the hydrate thereof.

In some embodiments, the first dose includes about 400 mg of stenoparib or the pharmaceutically acceptable salt thereof or the hydrate thereof and the second dose includes about 400 mg of stenoparib or the pharmaceutically acceptable salt thereof or the hydrate thereof.

In some embodiments, the first dose includes about 400 mg of stenoparib or the pharmaceutically acceptable salt thereof or the hydrate thereof and the second dose includes about 600 mg of stenoparib or the pharmaceutically acceptable salt thereof or the hydrate thereof.

In some embodiments, the second dose is administered to the subject at least 11 to 13 hours after administration of the first dose.

In some embodiments, the cancer is a solid tumor cancer.

In some embodiments, the cancer is an ovarian cancer, a breast cancer, a colon cancer, a pancreatic cancer, or a prostate cancer.

In some embodiments, the cancer is locally advanced or metastatic.

In some embodiments, the cancer includes a BRCA mutation.

In some embodiments, the cancer is an ovarian cancer, and the ovarian cancer is an epithelial ovarian carcinoma. In some embodiments, the epithelial ovarian carcinoma is a high-grade serous epithelial ovarian carcinoma, an endometrioid epithelial ovarian carcinoma, a clear cell epithelial ovarian carcinoma, an epithelial ovarian carcinosarcoma, an undifferentiated epithelial ovarian carcinoma, or an epithelial ovarian carcinoma of mixed histological subtypes.

In some embodiments, the cancer is homologous recombination (HR) deficient.

In some embodiments, the subject is non-responsive to at least one cancer therapy other than stenoparib or a pharmaceutically acceptable salt thereof or a hydrate thereof. In some embodiments, the subject is non-responsive to at least two cancer therapies other than stenoparib or a pharmaceutically acceptable salt thereof or a hydrate thereof. In some embodiments, the at least one cancer therapy comprises a PARP inhibitor.

In some embodiments, the subject is administered the composition orally.

In some embodiments, the composition is formulated as a capsule or a tablet.

In some embodiments, the composition is formulated as a capsule, and each capsule includes about 50 mg, about 100 mg, or about 200 mg of stenoparib or the pharmaceutically acceptable salt thereof or the hydrate thereof (or any dosage between 50 mg and 200 mg).

In some embodiments, the method includes, prior to administration of the composition, determining the responsiveness of the subject to treatment with stenoparib or the pharmaceutically acceptable salt thereof or the hydrate thereof by determining the expression level of one or more biomarkers of sensitivity selected from the biomarkers of Table 1; and/or determining the expression level of one or more biomarkers of resistance selected from the biomarkers of Table 2.

A second aspect features a method of treating a cancer in a subject in need thereof including administering to the subject a dosing regimen including administering a first dose and a second dose of a first composition including stenoparib or a pharmaceutically acceptable salt thereof or a hydrate thereof per day; and administering a dose of a second composition including dovitinib or a pharmaceutically acceptable salt thereof or a hydrate thereof.

In some embodiments, the dosing regimen includes a dosing cycle including 28 days+1 to 5 days.

In some embodiments, the dosing regimen includes more than one dosing cycle.

In some embodiments, the dosing regimen includes 2 to 100 dosing cycles.

In some embodiments, the dosing regimen includes 2 to 8 dosing cycles.

In some embodiments, the method includes administering the first and second doses of the first composition each day of the dosing cycle and administering the second composition on a 5 days on and 2 days off schedule during the dosing cycle.

In some embodiments, the second composition is administered to the subject as a single dose on Days 1-5, Days 8-12, Days 15-19, and Days 22-26 of each dosing cycle.

In some embodiments, an amount of stenoparib or the pharmaceutically acceptable salt thereof or the hydrate thereof administered in the first dose of the first composition is less than or equal to an amount of stenoparib or the pharmaceutically acceptable salt thereof or the hydrate thereof administered in the second dose of the first composition.

In some embodiments, the first dose of the first composition includes between about 200 mg to about 400 mg of stenoparib or the pharmaceutically acceptable salt thereof or the hydrate thereof (or any dosage between 200 mg and 400 mg).

In some embodiments, the second dose of the first composition includes between about 400 mg to about 600 mg of stenoparib or the pharmaceutically acceptable salt thereof or the hydrate thereof (or any dosage between 400 mg and 600 mg).

In some embodiments, the dose of the second composition includes between about 300 mg to about 500 mg of dovitinib or the pharmaceutically acceptable salt thereof or the hydrate thereof (or any dosage between 300 mg and 500 mg).

In some embodiments, the first dose of the first composition includes about 200 mg of stenoparib or the pharmaceutically acceptable salt thereof or the hydrate thereof and the second dose of the first composition includes about 400 mg of stenoparib or the pharmaceutically acceptable salt thereof or the hydrate thereof.

In some embodiments, the first dose of the first composition includes about 400 mg of stenoparib or the pharmaceutically acceptable salt thereof or the hydrate thereof and the second dose of the first composition includes about 400 mg of stenoparib or the pharmaceutically acceptable salt thereof or the hydrate thereof.

In some embodiments, the first dose of the first composition includes about 400 mg of stenoparib or the pharmaceutically acceptable salt thereof or the hydrate thereof and the second dose of the first composition includes about 600 mg of stenoparib or the pharmaceutically acceptable salt thereof or the hydrate thereof.

In some embodiments, the dose of the second composition includes about 300 mg of dovitinib or the pharmaceutically acceptable salt thereof or the hydrate thereof.

In some embodiments, the dose of the second composition includes about 400 mg of dovitinib or the pharmaceutically acceptable salt thereof or the hydrate thereof.

In some embodiments, the dose of the second composition includes about 500 mg of dovitinib or the pharmaceutically acceptable salt thereof or the hydrate thereof.

In some embodiments, the second dose is administered to the subject at least 11 to 13 hours (e.g., 11 hours, 12 hours, or 13 hours, or any time period between 11 and 13 hours) after administration of the first dose.

In some embodiments, the cancer is a solid tumor cancer.

In some embodiments, the cancer is an ovarian cancer, a breast cancer, a colon cancer, a pancreatic cancer, or a prostate cancer.

In some embodiments, the cancer is locally advanced or metastatic.

In some embodiments, the cancer is HR proficient.

In some embodiments, the subject is non-responsive to at least one cancer therapy other than stenoparib or a pharmaceutically acceptable salt thereof or a hydrate thereof and/or dovitinib and or a pharmaceutically acceptable salt thereof.

In some embodiments, the subject is administered the first composition orally.

In some embodiments, the first composition is formulated as a capsule or a tablet.

In some embodiments, the first composition is formulated as a capsule, and wherein each capsule of the first composition includes about 50 mg, about 100 mg, or about 200 mg of stenoparib or the pharmaceutically acceptable salt thereof or the hydrate thereof (or any dosage between 50 mg and 200 mg).

In some embodiments, the subject is administered the second composition orally.

In some embodiments, the second composition is formulated as a tablet.

In some embodiments, each tablet of the second composition includes about 100 mg of dovitinib or the pharmaceutically acceptable salt thereof or the hydrate thereof.

In some embodiments, the method includes, prior to the administration of the first and second compositions: determining the responsiveness of the subject to treatment with stenoparib or a pharmaceutically acceptable salt thereof or a hydrate thereof by determining the expression level of one or more biomarkers of sensitivity selected from the biomarkers of Table 1; and/or determining the expression level of one or more biomarkers of resistance selected from the biomarkers of Table 2; and/or determining the responsiveness of the subject to treatment with dovitinib or a pharmaceutically acceptable salt thereof or a hydrate thereof by: determining the expression level of one or more biomarkers of sensitivity selected from the biomarkers of Table 3; and/or determining the expression level of one or more biomarkers of resistance selected from the biomarkers of Table 4.

DEFINITIONS

As used herein, "a" or "an" means "at least one" or "one or more" unless otherwise indicated. In addition, the singular forms "a", "an", and "the" include plural referents unless the context clearly dictates otherwise.

As used herein, the term "about" means+/−10% of the recited value.

As used herein, by "administration" or "administering" is meant a method of giving a dosage of stenoparib or a pharmaceutically acceptable salt thereof or a hydrate thereof, dovitinib or a pharmaceutically acceptable salt thereof or a hydrate thereof, or another therapeutic agent to a subject. The compounds utilized in the methods described herein can be administered, for example, intravenously, intramuscularly, transdermally, intradermally, intra-arterially, intracranially, subcutaneously, intraorbitally, intraventricularly, intraspinally, intraperitoneally, intranasally, or orally, or by another other route described herein. In particular instances, the compounds and compositions utilized in the methods described herein are administered orally.

The term "stenoparib" or "2X-121" or "E7449," as used herein refers to 8-(isoindolin-2-ylmethyl)-2,9-dihydro-3H-pyridazino [3,4,5-de]quinazolin-3-one or a pharmaceutically acceptable salt thereof or a hydrate thereof. Stenoparib has the following structure:

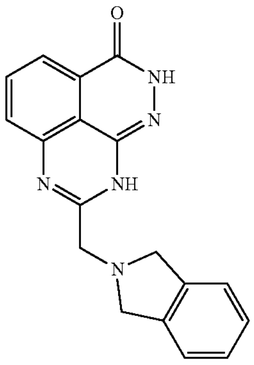 [SMILES: O=c1[nH]nc2c3c(cccc13)N=C(CN1Cc3ccccc3C1)N2]

Stenoparib has a calculated molecular weight of 317.3446 g/mol.

Stenoparib is a small molecule targeted inhibitor of Poly (ADP-ribose) Polymerase (PARP), a key enzyme involved in DNA damage repair in cancer cells. Stenoparib is an orally bioavailable, brain penetrable small molecule PARP inhibitor having novel dual-inhibitory action against both PARP ½ and Tankyrase ½ (important regulators of canonical Wnt/β-catenin, a critical checkpoint in metastases, particularly in triple-negative breast cancer). Stenoparib is not a substrate for P-glycoprotein and is active in P-glycoprotein expressing cells, suggesting that it may overcome PARP inhibitor resistance. Stenoparib was formerly known as E7449 and MGI 25036. Stenoparib is described in McGonigle et al. (Oncotarget 6:41307-41323, 2015) and WO 2009/046205, both of which are hereby incorporated by reference. Examples of pharmaceutically acceptable salts of Stenoparib are described in WO 2009/046205. Stenoparib can be identified by the CAS No. 1140964-99-3. In a particular instance, the form of stenoparib is stenoparib L-tartrate, anhydrous.

As used herein, the term "dovitinib," "TKI-258," or "TKI 258" refers to 4-amino-5-fluoro-3-[6-(4-methylpiperazin-1-yl)-1H-benzimidazol-2-yl]-1H-quinolin-2-one or a pharmaceutically acceptable salt thereof or a hydrate thereof or a tautomer thereof, or a mixture of tautomers thereof. 4-amino-5-fluoro-3-[6-(4-methylpiperazin-1-yl)-1H-benzimidazol-2-yl]-1H-quinolin-2-one has the following structure:

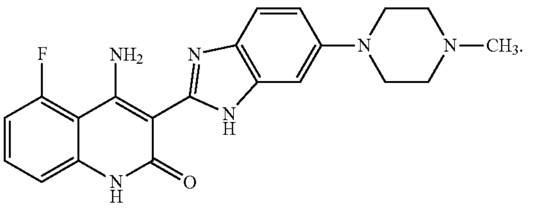 [SMILES: CN1CCN(c2ccc3nc(-c4c(N)c5c(F)cccc5[nH]c4=O)[nH]c3c2)CC1]

Dovitinib is a small molecule targeted inhibitor of multiple protein kinases (e.g., tyrosine receptor kinases (RTKs)). Receptor tyrosine kinases (RTKs) are transmembrane polypeptides that regulate developmental cell growth and differentiation, remodeling and regeneration of adult tissues. Polypeptide ligands known as growth factors or cytokines, are known to activate RTKs. Signaling RTKs involves ligand binding and a shift in conformation in the external domain of the receptor resulting in its dimerization. Binding of the ligand to the RTK results in receptor trans-phosphorylation at specific tyrosine residues and subsequent activation of the catalytic domains for the phosphorylation of cytoplasmic substrates.

Dovitinib, or a pharmaceutically acceptable salt thereof or a hydrate or solvate thereof, exists in a variety of polymorphs. Dovitinib, or a hydrate or solvate thereof, or a polymorph thereof, is useful for inhibiting angiogenesis and treating proliferative diseases. In a particular instance, the form of dovitinib is dovitinib lactate, monohydrate.

The structure and activity of 4-amino-5-fluoro-3-[6-(4-methylpiperazin-1-yl)-1H-benzimidazol-2-yl]-1H-quinolin-2-one or a tautomer thereof is described in WO 2002/022598 and WO 2012/001074, hereby incorporated by reference. Dovitinib can be identified by the CAS No. 405169-16-6. In a particular instance, the form of dovitinib is dovitinib lactate, monohydrate. Dovitinib lactate, monohydrate can be identified by CAS No. 915769-50-5.

As used herein, "dosage form" means a pharmacologically active material in a medium, carrier, vehicle, or device suitable for administration to a subject. A dosage form can include a disclosed composition or a product of a disclosed method of making, in combination with a pharmaceutically acceptable excipient, such as a preservative, buffer, saline, or phosphate buffered saline. Dosage forms can be made using conventional pharmaceutical manufacturing and compounding techniques. Dosage forms can include inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts), antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose), and co-solvents (e.g., glycerol, polyethylene glycol, ethanol). A dosage form may be specially formulated for administration in solid or liquid form, including those adapted for the following: oral administration, for example, drenches (aqueous or non-aqueous solutions or suspensions), tablets and capsules, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation.

As used herein, the term "pharmaceutically acceptable carrier" refers to an excipient or diluent in a pharmaceutical composition. For example, a pharmaceutically acceptable carrier may be a vehicle capable of suspending or dissolving the stenoparib or a pharmaceutically acceptable salt thereof or a hydrate thereof. The pharmaceutically acceptable carrier can be compatible with the other ingredients of the formulation and not deleterious to the recipient. For oral administration, a solid carrier may be preferred.

As used herein, the term "pharmaceutically acceptable salt" refers to salt forms (e.g., acid addition salts or metal salts) of stenoparib or dovitinib suitable for therapeutic use according to the methods of the disclosure.

By "pharmaceutical composition" is meant any composition that contains stenoparib or a pharmaceutically acceptable salt thereof or a hydrate thereof or dovitinib or a pharmaceutically acceptable salt thereof or a hydrate thereof combined with a pharmaceutically acceptable carrier that together is suitable for administration to a subject and that treats a cancer or reduces the severity of, or ameliorates, one or more symptoms associated with a cancer. Pharmaceutical compositions useful in the methods of the disclosure can take the form of tablets, gelcaps, capsules, pills, powders, granulates, suspensions, and/or emulsions. In particular instances, pharmaceutical compositions useful in the methods of the disclosure take the form of capsules.

By "biomarker" is meant a nucleic acid molecule (e.g., an mRNA or its complement, for example, a cDNA) or a protein encoded by the nucleic acid molecule present in, or from, a cell or tissue. The expression of the biomarker correlates to the responsiveness (e.g., sensitivity or resistance) of the cell or tissue (and thus, the subject containing the cell or tissue or the subject from which the cell or tissue was obtained) to a cancer treatment (e.g., stenoparib or a pharmaceutically acceptable salt thereof or a hydrate thereof or dovitinib or a pharmaceutically acceptable salt thereof or a hydrate thereof). In particular, a biomarker of sensitivity for the responsiveness to treatment with stenoparib or a pharmaceutically acceptable salt thereof or a hydrate thereof is a nucleic acid molecule (e.g., a mRNA or its complement) expressed from any one of the genes shown in Table 1, or the protein encoded by the nucleic acid molecule, and a biomarker of resistance for the responsiveness to treatment with stenoparib or a pharmaceutically acceptable salt thereof or a hydrate thereof is a nucleic acid molecule (e.g., a mRNA or its complement) expressed from any one of the genes shown in Table 2, or the protein encoded by the nucleic acid molecule. In particular, a biomarker of sensitivity for the responsiveness to treatment with dovitinib or a pharmaceutically acceptable salt thereof or a hydrate thereof is a nucleic acid molecule (e.g., a mRNA or its complement) expressed from any one of the genes shown in Table 3, or the protein encoded by the nucleic acid molecule, and a biomarker of resistance for the responsiveness to treatment with dovitinib or a pharmaceutically acceptable salt thereof or a hydrate thereof is a nucleic acid molecule (e.g., a mRNA or its complement) expressed from any one of the genes shown in Table 4, or the protein encoded by the nucleic acid molecule.

The terms "cancer" and "cancerous" refer to or describe the physiological condition in mammals (e.g., humans) that is typically characterized by unregulated cell proliferation. Examples of cancer include, but are not limited to, myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. The term cancer includes hematological cancers (e.g., cancer of the blood, such as multiple myeloma) and solid tumors (e.g., breast cancer or ovarian cancer). In a particular example, the cancer is an ovarian cancer, a breast cancer, a colon cancer, a pancreatic cancer, or a prostate cancer. In a particular example, the cancer is locally advanced or metastatic. In a particular example, e.g., when the subject is treated with a monotherapy including stenoparib or a pharmaceutically acceptable salt thereof or a hydrate thereof, the cancer is homologous recombination (HR) deficient. In a particular example, e.g., when the subject is treated with a monotherapy including stenoparib or a pharmaceutically acceptable salt thereof or a hydrate thereof, the cancer includes a BRCA mutation. In a particular example, e.g., when the subject is treated with a combination therapy including stenoparib or a pharmaceutically acceptable salt thereof or a hydrate thereof and dovitinib or a pharmaceutically acceptable salt thereof or a hydrate thereof, the cancer is HR proficient. In a particular example, e.g., when the subject is treated with a monotherapy including stenoparib or a pharmaceutically acceptable salt thereof or a hydrate thereof, the cancer is an ovarian cancer, and the ovarian cancer is an epithelial ovarian carcinoma. In some examples, an ovarian cancer may include a high-grade serous epithelial ovarian carcinoma, an endometrioid epithelial ovarian carcinoma, a clear cell epithelial ovarian carcinoma, an epithelial ovarian carcinosarcoma, an undifferentiated epithelial ovarian carcinoma, or an epithelial ovarian carcinoma of mixed histological subtypes.

The term "BRCA mutation" refers to a mutation in the breast cancer type 1 susceptibility protein (BRCA1) or breast cancer type 2 susceptibility protein (BRCA2) gene. A subject or subject having a BRCA mutation is at higher risk of developing a cancer (e.g., a breast cancer or an ovarian cancer). In some instances, BRCA mutations (e.g., particularly in BRCA2) affect a cell's ability to undergo homologous recombination (HR).

The terms "homologous recombination deficient," "HR deficient," "homologous recombination deficiency," "HR deficiency," and "HRD" refer to deficiencies that occur during homologous recombination (HR), i.e., during meiosis. Deficiencies in homologous recombination is associated with an increased risk of cancer. (e.g., in humans). Decreased rates of homologous recombination may decrease efficiency of DNA repair, which may lead to cancer. In some instances, BRCA mutation may lead to HR deficiency.

The terms "homologous recombination proficient," "HR proficient," "homologous recombination proficiency," and "HR proficiency" refer to proficiency in homologous recombination. Specifically, as applied to cancers and tumors (e.g., of solid tumor cancers), HR proficient cancer cells are able to repair DNA damage through homologous recombination. In particular, HR proficient cancers are difficult to treat because of this ability to repair DNA damage. In some examples, cancer cells or tumors may become resistant to a PARP1 inhibitor (e.g., stenoparib) if the cancer cells or tumors are or become HR proficient, and gain the ability to repair DNA through homologous recombination.

The terms "expression level" and "level of expression," as used herein interchangeably, refer to the amount of a gene product in a cell, tissue, biological sample, organism, or subject, e.g., amounts of DNA, RNA (e.g., messenger RNA (mRNA)), or proteins of a given gene.

"Gene" as used herein indicates a coding or noncoding gene whose activity can be determined by measuring the produced RNA. Examples include protein coding genes, microRNAs, small nuclear RNAs and other RNAs with catalytic, regulatory or coding properties.

To "inhibit growth" as used herein means causing a reduction in cell growth (e.g., cancer cell growth, e.g., as compared to the growth inhibition of the NCI60 cancer cell lines as a reference) in vivo or in vitro by, e.g., 10%, 20%, 30%, 40%, 50%, 60%, 70%, 80%, 90%, 95%, or 99% or more, as evident by a reduction in the proliferation of cells exposed to a treatment (e.g., stenoparib or a pharmaceutically acceptable salt thereof or a hydrate thereof or dovitinib or a pharmaceutically acceptable salt thereof or a hydrate thereof), relative to the proliferation of cells in the absence of the treatment. Growth inhibition may be the result of a treatment (e.g., stenoparib or a pharmaceutically acceptable salt thereof or a hydrate thereof or dovitinib or a pharmaceutically acceptable salt thereof or a hydrate thereof) that induces apoptosis in a cell, induces necrosis in a cell, slows cell cycle progression, disrupts cellular metabolism, induces cell lysis, or induces some other mechanism that reduces the proliferation of cells.

"Microarray" as used herein means a device employed by any method that quantifies one or more subject oligonucleotides, e.g., RNA, DNA, cDNA, or analogues thereof, at a time. For example, many DNA microarrays, including those made by Affymetrix (e.g., an Affymetrix HG-U133A array), use several probes for determining the expression of a single gene. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors.

As used herein, the term "percent (%) sequence identity" refers to the percentage of nucleic acid residues of a candidate sequence, e.g., a probe or primer described herein, that are identical to the nucleic acid residues of a reference sequence, e.g., a biomarker sequence described herein, after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using computer software, such as BLAST, BLAST-2, BLAST-P, BLAST-N, BLAST-X, WU-BLAST-2, ALIGN, ALIGN-2, CLUSTAL, Megalign (DNASTAR). In addition, those skilled in the art can determine appropriate parameters for measuring alignment, including any algorithms needed to achieve optimal alignment over the length of the sequences being compared.

"NCI60" as used herein means a panel of 60 cancer cell lines from lung, colon, breast, ovarian, leukemia, renal, melanoma, prostate and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COLO205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

The terms "patient" and "subject," as used interchangeably herein, refer to any animal (e.g., a mammal, such as a human). A subject to be treated or tested for responsiveness to a treatment (e.g., dovitinib or a pharmaceutically acceptable salt thereof or a hydrate thereof) according to the methods described herein may be one who has been diagnosed with a cancer, such as ovarian cancer or breast cancer. Diagnosis may be performed by any method or techniques known in the art, such as x-ray, MRI, or biopsy, and confirmed by a physician. To minimize exposure of a subject to drug treatments that may not be therapeutic, the subject may be determined to be either responsive or non-responsive to a cancer treatment, such as stenoparib or a pharmaceutically acceptable salt thereof or a hydrate thereof or dovitinib or a pharmaceutically acceptable salt thereof or a hydrate thereof, according to the methods described herein.

"Resistance," as used herein, refers to the likelihood that a cancer treatment (e.g., stenoparib or a pharmaceutically acceptable salt thereof or a hydrate thereof or dovitinib or a pharmaceutically acceptable salt thereof or a hydrate thereof) does not have (e.g., does not induce) a desired anti-cancer effect (or, alternatively, refers to the inability of a desired effect to be caused or induced by the cancer treatment in a cell (e.g., a cancer cell) or a tissue (e.g., a tumor) in vitro or in vivo (e.g., in a subject with a cancer, such as a human). For example, resistance refers to the likelihood that a cell (e.g., a cancer cell) or a tissue (e.g., a tumor) in vitro or in vivo (e.g., in a subject with a cancer, such as a human) is tolerant to treatment with an anti-cancer agent (e.g., stenoparib or a pharmaceutically acceptable salt thereof or a hydrate thereof or dovitinib or a pharmaceutically acceptable salt thereof or a hydrate thereof), e.g., the cell or tissue is able to survive and grow despite exposure to (e.g., treatment with) an anti-cancer agent (e.g., stenoparib or a pharmaceutically acceptable salt thereof or a hydrate thereof or dovitinib or a pharmaceutically acceptable salt thereof or a hydrate thereof). For example, a resistant cell or tissue is one that, upon exposure of the cell (e.g., a cancer cell) or the tissue (e.g., a tumor), respectively, to a cancer therapeutic (e.g., stenoparib or a pharmaceutically acceptable salt thereof or a hydrate thereof or dovitinib or a pharmaceutically acceptable salt thereof or a hydrate thereof) exhibits an inhibition in growth of the cell or tumor of less than 30%, 25%, 20%, 15%, 10%, 5%, or 1% relative to the growth of a cell or tissue not exposed to the treatment. Resistance to treatment may be determined by a cell proliferation assay, e.g., a cell-based assay, which measures the growth of treated cells as a function of the absorbance of the cells of an incident light beam, such as the NCI60 assays described herein. In this assay, greater absorbance indicates greater cell growth, and thus, resistance to the treatment.

The terms "sensitivity" and "responsiveness," as used herein, refer to the likelihood that a cancer treatment (e.g., stenoparib or a pharmaceutically acceptable salt thereof or a hydrate thereof or dovitinib or a pharmaceutically acceptable salt thereof or a hydrate thereof) has (e.g., induces) a desired effect, or alternatively refers to the strength of a desired effect caused or induced by the treatment in a cell (e.g., a cancer cell) or a tissue (e.g., a tumor) in vitro or in vivo (e.g., in a subject with a cancer, such as a human). For example, the desired effect can include inhibition of the growth of a cell (e.g., a cancer cell) in vitro by more than 30%, 35%, 40%, 45%, 50%, 55%, 60%, 65%, 70%, 75%, 80%, 85%, 90%, 95%, or 100% relative to the growth of a cell (e.g., a cancer cell) not exposed to the treatment. The desired effect can also include reduction in tumor mass by, e.g., about 30%, 35%, 40%, 45%, 50%, 55%, 60%, 65%, 70%, 75%, 80%, 85%, 90%, 95%, or 100%. "Sensitive" and "responsive" as used herein refer to a cell (e.g., a cancer cell) or a tissue (e.g., a tumor) in vitro or in vivo (e.g., in a subject with a cancer, such as a human) that is responsive to exposure to a therapeutic (e.g., stenoparib or a pharmaceutically acceptable salt thereof or a hydrate thereof or dovitinib or a pharmaceutically acceptable salt thereof or a hydrate thereof). Responsiveness to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity or responsiveness to the treatment. A greater reduction in growth indicates more sensitivity or responsiveness to the treatment. In some instances, a response exhibited by a subject after treatment with any of the methods described herein may be determined using the Response Evaluation Criteria in Solid Tumors (RECIST) 1.1. In some instances, a response exhibited by a subject after treatment with any of the methods described herein may be a complete response (CR), a partial response (PR), stable disease (SD), or SD for at least 16 weeks.

The term "sample," as used herein, refers to any specimen (such as cells, tissue (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy of the cancer tissue). Biopsy may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve amplification, e.g., using PCR (e.g., RT-PCR). The standard methods of sample purification, such as removal of unwanted molecules, are known in the art.

"Substantially similar" or "corresponds," as used herein with respect to a numerical value of a parameter of one or more of the biomarker(s) of sensitivity and/or resistance (e.g., biomarker expression level, difference score, or mean score), e.g., as determined in a test sample (e.g., a tumor biopsy) from a cancer subject, means that the numerical value of the parameter in the test sample is +0-30% of the numerical value of the parameter in a reference sample (e.g., a cell (e.g., a cancer cell) or tissue (e.g., a tumor) known to be sensitive or resistant to stenoparib or a pharmaceutically acceptable salt thereof or a hydrate thereof or dovitinib or a pharmaceutically acceptable salt thereof or a hydrate thereof). For example, a numerical value of a parameter in a test sample may be substantially similar to, or may correspond to, the numerical value of the parameter in a reference sample if the parameter values of the test and reference samples differ by, e.g., less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

"Substantially dissimilar," as used herein with respect to a numerical value of a parameter of one or more of the biomarker(s) of sensitivity and/or resistance (e.g., biomarker expression level, difference score, or mean score), e.g., as determined in a test sample (e.g., a tumor biopsy) from a cancer subject, means that the numerical value of the parameter in the test sample deviates by greater than 30% from the numerical value of the parameter in a reference sample (e.g., a cell (e.g., a cancer cell) or tissue (e.g., a tumor) known to be sensitive or resistant to stenoparib or a pharmaceutically acceptable salt thereof or a hydrate thereof or dovitinib or a pharmaceutically acceptable salt thereof or a hydrate thereof). For example, a numerical value of a parameter in a test sample may be substantially dissimilar to the numerical value of the parameter in a reference sample if the parameter values of the test and reference samples differ by, e.g., greater than 35%, 40%, 45%, 50%, 55%, 60%, 65%, 70%, 75%, 80%, 85%, 90%, 95%, 100% or more.

"Treatment," "medical treatment," to "treat," and "therapy," as used interchangeably herein, refer to administering or exposing a subject with a cancer (e.g., a human), a cancer cell, or a tumor to an anti-cancer agent (e.g., a drug, a protein, an antibody, a nucleic acid, a chemotherapeutic agent, or a radioactive agent; e.g., stenoparib or a pharmaceutically acceptable salt thereof or a hydrate thereof or dovitinib or a pharmaceutically acceptable salt thereof or a hydrate thereof), or to some other form of medical intervention used to treat or prevent a disease, disorder, or condition (e.g., surgery, cryotherapy, radiation therapy, or combinations thereof). In particular, a medical treatment can include stenoparib or a pharmaceutically acceptable salt thereof or a hydrate thereof or dovitinib or a pharmaceutically acceptable salt thereof or a hydrate thereof. For example, the cancer to be treated is a hematological cancer or a solid tumor. Examples of cancer include, e.g., myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, endometrial cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. Radiation therapy includes the administration of a radioactive agent to a subject or exposure of a subject to radiation. The radiation may be generated from sources such as particle accelerators and related medical devices or agents that emit, e.g., X-radiation, gamma radiation, or electron (Beta radiation) beams. A treatment may be or further include surgery, e.g., to remove a tumor from a subject or living organism.

A "CA125 test" as used herein refers to a test for determining the amount of protein CA125 (cancer antigen 125) in the blood. In some instances, this test may be used to monitor a cancer in a subject during and/or after the subject receives a treatment. In some instances, a CA125 test may be used to monitor the status of an ovarian cancer in a subject. CA125 may also be known as MUC-16.

Other features and advantages of the invention will be apparent from the following Detailed Description, the drawings, and the claims.

BRIEF DESCRIPTION OF THE DRAWINGS

FIG. 6A shows a stripchart of DRP scores in individual response categories in QD dosed patients. FIG. 6B. shows a stripchart of DRP scores in individual response categories in BID dosed patients.

DETAILED DESCRIPTION

Figure 1A:
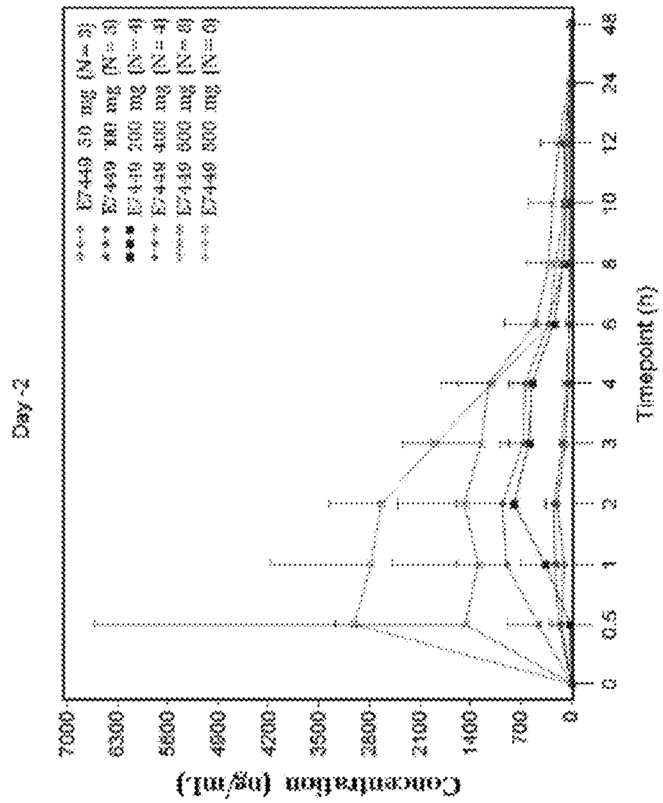
FIG. 1A and FIG. 1B are graphs showing the pharmacokinetics of stenoparib administration. The different lines represent different doses of stenoparib (E7449) administered at time 0. Concentration of stenoparib in blood plasma is shown in ng/ml. In comparing Day-2 administration (FIG. 1A) and Day 15 administration (FIG. 1B), minimal accumulation based on AUC was observed.

The disclosure features methods for treating a cancer, such as a solid tumor cancer, including, for example, ovarian cancer or breast cancer. The methods include administering stenoparib or a pharmaceutically acceptable salt thereof or a hydrate thereof (e.g., twice a day (i.e., BID dosing)) and/or dovitinib or a pharmaceutically acceptable salt thereof or a hydrate thereof (e.g., once a day (i.e., QD dosing) to a subject having a cancer.

The disclosure features twice-a-day dosing (BID dosing) of stenoparib for the treatment of cancer (e.g., solid tumor cancer, such as prostate cancer, breast cancer, and ovarian cancer), which, unexpectedly, produces improved therapeutic outcomes. The inventors observed that subjects with ovarian cancer who were treated with once-a-day dosing of stenoparib did not exhibit an expected therapeutic benefit that was predicted from in vitro studies and in vivo animal studies. In particular, it was discovered that, in human subjects, the half-life of stenoparib was unexpectedly only about 8 hours, which was insufficient to impact the biological and pathological features of the cancer or to improve the survival of the treated subjects. By contrast, twice-a-day dosing of stenoparib increases the length of time a subject is exposed to pharmacokinetically effective concentrations of stenoparib, thereby resulting in improved therapeutic outcomes.

Stenoparib or a pharmaceutically acceptable salt thereof or a hydrate thereof may be administered alone or in combination with dovitinib or a pharmaceutically acceptable salt thereof or a hydrate thereof, and optionally, with another therapeutic agent, in order to treat a cancer in a subject.

In some instances, a subject being treated with a method described herein may have a hematological cancer or a solid tumor, such as a cancer type selected from myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the subject is, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia-chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN). The subject may have estrogen receptor-positive (ER pos) breast cancer. The subject may also have a locally advanced or metastatic form of a cancer. The subject may also have recurrence of cancer, such as a recurrent form of any of the above cancer types, e.g., recurrent breast cancer, recurrent ovarian cancer, or recurrent pancreatic cancer. In a particular example, the cancer is a solid tumor cancer. In a particular example, the cancer is an ovarian cancer, a breast cancer, a colon cancer, a pancreatic cancer, or a prostate cancer. In a particular example, the cancer is locally advanced or metastatic. In a particular example, e.g., when the subject is treated with a monotherapy including stenoparib or a pharmaceutically acceptable salt thereof or a hydrate thereof, the cancer is homologous recombination (HR) deficient. In a particular example, e.g., when the subject is treated with a monotherapy including stenoparib or a pharmaceutically acceptable salt thereof or a hydrate thereof, the cancer includes a BRCA mutation. In a particular example, the ovarian cancer is an epithelial ovarian carcinoma. In some examples, an ovarian cancer is a high-grade serous, endometrioid, clear cell, carcinosarcoma, or undifferentiated ovarian cancer, or an ovarian cancer of mixed histological subtypes. In some examples, an ovarian cancer is a high-grade serous, endometrioid, clear cell, carcinosarcoma, or undifferentiated ovarian cancer, or an ovarian cancer of mixed histological subtypes independent of BRCA1 and HRD status. In a particular example, the ovarian cancer is advanced, refractory, or recurrent ovarian cancer. In a particular example, the ovarian cancer is refractory to or has recurred after treatment with two or more previous chemotherapies and/or antibody therapies. In a particular example, the previous chemotherapies and/or antibody therapies comprise another Poly (ADP-ribose) Polymerase (PARP) inhibitor (PARPi). In a particular example, e.g., when the subject is treated with a combination therapy including stenoparib or a pharmaceutically acceptable salt thereof or a hydrate thereof and dovitinib or a pharmaceutically acceptable salt thereof or a hydrate thereof, the cancer is HR proficient.

Administration of Stenoparib Monotherapy

The disclosure features methods for treating a subject having a cancer by administering stenoparib monotherapy. In particular, the disclosure features a method of treating a cancer in a subject in need thereof including administering to the subject a dosing regimen including a first dose and a second dose of a composition including stenoparib or a pharmaceutically acceptable salt thereof or a hydrate thereof per day.

The dosing regimen, e.g., for stenoparib monotherapy, includes a dosing cycle including administration of the composition for 28 days±1 to 5 days (e.g., 23 days, 24 days, 25 days, 26 days, 27 days, 28 days, 29 days, 30 days, 31 days, 32 days, or 33 days). In some instances, the dosing cycle may be 21 days. In a particular instance, the dosing cycle may be 28 days in length. Stenoparib or a pharmaceutically acceptable salt thereof or a hydrate thereof may be administered daily, including a first dose and a second dose, e.g., as a twice-a-day or BID dosing. The dosing regimen may include more than one dosing cycle. For example, the dosing regimen may include 2 to 100 dosing cycles (e.g., 2 to 3, 2 to 4, 2 to 5, 2 to 6, 2 to 7, 2 to 8, 2 to 9, 2 to 10, 2 to 15, 2 to 20, 2 to 25, 2 to 30, 2 to 40, 2 to 50, 2 to 60, 2 to 70, 2 to 80, 2 to 90, 5 to 10, 10 to 20, 20 to 30, 30 to 50, 50 to 70, or 70 to 100 dosing cycles; e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 dosing cycles). In a particular example, the dosing regimen includes 2 to 8 dosing cycles (e.g., 2, 3, 4, 5, 6, 7, or 8 dosing cycles).

In some instances, an amount of stenoparib or the pharmaceutically acceptable salt thereof or the hydrate thereof administered in the first dose is less than or equal to an amount of stenoparib or the pharmaceutically acceptable salt thereof or the hydrate thereof administered in the second dose. In some instances, the first dose includes between about 200 mg to about 400 mg (e.g., about 200 mg to about 250 mg, about 250 mg to about 300 mg, about 350 mg to about 400 mg, about 200 mg to about 300 mg, or about 300 mg to about 400 mg; e.g., about 200 mg, about 250 mg, about 300 mg, about 350 mg, or about 400 mg) of stenoparib or the pharmaceutically acceptable salt thereof or the hydrate thereof. In some instances, the second dose includes between about 400 mg to about 600 mg (e.g., about 400 mg to about 450 mg, about 450 mg to about 500 mg, about 550 mg to about 600 mg, about 400 mg to about 500 mg, or about 500 mg to about 600 mg; e.g., about 400 mg, about 450 mg, about 500 mg, about 550 mg, or about 600 mg) of stenoparib or the pharmaceutically acceptable salt thereof or the hydrate thereof. In one particular example, the first dose includes about 200 mg of stenoparib or the pharmaceutically acceptable salt thereof or the hydrate thereof and the second dose includes about 400 mg of stenoparib or the pharmaceutically acceptable salt thereof or the hydrate thereof. In another particular example, the first dose includes about 400 mg of stenoparib or the pharmaceutically acceptable salt thereof or the hydrate thereof and the second dose includes about 400 mg of stenoparib or the pharmaceutically acceptable salt thereof or the hydrate thereof. In yet another particular example, the first dose includes about 400 mg of stenoparib or the pharmaceutically acceptable salt thereof or the hydrate thereof and the second dose includes about 600 mg of stenoparib or the pharmaceutically acceptable salt thereof or the hydrate thereof.

In some instances, the second dose is administered to the subject at least 11 to 13 hours (e.g., at least 11, at least 11.5, at least 12, at least 12.5, or at least 13 hours) after administration of the first dose. In some instances, the second dose is administered to the subject at least 6, 7, 8, 9, 10, 11, 12, 13, 14, 15, 16, 17 or 18 hours after administration of the first dose.

In some instances, the first dose and the second dose of the composition is administered to the subject at about the same time during each day of a dosing cycle. For example, if stenoparib or a pharmaceutically acceptable salt thereof or a hydrate thereof is administered to a subject as a first dose at about 8 am and as a second dose at about 8 pm on Day 1 of a first dosing cycle, then stenoparib or the pharmaceutically acceptable salt thereof or the hydrate thereof is administered as a first dose at about 8 am and as a second dose at about 8 pm on Days 2-28 of the first dosing cycle, and optionally also as a first dose at about 8 am and as a second dose at about 8 pm on Days 1-28 of any additional dosing cycles.

In some instances, the subject being administered stenoparib monotherapy is non-responsive to at least one cancer therapy (e.g., one, two, three, four, five, six, seven, eight, nine, ten, or more different cancer therapies) other than stenoparib or a pharmaceutically acceptable salt thereof or a hydrate thereof. In a particular instance, the cancer therapy a PARP inhibitor (PARPi) other than stenoparib.

In some instances, the method includes, prior to administration of the composition, determining the responsiveness of the subject to treatment with stenoparib or the pharmaceutically acceptable salt thereof or the hydrate thereof by determining the expression level of one or more (e.g., five, ten, fifteen, or twenty or more) biomarkers of sensitivity selected from the biomarkers of Table 1; and/or determining the expression level of one or more (e.g., five, ten, fifteen, or twenty or more) biomarkers of resistance selected from the biomarkers of Table 2. Methods of determining the responsiveness of a subject to treatment with stenoparib or a pharmaceutically acceptable salt thereof or a hydrate thereof are described in detail below. In addition, see the methods for determining sensitivity and resistance to stenoparib described in PCT Patent Publication No. WO 2019/219759A1 and U.S. Patent Publication No. US 20210/222252A1, each of which is incorporated by reference in its entirety.

In some instances, a subject treated with stenoparib monotherapy according to any of the methods disclosed herein exhibits a complete response (CR). In some instances, a subject treated with stenoparib monotherapy according to any of the methods disclosed herein exhibits a partial response (PR). In some instances, a subject treated with stenoparib monotherapy according to any of the methods disclosed herein exhibits stable disease (SD). In some instances, a subject treated with stenoparib monotherapy according to any of the methods disclosed herein exhibits SD for at least 16 weeks.

In the methods described herein, stenoparib or a pharmaceutically acceptable salt thereof or a hydrate thereof is administered twice a day (i.e., BID dosing).

The route for administration of stenoparib or a pharmaceutically acceptable salt thereof or a hydrate thereof may be oral. Stenoparib or a pharmaceutically acceptable salt thereof or a hydrate thereof may be administered as a pharmaceutical composition (e.g., including stenoparib or a pharmaceutically acceptable salt thereof or a hydrate thereof in combination with a pharmaceutically acceptable carrier and/or excipient). The pharmaceutical composition may be formulated as a capsule (e.g., a hard gel capsule) or a tablet (e.g., a film coated tablet). Each capsule or tablet of stenoparib or a pharmaceutically acceptable salt thereof or a hydrate thereof may contain about 50 mg, 100 mg, 150 mg, 200 mg, 250 mg, 300 mg, 350 mg, 400 mg, 450 mg, 500 mg, 550 mg, or 600 mg of stenoparib or the pharmaceutically acceptable salt thereof or the hydrate thereof. In a preferred example, each capsule of stenoparib or the pharmaceutically acceptable salt thereof or the hydrate thereof may contain about 50 mg (e.g., 50±5 mg), about 100 mg (e.g., 100±10 mg), about 150 mg (e.g., 150±15 mg), or about 200 mg (e.g., 200±20 mg) of stenoparib or pharmaceutically acceptable salt thereof.

As an example, when stenoparib is formulated in a tablet or capsule in an amount of about 100 mg (e.g., 100 mg±10 mg), administration of a first dose of about 200 mg (e.g., 200 mg±20 mg) or about 400 mg (e.g., 400 mg±40 mg) of stenoparib involves administering (e.g., orally administering) 2 or 4 of the tablets or capsules comprising stenoparib or a pharmaceutically acceptable salt thereof or a hydrate thereof, respectively. Similarly, administration of the second daily dose of stenoparib of about 400 mg (e.g., 400 mg±40 mg) or 600 mg (e.g., 600 mg±60 mg) involves administering (e.g., orally administering) 4 or 6 of the tablets or capsules comprising stenoparib or a pharmaceutically acceptable salt thereof or a hydrate thereof, respectively. As an alternative example, when stenoparib is formulated in a tablet or capsule in an amount of about 200 mg (e.g., 200 mg±10 mg), administration of a first dose of about 200 mg (e.g., 200 mg±20 mg) or about 400 mg (e.g., 400 mg±40 mg) of stenoparib involves administering (e.g., orally administering) 1 or 2 of the tablets or capsules comprising stenoparib or a pharmaceutically acceptable salt thereof or a hydrate thereof, respectively. Similarly, administration of the second daily dose of stenoparib of about 400 mg (e.g., 400 mg±40 mg) or 600 mg (e.g., 600 mg±60 mg) involves administering (e.g., orally administering) 2 or 3 of the tablets or capsules comprising stenoparib or a pharmaceutically acceptable salt thereof or a hydrate thereof, respectively.

The tablets or capsules can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Administration of Stenoparib and Dovitinib Combination Therapy

The disclosure features methods for treating a subject having a cancer by administering a combination therapy including stenoparib, or a pharmaceutically acceptable salt thereof, and dovitinib, or a pharmaceutically acceptable salt thereof. In particular, the disclosure features a method of treating a cancer in a subject in need thereof by administering to the subject a dosing regimen that includes a first dose and a second dose of a first composition including stenoparib or a pharmaceutically acceptable salt thereof or a hydrate thereof per day (e.g., BID dosing); and administering a dose of a second composition including dovitinib or a pharmaceutically acceptable salt thereof or a hydrate thereof.

The combination of stenoparib and dovitinib provides effective anti-tumor therapy (e.g., in treating solid tumors, such as ovarian and breast cancers). Stenoparib is a small molecule, dual-targeted inhibitor of Poly ADP-Ribose Polymerases (PARP 1 and 2) and tankyrase 1 and 2, and functions by limiting the ability of cancer cells within tumors to repair single stranded DNA breaks, which in turn makes the cancer cells more vulnerable to death (apoptosis). Dovitinib is a pan-tyrosine kinase inhibitor (pan-TKI), and its mechanisms of action (MOA) works in part to block the formation of new blood vessels that supply a tumor with nutrients and oxygen (anti-angiogenesis). As these combined MOAs serve to promote cancer cell vulnerability and restrict blood flow necessary to fuel cancer growth and repair, the combination of stenoparib and dovitinib may cause synthetic lethality, thereby increasing the chances of cancer cell death and providing synergistic, enhanced anti-tumor activity. Furthermore, administration of dovitinib may change a homologous recombination (HR)-proficient tumor into an HR-deficient tumor via down-regulation of HR, thus rendering the tumor more susceptible to treatment with stenoparib.

The dosing regimen, e.g., for a stenoparib and dovitinib combination therapy, includes a dosing cycle of 28 days±1 to 5 days (e.g., 23 days, 24 days, 25 days, 26 days, 27 days, 28 days, 29 days, 30 days, 31 days, 32 days, or 33 days). In some instances, the dosing cycle may be 21 days. In a particular instance, the dosing cycle may be 28 days in length. The dosing regimen may include more than one dosing cycle. For example, the dosing regimen may include 2 to 100 dosing cycles (e.g., 2 to 3, 2 to 4, 2 to 5, 2 to 6, 2 to 7, 2 to 8, 2 to 9, 2 to 10, 2 to 15, 2 to 20, 2 to 25, 2 to 30, 2 to 40, 2 to 50, 2 to 60, 2 to 70, 2 to 80, 2 to 90, 5 to 10, 10 to 20, 20 to 30, 30 to 50, 50 to 70, or 70 to 100 dosing cycles; e.g., 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 dosing cycles).

In some instances, the method, e.g., for a stenoparib and dovitinib combination therapy, includes administering first and second doses of the first composition (containing stenoparib or a pharmaceutically acceptable salt thereof or a hydrate thereof) each day of the dosing cycle and administering the second composition (containing dovitinib or a pharmaceutically acceptable salt thereof or a hydrate thereof) on a 5 days on and 2 days off schedule during the dosing cycle. In a particular example, the second composition is administered to the subject as a single dose on Days 1-5, Days 8-12, Days 15-19, and Days 22-26 of each said dosing cycle (e.g., of each said 28-day dosing cycle).

In some instances, an amount of stenoparib or the pharmaceutically acceptable salt thereof or the hydrate thereof administered in the first dose of the first composition is less than or equal to an amount of stenoparib or the pharmaceutically acceptable salt thereof or the hydrate thereof administered in the second dose of the first composition. In some instances, the first dose includes between about 200 mg to about 400 mg (e.g., about 200 mg to about 250 mg, about 250 mg to about 300 mg, about 350 mg to about 400 mg, about 200 mg to about 300 mg, or about 300 mg to about 400 mg; e.g., about 200 mg, about 250 mg, about 300 mg, about 350 mg, or about 400 mg) of stenoparib or the pharmaceutically acceptable salt thereof or the hydrate thereof. In some instances, the second dose includes between about 400 mg to about 600 mg (e.g., about 400 mg to about 450 mg, about 450 mg to about 500 mg, about 550 mg to about 600 mg, about 400 mg to about 500 mg, or about 500 mg to about 600 mg; e.g., about 400 mg, about 450 mg, about 500 mg, about 550 mg, or about 600 mg) of stenoparib or the pharmaceutically acceptable salt thereof or the hydrate thereof.

In a particular example, the first dose of the first composition includes about 200 mg of stenoparib or the pharmaceutically acceptable salt thereof or the hydrate thereof and the second dose of the first composition includes about 400 mg of stenoparib or the pharmaceutically acceptable salt thereof or the hydrate thereof.

In another particular example, the first dose of the first composition includes about 400 mg of stenoparib or the pharmaceutically acceptable salt thereof or the hydrate thereof and the second dose of the first composition includes about 400 mg of stenoparib or the pharmaceutically acceptable salt thereof or the hydrate thereof.

In yet another particular example, the first dose of the first composition includes about 400 mg of stenoparib or the pharmaceutically acceptable salt thereof or the hydrate thereof and the second dose of the first composition includes about 600 mg of stenoparib or the pharmaceutically acceptable salt thereof or the hydrate thereof.

In some instances, the dose of the second composition includes between about 300 mg to about 500 mg (e.g., about 300 mg to about 350 mg, about 350 mg to about 400 mg, about 450 mg to about 500 mg, about 300 mg to about 400 mg, or about 400 mg to about 500 mg; e.g., about 300 mg, about 350 mg, about 400 mg, about 450 mg, or about 500 mg) of dovitinib or the pharmaceutically acceptable salt thereof or the hydrate thereof. In a particular example, the dose of the second composition includes about 300 mg of dovitinib or the pharmaceutically acceptable salt thereof or the hydrate thereof. In another particular example, the dose of the second composition includes about 400 mg of dovitinib or the pharmaceutically acceptable salt thereof or the hydrate thereof. In yet another particular example, the dose of the second composition includes about 500 mg of dovitinib or the pharmaceutically acceptable salt thereof or the hydrate thereof.

In some instances, for each daily administration, the second dose of the first composition is administered to the subject at least 11 to 13 hours (e.g., at least 11, at least 11.5, at least 12, at least 12.5, or at least 13 hours) after administration of the first dose of the first composition. In some instances, the second dose of the first composition is administered to the subject at least 6, 7, 8, 9, 10, 11, 12, 13, 14, 15, 16, 17 or 18 hours after administration of the first dose of the first composition.

In some instances, the first dose and the second dose of the first composition is administered to the subject at about the same time during each day of a dosing cycle. For example, if stenoparib or a pharmaceutically acceptable salt thereof or a hydrate thereof is administered to a subject as a first dose at about 8 am and as a second dose at about 8 pm on Day 1 of a first dosing cycle, then stenoparib or the pharmaceutically acceptable salt thereof or the hydrate thereof is administered as a first dose at about 8 am and as a second dose at about 8 pm on Days 2-28 of the first dosing cycle, and optionally also as a first dose at about 8 am and as a second dose at about 8 pm on Days 1-28 of any additional dosing cycles.

In some instances, the subject is non-responsive to at least one cancer therapy (e.g., one, two, three, four, five, six, seven, eight, nine, ten, or more cancer therapies) other than stenoparib or a pharmaceutically acceptable salt thereof or a hydrate thereof and/or dovitinib and or a pharmaceutically acceptable salt thereof. In a particular instance, the cancer therapy is a PARP inhibitor (PARPi) other than stenoparib.

In some instances, the method includes, prior to administration of the first composition, determining the responsiveness of the subject to treatment with stenoparib or the pharmaceutically acceptable salt thereof or the hydrate thereof by determining the expression level of one or more biomarkers of sensitivity selected from the biomarkers of Table 1; and/or determining the expression level of one or more biomarkers of resistance selected from the biomarkers of Table 2. Methods of determining the responsiveness of a subject to treatment with stenoparib or a pharmaceutically acceptable salt thereof or a hydrate thereof are described in detail below.

In some instances, the method includes, prior to administration of the second composition, determining the responsiveness of the subject to treatment with dovitinib or the pharmaceutically acceptable salt thereof or the hydrate thereof by determining the expression level of one or more biomarkers of sensitivity selected from the biomarkers of Table 3; and/or determining the expression level of one or more biomarkers of resistance selected from the biomarkers of Table 4. Methods of determining the responsiveness of a subject to treatment with dovitinib or a pharmaceutically acceptable salt thereof or a hydrate thereof are described in detail below.

In some instances, a subject treated with stenoparib and dovitinib combination therapy according to any of the methods disclosed herein exhibits a complete response (CR). In some instances, a subject treated with stenoparib and dovitinib combination therapy according to any of the methods disclosed herein exhibits a partial response (PR). In some instances, a subject treated with stenoparib and dovitinib combination therapy according to any of the methods disclosed herein exhibits stable disease (SD). In some instances, a subject treated with stenoparib and dovitinib combination therapy according to any of the methods disclosed herein exhibits SD for at least 16 weeks.

In the methods described herein, stenoparib or a pharmaceutically acceptable salt thereof or a hydrate thereof is administered twice a day (e.g., BID dosing).

The route for administration of stenoparib or a pharmaceutically acceptable salt thereof or a hydrate thereof may be oral. Stenoparib or a pharmaceutically acceptable salt thereof or a hydrate thereof may be administered as a pharmaceutical composition (e.g., including stenoparib or a pharmaceutically acceptable salt thereof or a hydrate thereof in combination with a pharmaceutically acceptable carrier and/or excipient). The pharmaceutical composition (e.g., the first composition) may be formulated as a capsule (e.g., a hard gel capsule) or a tablet (e.g., a film coated tablet). Each capsule or tablet of stenoparib or a pharmaceutically acceptable salt thereof or a hydrate thereof may contain about 50 mg, 100 mg, 150 mg, 200 mg, 250 mg, 300 mg, 350 mg, 400 mg, 450 mg, 500 mg, 550 mg, or 600 mg of stenoparib or the pharmaceutically acceptable salt thereof or the hydrate thereof. In an example, each capsule of stenoparib or the pharmaceutically acceptable salt thereof or the hydrate thereof may contain about 50 mg (e.g., 50 mg±5 mg), about 100 mg (e.g., 100 mg±10 mg), about 150 mg (e.g., 150 mg±15 mg), or about 200 mg (e.g., 200 mg±20 mg) of stenoparib or pharmaceutically acceptable salt thereof.

As an example, when stenoparib is formulated in a tablet or capsule in an amount of about 100 mg (e.g., 100 mg±10 mg), administration of a first dose of about 200 mg (e.g., 200 mg±20 mg) or about 400 mg (e.g., 400 mg±40 mg) of stenoparib involves administering (e.g., orally administering) 2 or 4 of the tablets or capsules comprising stenoparib or a pharmaceutically acceptable salt thereof or a hydrate thereof, respectively. Similarly, administration of the second daily dose of stenoparib of about 400 mg (e.g., 400 mg±40 mg) or 600 mg (e.g., 600 mg±60 mg) involves administering (e.g., orally administering) 4 or 6 of the tablets or capsules comprising stenoparib or a pharmaceutically acceptable salt thereof or a hydrate thereof, respectively. As an alternative example, when stenoparib is formulated in a tablet or capsule in an amount of about 200 mg (e.g., 200 mg±10 mg), administration of a first dose of about 200 mg (e.g., 200 mg±20 mg) or about 400 mg (e.g., 400 mg±40 mg) of stenoparib involves administering (e.g., orally administering) 1 or 2 of the tablets or capsules comprising stenoparib or a pharmaceutically acceptable salt thereof or a hydrate thereof, respectively. Similarly, administration of the second daily dose of stenoparib of about 400 mg (e.g., 400 mg±40 mg) or 600 mg (e.g., 600 mg±60 mg) involves administering (e.g., orally administering) 2 or 3 of the tablets or capsules comprising stenoparib or a pharmaceutically acceptable salt thereof or a hydrate thereof, respectively.

In the methods described herein, dovitinib is administered once a day (e.g., QD dosing).

The route for administration of dovitinib or a pharmaceutically acceptable salt thereof or a hydrate thereof may be oral. Dovitinib or a pharmaceutically acceptable salt thereof or a hydrate thereof may be administered as a pharmaceutical composition (e.g., including dovitinib or a pharmaceutically acceptable salt thereof or a hydrate thereof in combination with a pharmaceutically acceptable carrier and/or excipient). The pharmaceutical composition (e.g., the second composition) may be formulated as a tablet (e.g., a film coated tablet). Each tablet of dovitinib or a pharmaceutically acceptable salt thereof or a hydrate thereof may contain about 50 mg, 100 mg, 150 mg, 200 mg, 250 mg, 300 mg, 350 mg, 400 mg, 450 mg, or 500 mg of dovitinib or the pharmaceutically acceptable salt thereof or the hydrate thereof. In an example, each tablet of dovitinib or the pharmaceutically acceptable salt thereof or the hydrate thereof may contain about 100 mg (e.g., 100±10 mg) of dovitinib.

As an example, when dovitinib is formulated in a tablet or capsule in an amount of about 100 mg (e.g., 100 mg±10 mg), administration of a single dose of about 300 mg (e.g., 300 mg±30 mg), about 400 mg (e.g., 400 mg±40 mg), or about 500 mg (e.g., 500 mg±50 mg) of dovitinib involves administering (e.g., orally administering) 3, 4, or 5 of the tablets or capsules comprising dovitinib or a pharmaceutically acceptable salt thereof or a hydrate thereof, respectively.

The tablets or capsules can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In some instances, for combination therapy of stenoparib and dovitinib, on the days when stenoparib and dovitinib are both administered, dovitinib is administered prior to (e.g., about 0.5, 1, 2, 3, 4, 5, 6, 7, 8, 9, 10, 11, 12, 14, 16, 18, 20, 22, or 24 hours prior to) administration of the first dose of stenoparib. In some instances, for combination therapy of stenoparib and dovitinib, on the days when stenoparib and dovitinib are both administered, dovitinib is administered after administration of the first dose of stenoparib. In a preferred example, on the days when stenoparib and dovitinib are both administered, dovitinib is administered prior to (e.g., about 0.5, 1, 2, 3, 4, 5, 6, 7, 8, 9, 10, 11, 12, 14, 16, 18, 20, 22, or 24 hours prior to) administration of the first dose of stenoparib.

Pharmaceutical Compositions

The methods described herein include administration of stenoparib and a pharmaceutically acceptable salt as a monotherapy or administration of stenoparib and a pharmaceutically acceptable salt and dovitinib and a pharmaceutically acceptable salt as a combination therapy (e.g., both agents are administered separately to the subject). Pharmaceutically acceptable compositions including stenoparib and dovitinib, as well as pharmaceutically acceptable salts thereof, are described below.

Stenoparib and Pharmaceutically Acceptable Salts

A subject as described herein may be treated for a cancer by administration of stenoparib or a pharmaceutically acceptable salt of stenoparib. Stenoparib or a pharmaceutically acceptable salt thereof or a hydrate thereof may be administered in a dosage form. Pharmaceutically acceptable salts of stenoparib described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of stenoparib described herein or separately by reacting a free base group with a suitable organic acid.

Stenoparib may have ionizable groups so as to be capable of preparation as a pharmaceutically acceptable salt. These salts may be acid addition salts involving inorganic or organic acids or the salts may, in the case of acidic forms of stenoparib be prepared from inorganic or organic bases. Frequently, stenoparib may be prepared or used as a pharmaceutically acceptable salt prepared as an addition product of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like. In a particular example, the salt form of stenoparib is stenoparib L-tartrate salt.

Stenoparib or a pharmaceutically acceptable salt thereof or a hydrate thereof can be administered in a pharmaceutical composition that includes one or more pharmaceutically acceptable carriers, excipients, or diluents. Examples of suitable carriers, excipients, or diluents of stenoparib or a pharmaceutically acceptable salt thereof or a hydrate thereof are described in the Handbook of Pharmaceutical Excipients, 6th Edition, Rowe et al., Eds., Pharmaceutical Press (2009), hereby incorporated by reference in its entirety.

A pharmaceutical composition can be formulated to be compatible with its intended route of administration. Oral compositions can include an inert diluent or an edible carrier. The composition can be enclosed in a gelatin capsule or compressed into a tablet. For the purpose of oral therapeutic administration, stenoparib or a pharmaceutically acceptable salt thereof or a hydrate thereof can be incorporated with excipients and used in the form of tablets, troches, or gelatin capsules. In particular, stenoparib or a pharmaceutically acceptable salt thereof or a hydrate thereof can be formulated as hard gelatin capsules (e.g., hard gelatin capsules of 10 mg, 50 mg, or 200 mg) or film coated tablets (e.g., film coated tablets of 10 mg, 50 mg, or 200 mg). Preferably, stenoparib or a pharmaceutically acceptable salt thereof or a hydrate thereof can be formulated as hard gelatin capsules (e.g., hard gelatin capsules of 200 mg). Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. Additionally, tablets or capsules containing stenoparib or a pharmaceutically acceptable salt thereof or a hydrate thereof may include croscarmellose sodium and/or magnesium stearate.

Stenoparib or a pharmaceutically acceptable salt thereof or a hydrate thereof can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art.

The pharmaceutical compositions can be included in a container, pack, or dispenser together with instructions for administration.

Methods of formulating pharmaceutical agents are known in the art, e.g., Niazi, *Handbook of Pharmaceutical Manufacturing Formulations* (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., *Drug Delivery: Principles and Applications* (Second Edition), Wiley 2016; formulation and delivery of peptide and protein agent is described, e.g., in Banga, *Therapeutic Peptides and Proteins: Formulation, Processing, and Delivery Systems* (Third Edition), CRC Press 2015.

Dovitinib and Pharmaceutically Acceptable Salts

A subject as described herein may be treated for a cancer by administration of dovitinib or a pharmaceutically acceptable salt of dovitinib. Dovitinib or a pharmaceutically acceptable salt thereof or a hydrate thereof may be administered in a dosage form. Pharmaceutically acceptable salts of dovitinib described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of dovitinib described herein or separately by reacting a free base group with a suitable organic acid.

Dovitinib may have ionizable groups so as to be capable of preparation as a pharmaceutically acceptable salt. These salts may be acid addition salts involving inorganic or organic acids or the salts may, in the case of acidic forms of dovitinib be prepared from inorganic or organic bases. Frequently, dovitinib may be prepared or used as a pharmaceutically acceptable salt prepared as an addition product of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. In a particular example, the salt form of stenoparib is dovitinib lactate (e.g., dovitinib lactate, monohydrate).

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

Dovitinib or a pharmaceutically acceptable salt thereof or a hydrate thereof can be administered in a pharmaceutical composition that includes one or more pharmaceutically acceptable carriers, excipients, or diluents. Examples of suitable carriers, excipients, or diluents of dovitinib or a pharmaceutically acceptable salt thereof or a hydrate thereof are described in the *Handbook of Pharmaceutical Excipients,* 6th Edition, Rowe et al., Eds., Pharmaceutical Press (2009), hereby incorporated by reference in its entirety.

A pharmaceutical composition can be formulated to be compatible with its intended route of administration. Oral compositions can include an inert diluent or an edible carrier. The composition can be enclosed in a gelatin capsule or compressed into a tablet. For the purpose of oral therapeutic administration, dovitinib or a pharmaceutically acceptable salt thereof or a hydrate thereof can be incorporated with excipients and used in the form of tablets, troches, or gelatin capsules. In particular, dovitinib or a pharmaceutically acceptable salt thereof or a hydrate thereof can be formulated as hard gelatin capsules (e.g., hard gelatin capsules of 10 mg, 25 mg, 50 mg, 100 mg, or 200 mg) or film coated tablets (e.g., film coated tablets of 10 mg, 50 mg, 100 mg, 200 mg, or 250 mg). In particular, dovitinib or a pharmaceutically acceptable salt thereof or a hydrate thereof can be formulated as film coated tablets (e.g., film coated tablets of 100 mg). Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. Additionally, tablets or capsules containing dovitinib or a pharmaceutically acceptable salt thereof or a hydrate thereof may include microcrystalline cellulose, crospovidone, silica anhydrous, magnesium stearate, and/or a film-coating.

Dovitinib or a pharmaceutically acceptable salt thereof or a hydrate thereof can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art.

The pharmaceutical compositions can be included in a container, pack, or dispenser together with instructions for administration.

Methods of formulating pharmaceutical agents are known in the art, e.g., Niazi, *Handbook of Pharmaceutical Manufacturing Formulations* (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., *Drug Delivery: Principles and Applications* (Second Edition), Wiley 2016; formulation and delivery of peptide and protein agent is described, e.g., in Banga, *Therapeutic Peptides and Proteins: Formulation, Processing, and Delivery Systems* (Third Edition), CRC Press 2015.

DRP® Companion Diagnostic for Stenoparib

The methods described herein include administration of stenoparib monotherapy or stenoparib and dovitinib combination therapy to a subject with a cancer who may have sensitivity or resistance to treatment including stenoparib or a pharmaceutically acceptable salt thereof or a hydrate thereof. The methods may include determining, prior to therapy, whether the subject is likely to respond to the therapy, e.g., using a DRP® companion diagnostic for stenoparib.

A subject with a cancer (e.g., a subject with a newly diagnosed cancer or a recurrence thereof) can be assessed for sensitivity or resistance to stenoparib or a pharmaceutically acceptable salt thereof or a hydrate thereof by detecting expression of a biomarker (e.g., one or more of the biomarkers of Table 1 and/or Table 2) in a biological sample obtained from the subject. The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., lymph nodes, thymus, spleen, bone marrow, breast, colorectal, pancreatic, cervical, prostate, bladder, lung, gastrointestinal, head, neck, or ovarian tissue).

Table 1 below lists biomarkers for sensitivity to treatment with stenoparib or a pharmaceutically acceptable salt thereof or a hydrate thereof, which are included in the stenoparib-DRP® companion diagnostic. Table 2 below lists biomarkers for resistance to treatment with stenoparib or a pharmaceutically acceptable salt thereof or a hydrate thereof, which are included in the stenoparib-DRP® companion diagnostic.

TABLE 1

Biomarkers of sensitivity to stenoparib. Dashes mean that the Affymetrix probeset has not been mapped to a specific gene. Affymetrix IDs refer to the array type HG-U133_Plus_2.

| Gene | Affymetrix ID | Correlation | Affymetrix Probe Sequence | SEQ ID NO: |
|---|---|---|---|---|
| SRSF7 | 214141_x_at | 0.516 | GATCAAGATCTATCTCTCTTCGTAG | 1 |
| UCHL 1 | 201387_s_at | 0.494 | GAGGGACTTTGCTGATTTCCCCTCT | 2 |
| MLLT11 | 211071_s_at | 0.491 | TCAGTGGGCACAGTTCTTCAGCTAC | 3 |
| ADD2 | 205268_s_at | 0.487 | CCTGGAGCAATGCACTGTACCTGCC | 4 |
| ADD2 | 213484_at | 0.451 | GTCTGTGTCTGACAATCGTCACGCA | 5 |
| PRMT1 | 206445_s_at | 0.441 | TCCCCGTACACGCACTGGAAGCAGA | 6 |
| SRSF3 | 202899_s_at | 0.439 | TTGAAGATCCCCGAGATGCAGCTGA | 7 |
| PRMT5 | 217786_at | 0.412 | GCGTTTCTGGCGATGCAGCAATTCC | 8 |
| COCH | 205229_s_at | 0.402 | AACCATGCCTACTAAATGTACAGAT | 9 |
| RUVBL1 | 201614_s_at | 0.391 | AGATCATTAAAATCCGTGCCCAGAC | 10 |
| MARCKSL1 | 200644_at | 0.39 | TTACTCAAGTTCAAACCTCCAGCCT | 11 |
| CHERP | 202230_s_at | 0.39 | TGTTCTAGATTTCCTGTAGCTGTGA | 12 |
| MTSS1 | 203037_s_at | 0.39 | GTGCTTTAGTTGCTAGTTTGTACTG | 13 |
| LSM4 | 202736_s_at | 0.385 | CCTGCGAGAAGTCATCTGCACGTCC | 14 |
| RAPGEF5 | 204681_s_at | 0.379 | GCCATTAACAGTGTTTTCTTTCCCA | 15 |
| PRPF4 | 209161_at | 0.367 | CGCAGCCACGCCGATGGTTATACAG | 16 |

TABLE 1-continued

Biomarkers of sensitivity to stenoparib. Dashes mean that the Affymetrix probeset has not been mapped to a specific gene. Affymetrix IDs refer to the array type HG-U133_Plus_2.

| Gene | Affymetrix ID | Correlation | Affymetrix Probe Sequence | SEQ ID NO: |
|---|---|---|---|---|
| LSM4 | 202737_s_at | 0.366 | TCTTGCTAAAACCGGCAATTCTCCG | 17 |
| DESI2 | 212371_at | 0.365 | TGACTCCATTTCTGTAAGCTACTCT | 18 |
| RNPS1 | 200060_s_at | 0.363 | GGTGGTCTTTCAGGTTATCTTGGCA | 19 |
| SNX10 | 218404_at | 0.362 | TGTGTCTTAGATCCTCATTATTTTA | 20 |
| CUL3 | 201371_s_at | 0.361 | CTGTACTCTTCGCATGGACTGGGAA | 21 |
| CHD4 | 201184_s_at | 0.36 | CGGCTCTAGCCACTGAGCGGCTAAA | 22 |
| MSH2 | 209421_at | 0.359 | AAGATTGGTGCTTTTTGCATGTTTG | 23 |
| HNRNPM | 200072_s_at | 0.358 | GCCGAGAGAGCCTGCCGGATGATGA | 24 |
| SRSF1 | 211784_s_at | 0.358 | GGAGCAATCTCCTTGGAAGGATTCA | 25 |
| NELL2 | 203413_at | 0.357 | GAAAAGTCATCCCTATTTCCTTGTT | 26 |
| PAICS | 201014_s_at | 0.356 | AGTGTTGATGGGCTCTACTTCTGAT | 27 |
| HOXA10 | 213150_at | 0.356 | ATTTACCTCTAAATTTCCATATCCT | 28 |
| BUB1B | 203755_at | 0.354 | GGCCTTGTCTAACTTTTGTGAAGAA | 29 |
| E2F5 | 221586_s_at | 0.352 | CCACAGAAATCCAGCATGGCAACTC | 30 |
| MAGED4 MAGED4B SNORA11D SNORA11E | 221261_x_at | 0.351 | AAGATGAAGCTCTCTTTGCTCTTCC | 31 |
| PRPF8 | 200000_s_at | 0.349 | GAGGGGGAGGTTTACTCTGCGGATC | 32 |
| SORD | 201563_at | 0.348 | ATCGCATCATGCCAACTTGTGACTT | 33 |
| HNRNPU | 200593_s_at | 0.346 | TTTTCCTGGCCGTGGTAGTTACTCA | 34 |
| PEX5 | 203244_at | 0.344 | TCATCCTCTTAGAAGCACCTGTGAA | 35 |
| HYPK MIR1282 SERF2 SERF2-C15ORF63 | 218680_x_at | 0.344 | GGTAGAGGCGCTTATTGCCCTAACC | 36 |
| STRAP | 200870_at | 0.343 | TCTTTCCTTCAGCTCCTGATGTTAA | 37 |
| NDUFAB1 | 202077_at | 0.341 | CATCCAGGACCGTGTTCTTTACGTA | 38 |
| FARSA | 216602_s_at | 0.341 | TATTCCGGAATGAGACCCTGGACGC | 39 |
| STOML2 | 215416_s_at | 0.339 | GCTGCAGCTCTGACACAACATAATG | 40 |
| ERH | 200043_at | 0.337 | GAGGATCTTGTTCAATCGGAAACCC | 41 |
| HSBP1 | 200941_at | 0.337 | TGATGTTCTCAAGCCTCGGAAGTGG | 42 |
| DDX39A | 201584_s_at | 0.337 | TTAACTACGACATGCCTGAGGACTC | 43 |
| ODC1 | 200790_at | 0.335 | CCAGAGGCCGACGATCTACTATGTG | 44 |
| TAF5 | 210053_at | 0.334 | GCTACATACAACCTAGTACACTTGA | 45 |
| TBC1D31 | 214061_at | 0.334 | AATGCGGCTGTAGAACATGCTGAAA | 46 |
| TRA2B | 200892_s_at | 0.333 | CCTTCTCCTTACTATAGTCGTGGAG | 47 |
| NUDC | 201173_x_at | 0.333 | CACAGGTCCCGGGGCATCAGGAGAA | 48 |
| DDX23 | 201440_at | 0.333 | CCAAGGGGTGCTGTATGCTCTAGGC | 49 |

TABLE 1-continued

Biomarkers of sensitivity to stenoparib. Dashes mean that the Affymetrix probeset has not been mapped to a specific gene. Affymetrix IDs refer to the array type HG-U133_Plus_2.

| Gene | Affymetrix ID | Cor-relation | Affymetrix Probe Sequence | SEQ ID NO: |
|---|---|---|---|---|
| PRPF31 | 202407_s_at | 0.333 | CAGTTTCCACGAGAGCACAGAAGGG | 50 |
| UBE2S | 202779_s_at | 0.333 | GGCGCCAATGGCGAGATCTGCGTCA | 51 |
| TCF4 | 222146_s_at | 0.332 | GAGAAGGAGCGGAGGATGGCCAACA | 52 |
| MLF2 | 200948_at | 0.33 | GGGTCAATGCATTTTGGGGTGAGCT | 53 |
| CCDC181 | 206721_at | 0.329 | CAAACCTTTTCGTTTTACTGATCAT | 54 |
| TCF4 | 213891_s_at | 0.328 | TTGGTCAAGGCCATTACCTGTTTCC | 55 |
| DESI2 | 222158_s_at | 0.328 | TATACCCTTTCTACAGAGTTGCCTC | 56 |
| RPF1 | 218462_at | 0.327 | GCTGAACAGGCCTATCTTGAACTTT | 57 |
| PASK | 216945_x_at | 0.326 | TAATGGCCAAGGCTGTTTGCATCCC | 58 |
| NUP88 | 202900_s_at | 0.325 | AGCGAAAGTGCATTCAGTCCATCCT | 59 |
| RNASEH2A | 203022_at | 0.325 | ACTGATTATGGCTCAGGCTACCCCA | 60 |
| FBL | 211623_s_at | 0.325 | GTGATCGAGGATGCTCGACACCCAC | 61 |
| LOC101928747 RBMX SNORD61 | 213762_x_at | 0.325 | GGCAGGCAATTCTAAGATCTTCCAC | 62 |
| NXF1 | 208922_s_at | 0.324 | GTGATCGTAGTCATGCCTCAGAAGC | 63 |
| PLEKHO1 | 218223_s_at | 0.323 | GATGGGAAGCGAAAGGCCAAGGACC | 64 |
| GAR1 | 219110_at | 0.323 | ACAGACATCACCAGTTGACTTCTGC | 65 |
| RPA1 | 201529_s_at | 0.321 | GTAACTAGGTTTTTGCTTCTCCAGT | 66 |
| ZNF24 | 212534_at | 0.321 | CACAGCTTCCTAGCCACAGTGATAA | 67 |
| BOP1 MIR7112 | 216397_s_at | 0.321 | CGGCAGCGCAAGATGAGGGTGAATG | 68 |
| RAB3B | 205924_at | 0.32 | AGATACTCAGCACTAGACTAACATA | 69 |
| SLC35G2 | 219569_s_at | 0.319 | CATTGCTATATGTGTCTGTTCTACT | 70 |
| TSPAN3 | 200973_s_at | 0.318 | GAGACAGCTGCATTGTTGTGGAATT | 71 |
| DKC1 MIR664B SNORA56 | 201479_at | 0.318 | GCCTGATGGGCCTGGTAGTTTTCCA | 72 |
| PSMC3IP | 213951_s_at | 0.318 | GTAACCGTAGCAAAACTGCATTGGT | 73 |
| DNAJC7 | 202416_at | 0.316 | AGATCGGCATAGTGGAGCCAGTGCT | 74 |
| RRP1B | 212846_at | 0.316 | TTTGTAAAATGATGCTTCCCCCTTC | 75 |
| NME1 | 201577_at | 0.315 | AAGGAGATCGGCTTGTGGTTTCACC | 76 |
| SNRPA | 201770_at | 0.315 | ACAGCATTGTACCCAGAGTCTGTCC | 77 |
| DBN1 | 217025_s_at | 0.315 | TGCCCAATCGGAAGAGCTCTGTGCC | 78 |
| KIAA0020 | 203712_at | 0.314 | AGGTGCCATTATTCTTTCTAGCCTC | 79 |
| SUPV3L1 | 212894_at | 0.313 | GAAGCTGTCCACGATGTCTTGGATC | 80 |
| ZNF573 | 217627_at | 0.31 | GGAGCATAAAAGTGTAAGACCGTAA | 81 |
| FAM134B | 218510_x_at | 0.31 | GATCTTTCAGATTTTCCATCTCTAG | 82 |
| TOX3 | 214774_x_at | 0.309 | ATGACCACTGTTAGCCCATTATATT | 83 |

TABLE 1-continued

Biomarkers of sensitivity to stenoparib. Dashes mean that the Affymetrix probeset has not been mapped to a specific gene. Affymetrix IDs refer to the array type HG-U133_Plus_2.

| Gene | Affymetrix ID | Cor-relation | Affymetrix Probe Sequence | SEQ ID NO: |
|---|---|---|---|---|
| HSPD1 | 200806_s_at | 0.306 | TAGTATCCAGTCCATTGTACCTGCT | 84 |
| ACLY | 210337_s_at | 0.306 | AGATGGTCTCATCGGAGTCGCATTT | 85 |
| TOX3 | 216623_x_at | 0.306 | ATATCTATGACCACTGTTAGCCCAT | 86 |
| MSANTD3-TMEFF1 TMEFF1 | 205122_at | 0.305 | TAAAGCCTATTCTACCAGTTAAACT | 87 |
| AKIRIN1 | 217893_s_at | 0.305 | GGAGCATCAGGGTTGGCTTGGGAGC | 88 |
| UBE2M | 203109_at | 0.304 | CATTGACCTCGAGGGCAACGTCTGC | 89 |
| MTF2 | 203345_s_at | 0.304 | TTATACGTTTATATGCTCTGTCTGC | 90 |
| EWSR1 | 209214_s_at | 0.304 | GTTGGCCACAACATTATGATTATTC | 91 |
| FARSA | 202159_at | 0.303 | TCCTGTGTGGTGTGTCTACTGTGAG | 92 |
| SKP2 | 203625_x_at | 0.303 | AGAGCTGGGGTTAGGATCCGGTTGG | 93 |
| TMEM97 | 212279_at | 0.303 | TCCTTTCTGTTTTGCGAGCTTGTGT | 94 |
| HNRNPD | 221481_x_at | 0.303 | AAAAGCCCAGTGTGACAGTGTCATG | 95 |
| ILKAP | 221548_s_at | 0.303 | CAGTACAAGCGCTGCGGTGTCACCT | 96 |
| NASP | 201970_s_at | 0.302 | GAAAGCCAACAGACGGTGCTTCCTC | 97 |
| SNRPD1 | 202690_s_at | 0.301 | GTTTACCTCTGGATACACTACTTGT | 98 |
| TIMM44 | 203093_s_at | 0.301 | CGCTCTGCCGAGACCAGGACGAGCT | 99 |
| PKN1 | 202161_at | 0.3 | CACCGACGTCAGCAACTTCGACGAG | 100 |
| STAU2 | 204226_at | 0.299 | AAGCCTACTAGAGCCATTGTATGTG | 101 |
| DNAAF2 | 219166_at | 0.299 | CTTCATTACTGAACAAAACTACGGT | 102 |
| SNRPD2 | 200826_at | 0.297 | TGCTCATCAACTGCCGCAACAATAA | 103 |
| FUS | 200959_at | 0.297 | ATCCCACCTGTGAGAATATGAACTT | 104 |
| PASK | 213534_s_at | 0.297 | AGCTAAACACCAATTTCTTCCTGCT | 105 |
| ATP6V1G2-DDX39B DDX39B SNORD84 | 200041_s_at | 0.296 | TAGTGAGCTGCCTGATGAGATAGAC | 106 |
| PDSS1 | 220865_s_at | 0.296 | GCAGCTATCTTACCAGACTGTGCCT | 107 |
| NUDC | 210574_s_at | 0.295 | GAAGTTCATGGATCAACATCCGGAG | 108 |
| TOX3 | 215108_x_at | 0.295 | GGTGACATAAACCATTCATTGCTAC | 109 |
| TPGS2 | 212055_at | 0.294 | AAGTGCCCAAATAAGTCTGAGTGCT | 110 |
| SLIRP | 221434_s_at | 0.294 | TTTGACAAGGAGACTGGCTTTCACA | 111 |
| NCL | 200610_s_at | 0.293 | AAGTTTGAATAGCTTCTGTCCCTCT | 112 |
| ANP32A | 201051_at | 0.293 | TTTGGAGTTCTCTTACGTTTCCTGG | 113 |
| SAFB | 201748_s_at | 0.293 | TGGCGAGAGAAGCATGTCCGGTCAC | 114 |
| STIP1 | 212009_s_at | 0.293 | AATAAGTGCCGGGAGCTTTGTGAGA | 115 |
| CEP68 | 212677_s_at | 0.293 | GGCCAGAAACCTTGGGTCTTTTCAT | 116 |

TABLE 1-continued

Biomarkers of sensitivity to stenoparib. Dashes mean that the Affymetrix probeset has not been mapped to a specific gene. Affymetrix IDs refer to the array type HG-U133_Plus_2.

| Gene | Affymetrix ID | Cor-relation | Affymetrix Probe Sequence | SEQ ID NO: |
|---|---|---|---|---|
| STIP1 | 213330_s_at | 0.291 | GGATGTGGGTCTGATTGCAATTCGG | 117 |
| C8orf33 | 218187_s_at | 0.291 | TGGACCATGGTCTAGCAGTAGCATC | 118 |
| MRPL11 | 219162_s_at | 0.29 | GGGCATTCGCGTGGTGAAGGACCTC | 119 |
| POLR21 | 212955_s_at | 0.288 | GCTGTACCCCAAGGAAGACAAGGAG | 120 |
| FAM134B | 218532_s_at | 0.288 | AAATCTCTGAACTGTGTGGGTTTTG | 121 |
| MCAM MIR6756 | 211042_x_at | 0.286 | TGCCCTCAAACATACAGAACTTCCA | 122 |
| ECSIT | 218225_at | 0.285 | TCATCTCTAGCAGTATGGCATCCCC | 123 |
| MDK | 209035_at | 0.284 | GCAAGGATTGCGGCGTGGGTTTCCG | 124 |
| PUF60 | 209899_s_at | 0.283 | TCAATGGCCGCTGGTTTGCTGGCCG | 125 |
| PFN2 | 204992_s_at | 0.282 | CACACCAGCTCTACTCTTTAGTAAA | 126 |
| SYNCRIP | 209025_s_at | 0.282 | AGAAACTCACCCTAAATCTGAACGG | 127 |
| TSPAN3 | 200972_at | 0.281 | AAGTGGTAACAGGACTGATGCCGAA | 128 |
| SLC16A1 | 202236_s_at | 0.281 | TGTTTATAGATCACTGCCCTTTTTG | 129 |
| POLR2H | 209302_at | 0.281 | AAGTCACTCAGGTCATGGGCATTGT | 130 |
| MAP3K7 | 211537_x_at | 0.281 | TGATTACTACCTCAGGACCAACCTC | 131 |
| CSRP2 | 207030_s_at | 0.28 | GTACTTGGATAGGCTGGCTAACTCG | 132 |
| BCL11A | 210347_s_at | 0.28 | GAAGCTCGAGAGCCCTTAAGTTCTG | 133 |
| PNKP | 218961_s_at | 0.279 | CCATCGACAACACAAACCCAGACGC | 134 |
| DNAJC6 | 204720_s_at | 0.278 | AGCTTGTTGTTGATCAGATTCACTG | 135 |
| FDFT1 | 208647_at | 0.278 | GCAGAGCATTCAGTGCCACGGTTTA | 136 |
| FADS1 MIR1908 | 208963_x_at | 0.278 | CTCTTCAGCAGCATCTACTCTAGGC | 137 |
| RPARP-AS1 | 214857_at | 0.277 | CTGCTGTAAGGACTGGTTCCAGAAT | 138 |
| DHRS7 | 210788_s_at | 0.276 | GAACTTGCCACATACCCAGGTATAA | 139 |
| CCNB1IP1 | 217988_at | 0.276 | CATGAAGGCACCCTTGAACCATCCA | 140 |
| CCT3 LOC101927137 | 200910_at | 0.275 | GGAGCCATTGGCTGTGAAGCTGCAG | 141 |
| DDX18 | 208895_s_at | 0.274 | AATCTGACCCTATCGGAAACTCAAA | 142 |
| AARSD1 PTGES3L PTGES3L-AARSD1 | 222064_s_at | 0.273 | ATAGCCTCAGGAACAGTCCAGACTG | 143 |
| HNRNPDL | 209067_s_at | 0.272 | GGTGGTGATCAAAACTATAGTGGCT | 144 |
| ATXN7L3B | 212114_at | 0.272 | TGATCACCCTGCAATCCTATTATGT | 145 |
| MRPS14 | 203801_at | 0.271 | ACTTAGAATCCATCTCACTACCAAT | 146 |
| SOX4 | 201416_at | 0.269 | TAGAGACTATGTCGCTTTCCTGAGC | 147 |
| ELOVL2 | 213712_at | 0.268 | TACTGTGATGGGCAGAACAGCCTTT | 148 |
| KCNJ8 | 205303_at | 0.267 | TCTCATTTAGGACTGGGTTCCCCAC | 149 |

TABLE 1-continued

Biomarkers of sensitivity to stenoparib. Dashes mean that the Affymetrix probeset has not been mapped to a specific gene. Affymetrix IDs refer to the array type HG-U133_Plus_2.

| Gene | Affymetrix ID | Cor-relation | Affymetrix Probe Sequence | SEQ ID NO: |
|---|---|---|---|---|
| TRIAP1 | 218403_at | 0.267 | ACAGCTTTTAACACAGTTCCCTGCC | 150 |
| EIF2B1 | 201632_at | 0.266 | GATGAAAGATGAGCCCAAGTCCACC | 151 |
| FBXL14 | 213145_at | 0.266 | GATCCTCTTAAAACGTTTATATTCT | 152 |
| MAPRE2 | 213489_at | 0.266 | CCCTGGTCACATGTCATCGGGCTGG | 153 |
| ORC4 | 203352_at | 0.264 | ATCCACATCAGAATCCCTTGTAGGA | 154 |
| MDN1 | 212693_at | 0.264 | ACTGCTTTCAAGCTGGACTGAGCCA | 155 |
| KNOP1 | 213237_at | 0.264 | TAAACATTCCGTCCCTGTTTGAGAC | 156 |
| KBTBD11 | 204301_at | 0.263 | GTGAGATCAAAGCTCCTCCAAAGCC | 157 |
| FADS2 | 202218_s_at | 0.262 | CCTCGGTGGCCCTGACTGTCAGGGA | 158 |
| RANBP1 | 202483_s_at | 0.262 | TCACGCCGATGATGGAGCTGAAGCC | 159 |
| PLEKHB1 | 209504_s_at | 0.261 | GAGTTCTATTTGAGACTTCCAGCCC | 160 |
| HSPE1 | 205133_s_at | 0.26 | CCAAAGGAGGCATTATGCTTCCAGA | 161 |
| TMEM97 | 212282_at | 0.26 | GAAGTGTGCTAGTATGCTCCCTAGT | 162 |
| ITFG2 LOC100507424 | 220589_s_at | 0.26 | GTTGGGGTTGGAGACGTGTGTAATA | 163 |
| SFPQ | 201586_s_at | 0.259 | GGAGGCTAAGTATTGCTTTCTACAA | 164 |
| RFC3 | 204127_at | 0.259 | TCATTAGCTCTGCCCTTTTTAATTA | 165 |
| SDR39U1 | 213398_s_at | 0.259 | CACTTCTCCTTTACGCTGTGTAGAG | 166 |
| PBK | 219148_at | 0.259 | GTACTTTGATACTGCTCATGCTGAC | 167 |
| PHB | 200658_s_at | 0.258 | CAGGGGATGGCCTGATCGAGCTGCG | 168 |
| KHDRBS1 | 201488_x_at | 0.258 | CCTTATTCCATTCTTAACTCTGCAT | 169 |
| PDAP1 | 202290_at | 0.256 | GCAGTCACTCTCCCTGAATAAGTAA | 170 |
| SSRP1 | 200957_s_at | 0.255 | GAAGAAGAACTAGCCAGTACTCCCC | 171 |
| B3GALT2 | 210121_at | 0.251 | GGAGTGCCAAGTTTGCAAACCTGCA | 172 |

TABLE 2

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Cor-relation | Probe sequence | SEQ ID no |
|---|---|---|---|---|
| HLA-E | 200904_at | 0.488 | AATGGGTTATCACAGGAATGGGACT | 173 |
| HLA-E | 200905_x_at | 0.477 | TGGGCAGAGTGCGGCAGCTCATGCC | 174 |
| GADD45B | 209304_x_at | 0.47 | TGGAGTGAGACTGACTGCAAGCCCC | 175 |
| CLIC1 | 208659_at | 0.454 | TTTTTGGATGGCAACGAGCTCACCC | 176 |
| LASP1 | 200618_at | 0.451 | TTATTGCTTAATTTCTGCCTTTCCC | 177 |
| HLA-E | 217456_x_at | 0.445 | GCTGCCTTGTGTGCGACTGAGATGC | 178 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Cor-relation | Probe sequence | SEQ ID no |
|---|---|---|---|---|
| APOBEC3B | 206632_s_at | 0.441 | CTACGATGAGTTTGAGTACTGCTGG | 179 |
| LGALS1 | 201105_at | 0.435 | CTCCTGGACTCAATCATGGCTTGTG | 180 |
| TAPBP | 208829_at | 0.435 | TGGAGGGCGCTCATCAAGTAGCTGC | 181 |
| AHNAK | 211986_at | 0.432 | TGGTCCCAGCCAGTTTGGTGCTGAC | 182 |
| BHLHE40 | 201170_s_at | 0.427 | GATCCTTTCTGTAGGCTAATTCCTC | 183 |
| S100A11 | 200660_at | 0.423 | TTCCCAGAAGCGGACCTGAGGACCC | 184 |
| LITAF | 200704_at | 0.413 | GACCTTCAAGGGTCCTCGTTTTGAT | 185 |
| ZBTB38 | 219221_at | 0.409 | GACGGTGCTTTTCGGTGCAAGGAAA | 186 |
| STAT1 | 209969_s_at | 0.408 | TGAACTTGTTGAGATCCCCGTGTTA | 187 |
| TCIRG1 | 204158_s_at | 0.404 | TTCTACTCAGGCACGGGCTACAAGC | 188 |
| S100A11P1 | 208540_x_at | 0.397 | CCGGTGTCCTTGACCACATGAAGAA | 189 |
| CTSA | 200661_at | 0.39 | TGATGCACTGATTCCATCCCAGGAA | 190 |
| VEGFA | 210512_s_at | 0.39 | TGACAGTCACTAGCTTATCTTGAAC | 191 |
| STOM | 201061_s_at | 0.388 | TTGTGTGAAGTGGTTCACCCTTGAG | 192 |
| P4HB | 200654_at | 0.387 | GACTTCCGGATCCTGTCAGGGTGTC | 193 |
| LITAF | 200706_s_at | 0.387 | GACAAAGATCTTGCCTTACAGACTT | 194 |
| FXYD5 | 218084_x_at | 0.384 | TGGTCGCAGCTGTGCTGTTCATCAC | 195 |
| HLA-C | 208812_x_at | 0.382 | GTGACTTCAAGAGCCTCTGGCATCT | 196 |
| YPEL5 | 217783_s_at | 0.38 | GAGAACAACAGCATTCATTTCCATT | 197 |
| HLA-C | 214459_x_at | 0.379 | CCCTCACCCTGAGATGGGAGCCGTC | 198 |
| HLA-C | 211799_x_at | 0.374 | CACCATCCCCAACTTGGGCATCGTT | 199 |
| STOM | 201060_x_at | 0.373 | AGTAAATGATTCCTCCTTGTTCTGT | 200 |
| PLIN3 | 202122_s_at | 0.373 | CAAAACGGGCATCACCCAGTTGACC | 201 |
| RRBP1 | 201206_s_at | 0.37 | AAGGAGGGCACCTCTGTCTGAGTTT | 202 |
| RF1 | 202531_at | 0.37 | TTATTTATACAGTGCCTTGCTCGGG | 203 |
| LMNA | 212086_x_at | 0.37 | TTCGGGGACAATCTGGTCACCCGCT | 204 |
| NPC2 | 200701_at | 0.369 | CCTCATTGAGTTCGGTGCATCTGGC | 205 |
| P4HB | 200656_s_at | 0.368 | TGCTTGCTACCGTGTTCGGAGTCTC | 206 |
| KLF6 | 208961_s_at | 0.367 | CCCTGCACATGAAGAGGCACCTCTG | 207 |
| HLA-B | 209140_x_at | 0.365 | GGCTGTCCTAGCAGTTGTGGTCATC | 208 |
| RHOC | 200885_at | 0.362 | GTCACACACCAGCACTTTATACACT | 209 |
| CD59 | 200985_s_at | 0.362 | GAACACTCTACTACATGTGACTGGC | 210 |
| SRGN | 201858_s_at | 0.362 | GAGGACTACTCTGGATCAGGCTTCG | 211 |
| SRGN | 201859_at | 0.359 | GAGCTAGTGGATGTGTTTGTCTACA | 212 |
| STAT1 | 200887_s_at | 0.358 | TTCCTTCCTTATCACTGACACAAAA | 213 |
| TNFSF10 | 202687_s_at | 0.358 | GGACTCTATTCCATCTATCAAGGGG | 214 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Cor-relation | Probe sequence | SEQ ID no |
|---|---|---|---|---|
| HLA-B | 211911_x_at | 0.358 | CCCCATCGTGGGCATTGTTGCTGGC | 215 |
| PIEZO1 | 202771_at | 0.357 | GCGGATTCTTCAGCGAGATCTCGCA | 216 |
| LGALS3 | 208949_s_at | 0.355 | CTCACCAGTGCTTCATATACCATGA | 217 |
| LDLRAP1 | 221790_s_at | 0.355 | GCAAGTTTCATCAGCCCTAGGGAAA | 218 |
| CD97 | 202910_s_at | 0.353 | CTCAGCTTCCCTCTTAAGCTAAGAC | 219 |
| HLA-B | 208729_x_at | 0.353 | CCCCATCGTGGGCATTGTTGCTGGC | 220 |
| CFLAR | 209939_x_at | 0.353 | GAATGTTCTCCAAGCAGCAATCCAA | 221 |
| FNDC3B LOC101928615 | 218618_s_at | 0.353 | ATGTGCGTGTCGTCGCTGTTTAGAC | 222 |
| CKLF CKLF-CMTM1 | 219161_s_at | 0.353 | CACAAGCCCCTGAACCATATATTGT | 223 |
| IFI35 | 209417_s_at | 0.351 | GATGTGGACGTTCGGGAGCTACTGC | 224 |
| TIPARP | 212665_at | 0.35 | TCCTGTTGTTTGCTGCCATTGGCAT | 225 |
| TAP1 | 202307_s_at | 0.348 | GTGGCCAGCACTCTGAAACTGAGAA | 226 |
| MICALL2 | 219332_at | 0.348 | AGTTCCGCTTGTCCAAGATCTGGTC | 227 |
| RRBP1 | 201204_s_at | 0.347 | AGAGCCCCAGTTTGTAAATGAACCT | 228 |
| ZFP36 | 201531_at | 0.347 | GTCCCCAAGTGTGCAAGCTCAGTAT | 229 |
| HLA-G | 211528_x_at | 0.347 | GACGTGGAGCTCGTGGAGACCAGGC | 230 |
| TNIP1 | 207196_s_at | 0.346 | TTTTTGCTTCAAGCTCTGTAGCAGG | 231 |
| CD59 | 200983_x_at | 0.345 | TCCATTTCTGGCAGCAGCCTGGAGC | 232 |
| VEGFA | 212171_x_at | 0.345 | TCTACCCCAGGTCAGACGGACAGAA | 233 |
| LDLRAP1 | 57082_at | 0.345 | ACGGGCTGTCCGTGTGCCTCCTGTG | 234 |
| FLNB | 208613_s_at | 0.343 | GGTGGAGTCAGTGACCAGGTCGTCT | 235 |
| PSG6 | 209738_x_at | 0.343 | CTAACCCACCGGCAGAGTATTTTTG | 236 |
| CBX7 | 212914_at | 0.342 | GCTTTCGAAGTGGCCAGCTGCGGCC | 237 |
| RARRES3 | 204070_at | 0.339 | GTGTTAGAAGCAGCTGTGGGGGTCC | 238 |
| CFLAR | 210563_x_at | 0.339 | GAGTGAGGCGATTTGACCTGCTCAA | 239 |
| SUN2 | 212144_at | 0.337 | TAAGGGCTTGATTCCTAGCCCCGTT | 240 |
| EHD2 | 45297_at | 0.337 | AGGGGCCTCTGAACGGAACAGTGTC | 241 |
| MAP3K5 | 203836_s_at | 0.336 | TGAGCACGCTCAGTTCTACTGTGTC | 242 |
| BTN3A2 | 209846_s_at | 0.336 | GTCTTCGTCCGATACCAATAAGTCA | 243 |
| NOL12 TRIOBP | 210276_s_at | 0.336 | AGCTGAGCCACATCAAGACACGGTC | 244 |
| CKLF | 221058_s_at | 0.336 | CTTATTTACCGGAAGCTTCTGTTCA | 245 |
| ARPC1B | 201954_at | 0.335 | TGCCTTCATCCTAACTGCTGGGGAA | 246 |
| TNFSF10 | 202688_at | 0.335 | GAGGCACCACTAAAAGATCGCAGTT | 247 |
| HLA-G | 211529_x_at | 0.335 | TACCCTGCGGAGATCATACTGACCT | 248 |
| RP11-395B7.7 | 214808_at | 0.335 | GGATGGGAAGTGTTGCATTGAGCAT | 249 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Correlation | Probe sequence | SEQ ID no |
|---|---|---|---|---|
| EHD2 | 221870_at | 0.335 | CTTGGAGATATTTCCGTCCTCCACC | 250 |
| LEPROT | 202378_s_at | 0.334 | AGGCCTCTCATGACCCAGGAAGGCC | 251 |
| BTN3A2 BTN3A3 | 204820_s_at | 0.333 | TCATCACTATTATTGCTCACCACTG | 252 |
| INPP4B | 205376_at | 0.332 | AAGCTGACACCTAAGTTTACCAACA | 253 |
| DUSP1 | 201041_s_at | 0.331 | TAGGTGTCTGCCTTCACAAATGTCA | 254 |
| EVI2A | 204774_at | 0.33 | ATATTCCCTATGTAGCAACAGTGGT | 255 |
| TFPI | 213258_at | 0.33 | GATCATGCTGAAAACCACTCAAACG | 256 |
| EHD1 | 209037_s_at | 0.329 | AAGGTCCATAAAGACTGAGCGGATG | 257 |
| VEGFA | 210513_s_at | 0.329 | CTGAGGAGTCCAACATCACCATGCA | 258 |
| EPAS1 | 200878_at | 0.328 | GGACGACACCTCTGGTTTTTCAATA | 259 |
| IQGAP1 | 210840_s_at | 0.328 | TTCACTCCATCCCTATGGCAGAGGA | 260 |
| IL6ST | 212195_at | 0.327 | GAGATGCATTTAAGGCCGATAGTGA | 261 |
| CLIC3 | 219529_at | 0.327 | TCGTTACAGGGAGTCCAACACCGCC | 262 |
| TFPI | 210664_s_at | 0.326 | GATGGTCCGAATGGTTTCCAGGTGG | 263 |
| NACC2 | 212993_at | 0.326 | GTTTTTGTGCTGTTACTCGGTAGAG | 264 |
| TGFBI | 201506_at | 0.325 | GAGATGTGAGCCTTGTGCATGTGGG | 265 |
| IER3 | 201631_s_at | 0.325 | TGAGATCCGTGAGATCCTTCCATCT | 266 |
| MICA | 205904_at | 0.325 | TATTATTTTCTATGTCCGTTGTTGT | 267 |
| BTN3A2 | 212613_at | 0.325 | TACTGGGCAAGTGCTTGTCAAGTTC | 268 |
| IQGAP1 | 200791_s_at | 0.323 | GAGGATGCCCCAACAAACTCATGGC | 269 |
| CNN2 | 201605_x_at | 0.321 | TCTGAGTTGTTGGGGCTAAGCCTGA | 270 |
| TNFAIP8 | 208296_x_at | 0.321 | GAAAGGTAACAATCTTCATTCTACA | 271 |
| VEGFA | 211527_x_at | 0.321 | ATCGATACAGAAACCACGCTGCCGC | 272 |
| MBNL1 | 201152_s_at | 0.32 | ACTCTTGAGGGTTGATTATGCTGCA | 273 |
| ISG15 | 205483_s_at | 0.318 | CCCTGAGCACCGTGTTCATGAATCT | 274 |
| TNFAIP8 | 210260_s_at | 0.318 | GATTGAGTCATCGACATTCAGGATT | 275 |
| COPG1 | 217749_at | 0.318 | CACCCGGGACTACTTGCTGGTGACT | 276 |
| CD99 | 201028_s_at | 0.317 | TGGAGAAAATGACGACCCACGACCA | 277 |
| PSMB9 | 204279_at | 0.317 | GACAGCCTTTTGCCATTGGTGGCTC | 278 |
| ZFP36L1 | 211962_s_at | 0.317 | GGCCTTTCACAACTAGGACTGAGAA | 279 |
| IL6ST | 212196_at | 0.317 | TATGTAATGTACACCTGCCCTAAGG | 280 |
| SHC1 | 214853_s_at | 0.316 | GGGAGAGTTGACCGTTTTCATCCTG | 281 |
| GSTK1 | 217751_at | 0.316 | CATAAGGCACTGGGACTCGGATTTC | 282 |
| CAV1 | 203065_s_at | 0.315 | GCACATCTGGGCAGTTGTACCATGC | 283 |
| HLA-F | 204806_x_at | 0.314 | CACTGACAGTGCCCAGGGCTCTGGG | 284 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Cor-relation | Probe sequence | SEQ ID no |
|---|---|---|---|---|
| KRT7 | 209016_s_at | 0.314 | GAGTGGGAGCCGTGAATATCTCTGT | 285 |
| TFPI | 209676_at | 0.314 | AAATTATCATACTACCGGCTACATC | 286 |
| SPTBN1 | 212071_s_at | 0.314 | TAATTTGCTTCATTTCCTTGCTATT | 287 |
| RHOG | 203175_at | 0.313 | AAGGTGAATGTACCCTAACCTGCTC | 288 |
| CDH11 | 207173_x_at | 0.313 | GAGCATCAATCTTGTTACTGCTGAT | 289 |
| ABCC3 | 208161_s_at | 0.313 | GATCCCCAAGTGGTGAATGACACGC | 290 |
| CAV1 | 212097_at | 0.313 | GTTACCTACTTTGACTTTTTGCATT | 291 |
| HLA-J | 217436_x_at | 0.313 | GAACGGGAAGGAGACGCTGCAGCGC | 292 |
| MYL12A | 201319_at | 0.312 | CAGACTGGAAACGGGACTTTCTATT | 293 |
| MRPS10 | 218106_s_at | 0.312 | AACCCCAGAGAAGTGCTTCATTTTC | 294 |
| RRAS | 212647_at | 0.309 | GACGAGGCTTTTGAGCAGCTGGTGC | 295 |
| TMEM2 | 218113_at | 0.309 | GCAAAATGCCTTTACGTTGTTCTAA | 296 |
| SIDT2 | 218765_at | 0.308 | GGGTCTGGATCTTTTCTCAGAGCGT | 297 |
| RAB11FIP1 | 219681_s_at | 0.308 | GGATTTCGTTTGCTGTGGCATTGGT | 298 |
| RTP4 | 219684_at | 0.308 | AACATCTGTGTCTTTATTTTGCTGC | 299 |
| LOC101928916 NNMT | 202238_s_at | 0.307 | TCCCCAGTGGTGACCTATGTGTGTG | 300 |
| SPTBN1 | 200671_s_at | 0.306 | ATGACAGTTTCACAACCTGCATTGA | 301 |
| TMEM189 TMEM189-UBE2V1 UBE2V1 UBE2V2 | 201003_x_at | 0.306 | GGGAACTTACTTCTCTATAGCCCAC | 302 |
| RPN2 | 213399_x_at | 0.305 | GCTCCTAGCACGATTATATTTCACC | 303 |
| ITGA5 | 201389_at | 0.304 | CACTAACTATGCATGGTGCCCCAGG | 304 |
| CDC42EP1 | 204693_at | 0.304 | GGCTTGCTCTGGGACTTTTATGCTC | 305 |
| BTN3A3 | 204821_at | 0.304 | GAGAATAACCTCATAGTACCAACAT | 306 |
| OSER1 | 209020_at | 0.304 | GGCTCCAGAACGAAGATCCACACTT | 307 |
| CHST15 | 203066_at | 0.303 | GGATTTTTCTTATGCACTCCTATGC | 308 |
| MDFIC | 211675_s_at | 0.303 | AAACATGTACTGGCACAATTTGTGA | 309 |
| CAV2 | 203324_s_at | 0.302 | AAGGCAGACAGTTTTGCTTTAGTAC | 310 |
| CARD10 | 210026_s_at | 0.302 | ACGGGCCTTTTTCACTTAGAAGCTG | 311 |
| RAC2 | 213603_s_at | 0.302 | GAGTGTCTCAGAAGTGTGCTCCTCT | 312 |
| MLPH | 218211_s_at | 0.302 | GCTCTGTGCTTTCCACTATACACAG | 313 |
| F2R | 203989_x_at | 0.301 | GGTTGAAACATATCTCTTATCTTAC | 314 |
| ICAM3 | 204949_at | 0.301 | TGGTACTTATCAGTGCCAAGCGTCC | 315 |
| CRIM1 LOC101929500 | 202552_s_at | 0.3 | GTAAGAGAATTATCTGCAACTTGAT | 316 |
| IFI16 | 208966_x_at | 0.3 | TTCATAGTCACATCAAGGTCATCAA | 317 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Cor-relation | Probe sequence | SEQ ID no |
|---|---|---|---|---|
| EVI2B | 211742_s_at | 0.3 | GGAACTATCTGAAATCTGCTCAGAG | 318 |
| PFKFB3 | 202464_s_at | 0.299 | GCAGTTGCCAGACCAATAAAATACC | 319 |
| MIR6513 TMBIM1 | 217730_at | 0.299 | GGGAGATACCGAAGCCTACTGTGGT | 320 |
| APOL3 | 221087_s_at | 0.299 | TGGAAGTGTATCTCAGTCAGCCAGT | 321 |
| CD55 | 201925_s_at | 0.298 | GATCTGTAATGTTATTTCCACTTAT | 322 |
| TRAM2 | 202369_s_at | 0.298 | TTTTCTACTCTAGCCTGTTCATATG | 323 |
| S100A4 | 203186_s_at | 0.297 | GGCTTCCCAGATAAGCAGCCCAGGA | 324 |
| SERPINB1 | 212268_at | 0.297 | GTGGACTAAACCTGAGAATCTCGAT | 325 |
| PIP4K2A | 212829_at | 0.297 | GTGGTTTGACCCAAGACCACAACCA | 326 |
| RPN2 | 213491_x_at | 0.297 | GGTGAGCTCAGATAGTCTCTTTCTC | 327 |
| ALDOA | 214687_x_at | 0.297 | TCGTCTCTAACCACGCCTATTAAGC | 328 |
| IFIT3 | 204747_at | 0.296 | GCATAGGCAGTATTTTCCTGTCAGC | 329 |
| PLAC8 | 219014_at | 0.296 | AATGAGGACTCTCTACAGGACCCGA | 330 |
| SDF4 | 221972_s_at | 0.296 | CAAGTACAGCGAGTTCTTCACGGGC | 331 |
| CAV2 | 203323_at | 0.294 | GATGGGACGCATAATCATTACCTTA | 332 |
| HLA-C | 216526_x_at | 0.294 | CGATCATCTTTCCTGTTCCAGAGAG | 333 |
| MVP | 202180_s_at | 0.292 | GAGCTCCAGAGGGTCCAGAAGGTCC | 334 |
| RNH1 | 206050_s_at | 0.292 | TCAGCAACAACTGCCTGGGGGACGC | 335 |
| EIF1 | 212225_at | 0.292 | AGGGGTGATAAATGCGTTCATGCTC | 336 |
| SERPINB1 | 213572_s_at | 0.292 | TGCGTAGATTCTTGACCATGTAGTA | 337 |
| ASL | 204608_at | 0.291 | AAGCTGTGTTCATGGCCGAGACCAA | 338 |
| CD99 | 201029_s_at | 0.29 | TGTTCACGGCGGATTCTTTGTTTTA | 339 |
| USP4 | 202682_s_at | 0.289 | GAACATCTTTGACACTCTGCAGACT | 340 |
| TACC1 | 200911_s_at | 0.288 | TTCCCACGGGTGCCATGAAGTGTGT | 341 |
| CD55 | 201926_s_at | 0.288 | GGTCCCACCAACAGTTCAGAAACCT | 342 |
| PDXK | 218019_s_at | 0.288 | GAGGCATCAAAGCACCTGTCGCCTC | 343 |
| BST2 | 201641_at | 0.287 | AACATTCCCTTGATCTCATCAGTTC | 344 |
| LOC101928916 NNMT | 202237_at | 0.287 | CAACAACGAAGGACTTTTCTCCCTG | 345 |
| DUSP5 | 209457_at | 0.287 | TGTGTAGACACCCTCTTGGGTCCAA | 346 |
| TNFSF13 | 210314_x_at | 0.287 | CCACAAGAAGCCTTATCCTACGTCC | 347 |
| COMT | 208818_s_at | 0.286 | TGAGTGCACACACTACCAATCGTTC | 348 |
| CYR61 | 210764_s_at | 0.286 | GATGCGGTTCCGCTGCGAAGATGGG | 349 |
| LY6E | 202145_at | 0.284 | GTCAGTAGGGATGTGTGCCTGGCTG | 350 |
| ACSL5 | 218322_s_at | 0.284 | CTCTCTAGTTAGATATCTGACTTGG | 351 |
| GBP2 | 202748_at | 0.283 | ACAGGGCCCAGTTAATGGCAGAGCA | 352 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Correlation | Probe sequence | SEQ ID no |
|---|---|---|---|---|
| TNFRSF1B | 203508_at | 0.283 | GAAGCGATGAATTTGGAGACTCTGT | 353 |
| PTRF | 208790_s_at | 0.283 | GGGTCCCAGAGGAACGCTGGAGCCA | 354 |
| CYR61 | 201289_at | 0.282 | GGAGCACATGTTACTGCTTCATTTT | 355 |
| BTN3A1 | 209770_at | 0.282 | ATCATTATTATTGCTCTCCACTGTA | 356 |
| PLEC | 201373_at | 0.281 | CATGGGAAGACGAGGCCCTCGGGCC | 357 |
| CTNND1 TMX2-CTNND1 | 208407_s_at | 0.281 | TACCAGGGACTATCTTTGCTGCAGA | 358 |
| TNFRSF14 | 209354_at | 0.281 | GTGAGGCCACAGTCATTGAGGCCCT | 359 |
| ABCC10 | 213485_s_at | 0.281 | GAGCCCACTTGCATTTTCATAGTTT | 360 |
| SELPLG | 209879_at | 0.28 | CACTGCACTGCCATTGTCTTTTGGT | 361 |
| GPX4 | 201106_at | 0.279 | GATCAAAGAGTTCGCCGCGGGCTAC | 362 |
| EDEM1 | 203279_at | 0.279 | AAGAAAATCCTGAGCTTTCCTGTCC | 363 |
| MIR6787 SLC16A3 | 202856_s_at | 0.278 | GATCGTCGCCCGATCAGTGTTTTGA | 364 |
| DMBT1 | 208250_s_at | 0.278 | GCTACCGAGGCTGTGTGTTGAGGTC | 365 |
| PSMB8 | 209040_s_at | 0.278 | TATCGGCCTAATCTTAGCCCTGAAG | 366 |
| FN1 | 214701_s_at | 0.278 | CGTCGACCAATGCCAGGATTCAGAG | 367 |
| COL1A1 | 202310_s_at | 0.277 | CAGACAAGCAACCCAAACTGAACCC | 368 |
| FOS | 209189_at | 0.277 | TCTCCTTAGTCTTCTCATAGCATTA | 369 |
| CYLD | 222142_at | 0.277 | TTCACCACCTGACTTTGAATTTGTC | 370 |
| ADAMTS1 | 222162_s_at | 0.276 | TGGTGAATGTCTGTTCAGCTCTTCT | 371 |
| ALDOA | 200966_x_at | 0.275 | TTCCCTCGTGACAGTGGTGTGTGGT | 372 |
| GATA6 | 210002_at | 0.275 | GACATTCTTATGCTTCTTTTACAAC | 373 |
| YWHAB | 217717_s_at | 0.275 | CCCCCTTTCCTACAGCAATATGTTC | 374 |
| CIB1 | 201953_at | 0.274 | AGACATCAAGTCCCATTATGCCTTC | 375 |
| OPTN | 202074_s_at | 0.273 | GAACAAGTGACTCTGACCAGCAGGC | 376 |
| IFI16 | 208965_s_at | 0.273 | GACCTGGCTGAAACTCTTAAAAAAG | 377 |
| CFLAR | 211316_x_at | 0.273 | TCTTCTGGAGCCTGTGTACTGCGGA | 378 |
| PTGER4 | 204897_at | 0.272 | GATTCCCAAACGTGGTTACATTAGC | 379 |
| CCND1 | 208712_at | 0.272 | AGCAAGCTGCCGAACCAAAAGAATT | 380 |
| PDLIM5 | 212412_at | 0.271 | GGATTCTCAATGTATAAGTTGCCTT | 381 |
| HLA-F | 221875_x_at | 0.271 | AGCTACTCTCAGGCTGCAGTGTGAG | 382 |
| CYP1B1 | 202437_s_at | 0.27 | TTAGCCTTTACCTGTGAAGTGTTAC | 383 |
| SVIL | 202565_s_at | 0.27 | GTTTGCTCTGCATTTTTGATGATGG | 384 |
| RNASET2 | 217983_s_at | 0.27 | GGCCTGACGTAATTCACTCGTTTCC | 385 |
| TAGLN2 | 200916_at | 0.269 | CTGCCTACCATGGTCTGGGGCTTGA | 386 |
| IFI27 | 202411_at | 0.267 | TCTGCCATTGCGGCTGTCATTGCGA | 387 |

TABLE 2-continued

Biomarkers of resistance to stenoparib. Dashes mean that the Affymetrix probeset has not been mapped to a specific gene. Affymetrix IDs refer to the array type HG-U133_Plus_2. All correlations are negative.

| Gene ID | Affymetrix ID | Cor-relation | Probe sequence | SEQ ID no |
|---|---|---|---|---|
| FLII | 212025_s_at | 0.267 | ATCAGACCCTGACGAAGCCAAGTTG | 388 |
| STAT6 | 201331_s_at | 0.266 | GAACATGTGTCTATCTGCTTTTGCC | 389 |
| WWP2 | 204022_at | 0.266 | TCAGGGTGCAAGCTGCTGGTGAGGT | 390 |
| FLNC | 207876_s_at | 0.266 | CTGCGAGGCCAGGGAAGCCCTGAGT | 391 |
| PARP12 | 218543_s_at | 0.266 | TTGTCTCTGCAGTGATTCGGTTTCT | 392 |
| VPS13D | 220221_at | 0.266 | GACTGGCATTTTACTTCTGTGTTTT | 393 |
| IFITM2 | 201315_x_at | 0.265 | ATCATTGAGGCCAGGAGCTCTGCCC | 394 |
| CTSZ | 210042_s_at | 0.265 | ACTGGCTGCGAGTGTTCCTGAGAGT | 395 |
| C19orf10 | 221739_at | 0.265 | GTGAAGCTGAAGGGGCCTGTGTCCC | 396 |
| DAPK1 | 203139_at | 0.264 | TGATCAGTGTTGTTGCTCTAGGAAG | 397 |
| LOC101928189 RSRP1 | 209006_s_at | 0.264 | GTGCATGCTAGAATTTGGGACAGGC | 398 |
| MYOF | 211864_s_at | 0.263 | CTCTACTCTTTGCCGAACTATTTGT | 399 |
| ATP2B4 | 212135_s_at | 0.263 | CGCCCTTTCACTTAGTTCAGTGCCA | 400 |
| AXL | 202686_s_at | 0.262 | ATTGGTCCAAGATTCCGGATCCTAA | 401 |
| MIR6787 SLC16A3 | 202855_s_at | 0.262 | TGTTCGTGGTGAGCTACGCCAAGGA | 402 |
| LY96 | 206584_at | 0.262 | CAGTATTGGGTCTGCAACTCATCCG | 403 |
| FN1 | 212464_s_at | 0.262 | CTGTTCTGCTTCGAAGTATTCAATA | 404 |
| CREB3L1 | 213059_at | 0.261 | TTGTATTTTACAAATCTCCCTCTTC | 405 |
| TNFSF12-TNFSF13 TNFSF13 | 209499_x_at | 0.26 | GTGTCATAATTCCCCGGGCAAGGGC | 406 |
| POFUT2 | 209578_s_at | 0.26 | GTTGCATTTTCCAGGCTGAGAGCTG | 407 |
| WDR1 | 200609_s_at | 0.259 | GTTGCCTGTCAGTGTTTACAAACTA | 408 |
| SLC7A7 | 204588_s_at | 0.259 | TAAAAGGGCCCACAATGCTCCAATT | 409 |
| MICB | 206247_at | 0.259 | ACCGTTATGCATTACTCTGTGTCTA | 410 |
| GATA3 | 209604_s_at | 0.258 | GTGTCTGTGTTCCAACCACTGAATC | 411 |
| LRRFIP1 | 211452_x_at | 0.257 | GAGCTATGATTGCACACTGTACTCT | 412 |
| RNASET2 | 217984_at | 0.256 | TAGATCGTGGCCCTTCAATTTAGAA | 413 |
| ITM2A | 202746_at | 0.255 | GCAAGCTCTTGTCAAATTTTAGTTT | 414 |

RNA Extraction and Biomarker Expression Measurement

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. and compatible apparatus e.g., GCS3000Dx from Affymetrix, using the manufacturer's instructions. Exemplary Affymetrix probes for detecting the genes in Table 1 and Table 2 are described in PCT Patent Publication No. WO 2019/219759 and U.S. Patent Publication No. US 2021/0222252, each of which is incorporated by reference in its entirety. The resulting biomarker expression measurements may be further analyzed as described herein. The procedures described can be implemented using, e.g., R software available from R-Project and supplemented with packages available from Bioconductor.

One or more of the biomarkers shown in Table 1 and/or Table 2 (e.g., SRSF7 and/or HLA-E) may be measured in a biological sample (e.g., a tumor sample) obtained from the cancer subject using, e.g., polymerase chain reaction (PCR), reverse transcriptase PCR (RT-PCR), quantitative real-time PCR (qPCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof. In a particular example, biomarkers for sensitivity or resistance to stenoparib or a pharmaceutically acceptable salt thereof or a hydrate thereof can be measured using any of the methods (e.g., microarray, PCR-based techniques, and/or sequencing) described in PCT Patent Publication No. WO 2019/219759 and U.S. Patent Publication No. US 2021/0222252, each of which is incorporated by reference in its entirety.

Methods of Determining the Responsiveness of a Subject to Stenoparib or a Pharmaceutically Acceptable Salt Thereof or a Hydrate Thereof The disclosure features diagnostic methods for the detection and screening of a subject with a cancer (e.g., a subject with cancer or a recurrence thereof) that may be responsive to stenoparib or a pharmaceutically acceptable salt thereof or a hydrate thereof using one or more of the biomarkers shown in Table 1 and/or Table 2 (e.g., SRSF7 and/or HLA-E). The methods of the disclosure may be used for predicting a subject's responsiveness to stenoparib or a pharmaceutically acceptable salt thereof or a hydrate thereof, and optionally, treating the cancer subject throughout the progression of cancer and/or in cases of recurrence (e.g., after a first line treatment, a second line treatment, and/or a third line treatment).

The disclosure provides individual biomarkers (e.g., SRSF7 or HLA-E) and sets of biomarkers (e.g., two or more of the biomarkers listed in Table 1 and/or Table 2), the expression levels of which, as detected in a biological sample (e.g., a tumor sample, such as a biopsy) obtained from the subject with cancer, are indicative of the responsiveness of the subject to stenoparib or a pharmaceutically acceptable salt thereof or a hydrate thereof. The biomarkers were identified using methods similar to those previously described in, e.g., Chen et al. (*Mol. Cancer Ther.* 11:34-33, 2012), Wang et al. (*J. Nat. Cancer Inst.* 105:1284-1291, 2013), Knudsen et al. (PLOS One, 9: e87415, 2014), and Buhl et al (PLOS One 13 (3): e0194609, 2018), each of which is incorporated by reference herein in their entirety. In particular, an algorithm based on growth inhibition values (GI50) of a cell line (e.g., NCI60 cells) is used. The cell line is subjected to treatment with stenoparib or a pharmaceutically acceptable salt thereof or a hydrate thereof and baseline gene expression is determined (e.g., by microarray analysis, RT-PCR, qPCR, or next generation sequencing). After normalization, genes with, e.g., a Pearson correlation coefficient greater than 0.25 or below-0.25 were classified as biomarkers of sensitivity or resistance, respectively. In particular, a correlation coefficient of 0.25 or greater was used as a statistically significant cut-off for establishing that the expression levels of, e.g., the genes shown in Table 1 and/or Table 2, correlate with the likelihood of cancer treatment sensitivity, such as sensitivity to stenoparib or a pharmaceutically acceptable salt thereof or a hydrate thereof, as described in van't Veer et al. *Nature* 415 (6871): 530-536, 2002, hereby incorporated by reference.

Thus, after normalization, expression levels of one or more of the biomarkers shown in Table 1 and/or Table 2 in a sample (e.g., a tumor sample) from a subject that are above a cutoff value of the 50th percentile in a reference population with the same diagnosis as the subject, or greater (e.g., 60th percentile, 70th percentile, or 80th percentile, or greater), indicate sensitivity and/or resistance, respectively, of the subject to treatment with stenoparib or a pharmaceutically acceptable salt thereof or a hydrate thereof.

Additionally, the predicted responsiveness of a cancer subject may be determined from, e.g., the difference score, which is the difference between the mean score (e.g., the mean of the expression level) of the one or more biomarkers of sensitivity of Table 1 (e.g., SRSF7) and the mean score (e.g., mean of the expression level) of the one or more biomarkers of resistance of Table 2 (e.g., HLA-E). The difference score of the cancer subject can then be compared to the difference score in a cell (e.g., a cancer cell) or tissue (e.g., a tumor tissue) known to be sensitive or resistant to treatment with stenoparib or a pharmaceutically acceptable salt thereof or a hydrate thereof.

For example, the cancer subject may be determined to be responsive to treatment with stenoparib or a pharmaceutically acceptable salt thereof or a hydrate thereof if the difference score is above a cutoff value of about 0.3 (e.g., about 0.3, about 0.35, about 0.4, about 0.45, about 0.5, about 0.55, about 0.6, about 0.65, about 0.7, or more). Alternatively, the cancer subject may be determined to be non-responsive to treatment with stenoparib or a pharmaceutically acceptable salt thereof or a hydrate thereof if the difference score is below a cutoff value of about 0.3 (e.g., about 0.29, about 0.28, about 0.27, about 0.26, about 0.2, about 0.15, about 0.1, about 0.05, about 0.02, about 0.01, or less).

Additionally, the mean score (i.e., mean of the expression level) of the one or more biomarkers of sensitivity of Table 1 and/or the mean score (i.e., mean of the expression level) of the one or more biomarkers of resistance of Table 2 can be used to predict responsiveness of a cancer subject (e.g., a subject with cancer recurrence) to stenoparib or a pharmaceutically acceptable salt thereof or a hydrate thereof. After determining the mean score of the biomarker(s) in a sample (e.g., a tumor sample) from the cancer subject, the mean score of the biomarker(s) in the sample may be compared to the mean score of the biomarker(s) in a cell (e.g., a cancer cell) or tissue (e.g., a tumor tissue) known to be sensitive to treatment with stenoparib or a pharmaceutically acceptable salt thereof or a hydrate thereof.

For example, the cancer subject (e.g., a subject with cancer recurrence) may be determined to be responsive to treatment with stenoparib or a pharmaceutically acceptable salt thereof or a hydrate thereof if the mean score (i.e., mean of the expression level) of the one or more biomarkers of sensitivity of Table 1 is above a cutoff value of about 0.3 (e.g., about 0.3, about 0.35, about 0.4, about 0.45, about 0.5, about 0.55, about 0.6, about 0.65, about 0.7, or more). Alternatively, the cancer subject (e.g., a subject with cancer recurrence) may be determined to be non-responsive to treatment with stenoparib or a pharmaceutically acceptable salt thereof or a hydrate thereof if the mean score of the one or more biomarkers of sensitivity of Table 1 is below a cutoff value of about 0.3 (e.g., about 0.29, about 0.28, about 0.27, about 0.26, about 0.2, about 0.15, about 0.1, about 0.05, about 0.02, about 0.01, or less). Additionally, the cancer subject (e.g., a subject with cancer recurrence) may be determined to be non-responsive to treatment with stenoparib or a pharmaceutically acceptable salt thereof or a hydrate thereof if the mean score (i.e., mean of the expression level) of the one or more biomarkers of resistance of Table 2 is above a cutoff value of about 0.3 (e.g., about 0.3, about 0.35, about 0.4, about 0.45, about 0.5, about 0.55, about 0.6, about 0.65, about 0.7, or more). Alternatively, the cancer subject (e.g., a subject with cancer recurrence) may be determined to be responsive to treatment with stenoparib or a pharmaceutically acceptable salt thereof or a hydrate thereof if the mean score of the one or more biomarkers of resistance of Table 2 is below a cutoff value of about 0.3 (e.g., about 0.29, about 0.28, about 0.27, about 0.26, about 0.2, about 0.15, about 0.1, about 0.05, about 0.02, about 0.01, or less).

In a particular example, the level(s) of any of the biomarkers from Table 1 and/or Table 2, the difference score, and/or the mean score can be used to predict sensitivity or resistance to treatment of a cancer using stenoparib or a pharmaceutically acceptable salt thereof or a hydrate thereof using any of the methods (e.g., analytical methods) described in PCT Patent Publication No. WO 2019/219759A1 and U.S. Patent Publication No. US 2021/0222252A1, each of which is incorporated by reference in its entirety.

DRP® Companion Diagnostic for Dovitinib

The methods described herein include administration of stenoparib and dovitinib combination therapy to a subject having a cancer who may have sensitivity or resistance to treatment including dovitinib or a pharmaceutically acceptable salt thereof or a hydrate thereof. The methods may include determining, prior to therapy, whether the subject is likely to respond to the therapy, e.g., using a DRP® companion diagnostic for dovitinib.

A cancer subject can be assessed for sensitivity or resistance to dovitinib or a pharmaceutically acceptable salt thereof or a hydrate thereof by detecting gene expression of a biomarker (e.g., one or more of the biomarkers of Table 3 and/or Table 4) in a biological sample obtained from the cancer subject (e.g., a subject with the cancer or a recurrence thereof). The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., lymph nodes, thymus, spleen, bone marrow, breast, colorectal, pancreatic, cervical, prostate, bladder, lung, gastrointestinal, head, neck, or ovarian tissue).

Table 3 below lists biomarkers for sensitivity to treatment with to dovitinib or a pharmaceutically acceptable salt thereof or a hydrate thereof, which are included in the dovitinib-DRP® companion diagnostic. Table 4 below lists biomarkers for resistance to treatment with to dovitinib or a pharmaceutically acceptable salt thereof or a hydrate thereof, which are included in the dovitinib-DRP® companion diagnostic.

TABLE 3

Biomarkers of sensitivity to dovitinib. Dashes mean that the Affymetrix probeset has not been mapped to a specific gene. Affymetrix IDS refer to the array type HG-U133_Plus 2

| Gene | Affymetrix ID | Correlation | Affymetrix Probe Sequence | SEQ ID NO: |
|---|---|---|---|---|
| DDIT4 | 202887_s_at | 0.563 | GGCAGCTATCTTACAGACGCATGAA | 415 |
| ZNF395 | 218149_s_at | 0.331 | GTCCAGCGAATGACGTCTGTGGCCA | 416 |
| IncRNA | 216246_at | 0.326 | AGTCAATGAGTCGCTTGTGAATTCT | 417 |
| LSM4 | 202736_s_at | 0.307 | GAGCTGCGACAACTGGATGAACATT | 418 |
| SEL1L3 | 212314_at | 0.301 | TATTTTGGTACCTGTGCTTGCCACA | 419 |
| FABP5 | 202345_s_at | 0.296 | CAACACAGTTTTCTTGTACCCTGGG | 420 |
| TRIM22 | 213293_s_at | 0.293 | TGAGGTCAAATTTTATCTTTTCACT | 421 |
| TPK1 | 221218_s_at | 0.293 | TCATTACTTTCTGCTTGACCGGAAG | 422 |
| SLC16A3 | 202856_s_at | 0.291 | GAGTGGATCTGCGGTGAAGCCAAGC | 423 |
| INSIG1 | 201626_at | 0.288 | CAATAAGTCTTTCTCTCCGAAACCG | 424 |
| HOXA10-HOXA9 HOXA9 MIR196B | 214651_s_at | 0.284 | AATGCGGGCATTTAAGTCTGTCCAT | 425 |
| DPP4 | 203716_s_at | 0.281 | AAAGCCCTGGTCGATGTTGGAGTGG | 426 |
| LDLR | 202068_s_at | 0.277 | AGAATGATGTCCCCGTTGTATGTAT | 427 |
| HSPE1 | 205133_s_at | 0.275 | TAGAAAGTTTCTTCCACTCTTTGAC | 428 |
| VEGFA | 212171_x_at | 0.274 | GGAGACCTGGTTGTGTGTGTGTGAG | 429 |
| TMSB10 | 217733_s_at | 0.272 | AAGAGCCACCTGCAAGATGGACACG | 430 |
| SLC16A3 | 202855_s_at | 0.271 | TGTTCGTGGTGAGCTACGCCAAGGA | 431 |

TABLE 3-continued

Biomarkers of sensitivity to dovitinib. Dashes mean that the Affymetrix probeset has not been mapped to a specific gene. Affymetrix IDS refer to the array type HG-U133_Plus 2

| Gene | Affymetrix ID | Correlation | Affymetrix Probe Sequence | SEQ ID NO: |
|---|---|---|---|---|
| VEGFA | 210512_s_at | 0.271 | GAATTCTACATACTAAATCTCTCTC | 432 |
| CAV2 | 203323_at | 0.269 | GATGAGCAGACTTCTCGGAATTCAT | 433 |
| P4HA1 | 207543_s_at | 0.267 | AACTAGGACACTAACTGGGTTCCAT | 434 |
| APOL1 | 209546_s_at | 0.265 | GTCCCCTGCTTGAACACTGAAGGGC | 435 |
| CAV2 | 203324_s_at | 0.264 | AAATGTTGCTCTAATCAGATTGCTT | 436 |
| PTPRE | 221840_at | 0.263 | GACACCTGTGTTTCAGCATTTGGAG | 437 |
| DPYSL2 | 200762_at | 0.262 | GACCCATGAGTGGAGGAACTTTCAG | 438 |
| ANP32B | 201305_x_at | 0.262 | ATGACCTGCAGAAACAGAACTGTTC | 439 |
| STAT6 | 201331_s_at | 0.26 | GCTGGCACCTTAGTTGCATGACCAC | 440 |
| RPL27A SNORA3 | 203034_s_at | 0.259 | TCTGCCCAACTGTCAACCTTGACAA | 441 |
| EPB41L2 | 201719_s_at | 0.258 | GTTATACCATTTAAAGCTGGCACCA | 442 |
| RPL38 | 202028_s_at | 0.255 | AAAGGTATCTGCTGCATCGAACTTT | 443 |
| RNU86 RPL3 SNORD83B | 211073_x_at | 0.253 | TTAAGTTCATTGACACCACCTCCAA | 444 |

TABLE 4

Biomarkers of resistance to dovitinib. Dashes mean that the Affymetrix probeset has not been mapped to a specific gene. Affymetrix IDs refer to the array type HG-U133_Plus_2. All correlations are negative.

| Gene ID | Affymetrix ID | Correlation | Probe sequence | SEQ ID no |
|---|---|---|---|---|
| SCAMP3 | 201771_at | −0.397 | CTGCTCTGGTGGTGCCGAAGGGCAA | 445 |
| BAG5 | 202985_s_at | −0.329 | GATTGACTGTCAGGCATGGCTTTGT | 446 |
| ABCF1 | 200045_at | −0.325 | CTGATTTACCCTACAGCTTCAGGCC | 447 |
| MARCH6 | 201736_s_at | −0.313 | TAGCTTCTGGTGTTGTTCCTTTACT | 448 |
| EMC3 | 217882_at | −0.312 | GAGCTACTCACATTAGATGCATCCT | 449 |
| UCP2 | 208998_at | −0.304 | GAAAGTTCAGCCAGAATCTTCGTCC | 450 |
| TUG1 | 212337_at | −0.295 | ATACAGCAGTTCGAAAGCCGCGTCC | 451 |
| CLPTM1 | 211136_s_at | −0.286 | TTCATCTACCTCTACCAACGGTGGA | 452 |
| IGFBP5 | 211958_at | −0.285 | AGGAGGCTCCGTTTTGCAAAGTGGA | 453 |
| MAGEA1 | 207325_x_at | −0.278 | CTCAGTAGTAGGTTTCTGTTCTATT | 454 |
| ATM | 208442_s_at | −0.278 | CATTACGGGTGTTGAAGGTGTCTTC | 455 |
| GATA3 | 209602_s_at | −0.278 | CTGCTAGTCTTAAGAACTGCTTTCT | 456 |
| SPDEF | 220192_x_at | −0.278 | GGAAAACGGGCAGTCTGCTCTGCTG | 457 |
| LDOC1 | 204454_at | −0.276 | GCCGTTCAGCCTGGTTAGTTTTCTA | 458 |
| HRAS | 212983_at | −0.276 | GACTGTCTTGAACATCCCAAATGCC | 459 |

TABLE 4-continued

Biomarkers of resistance to dovitinib. Dashes mean that the Affymetrix probeset has not been mapped to a specific gene. Affymetrix IDs refer to the array type HG-U133_Plus_2. All correlations are negative.

| Gene ID | Affymetrix ID | Correlation | Probe sequence | SEQ ID no |
|---|---|---|---|---|
| SRM | 201516_at | -0.275 | TCGCCCACCAACCAAGTGTTACAAG | 460 |
| ZNF331 | 219228_at | -0.274 | CGCTTTCCACAGTTTGTTACCTGCA | 461 |
| GATA3 | 209604_s_at | -0.272 | GGACAAACTGCCAGTTTTGTTTCCT | 462 |
| TOB1 | 202704_at | -0.271 | CTCTCAGATATGGCCTCTTACAGTA | 463 |
| APITD1 CORT | 213454_at | -0.271 | CTTAAGCAAAATACTCCCAGGTCTC | 464 |
| NDUFV1 | 208714_at | -0.27 | GCACAGCTGCGGTGATCGTCATGGA | 465 |
| BAG6 | 213318_s_at | -0.27 | GTGGTATGCCTGCCAAGAGACGCAA | 466 |
| CUL3 | 201371_s_at | -0.269 | TATTCTTGGACTGTACTCTTCGCAT | 467 |
| CCDC90A | 220094_s_at | -0.268 | GAAATCATTGTGTCTGCATTGGTCA | 468 |
| CERS2 | 222212_s_at | -0.262 | GTAGGGGTTACAATTCACATTCCTT | 469 |
| LOC100506032 NBPF10 NBPF11 NBPF12 NBPF15 NBPF16 NBPF24 NBPF7 NBPF8 NBPF9 | 201103_x_at | -0.26 | GGTCTAGGAGATCTGTCCCTTTTAG | 470 |
| PPP1R11 | 201500_s_at | -0.258 | CCATACCACCACTGAGATCTCATTT | 471 |
| CKB | 200884_at | -0.254 | GAAGCGAGGCACAGGCGGTGTGGAC | 472 |

RNA Extraction and Biomarker Expression Measurement

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. and compatible apparatus e.g., GCS3000Dx from Affymetrix, using the manufacturer's instructions. The Affymetrix array typically contains 11 probes (also known as a probe set) specific to each gene. In general, confidence in a prediction of responsiveness or non-responsiveness increases with an increase in the number of probes used in the analysis. Exemplary Affymetrix probes for detecting the genes in Table 3 and Table 4 are described in PCT Patent Publication No. WO 2020/254383 and U.S. Pat. No. 10,835,531, each of which is incorporated by reference in its entirety. The resulting biomarker expression measurements may be further analyzed as described herein. The procedures described can be implemented using, e.g., R software available from R-Project and supplemented with packages available from Bioconductor.

One or more of the biomarkers shown in Table 3 and/or Table 4 (e.g., DDIT4) and/or SCAMP3) may be measured in a biological sample (e.g., a tumor sample) obtained from the cancer subject (e.g., a subject with any of the cancer types described herein, such as a subject with recurrence of cancer) using, e.g., polymerase chain reaction (PCR), reverse transcriptase PCR (RT-PCR), quantitative real-time PCR (qPCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof. In a particular example, biomarkers for sensitivity or resistance to dovitinib or a pharmaceutically acceptable salt thereof or a hydrate thereof can be measured using any of the methods (e.g., microarray, PCR-based techniques, and/or sequencing) described in PCT Patent Publication No. WO 2020/254383 and U.S. Pat. No. 10,835,531, each of which is incorporated by reference in its entirety Methods of Determining the Responsiveness of a Subject to Dovitinib or a Pharmaceutically Acceptable Salt Thereof or a Hydrate Thereof The disclosure features diagnostic methods for the detection and screening of cancer subjects (e.g., subjects with cancer or a recurrence thereof) that may be responsive to dovitinib or a pharmaceutically acceptable salt thereof or a hydrate thereof using one or more of the biomarkers shown in Table 3 and/or Table 4 (e.g., DDIT4) and/or SCAMP3). The methods of the disclosure may be used for predicting a subject's responsiveness to dovitinib or a pharmaceutically acceptable salt thereof or a hydrate thereof, and optionally, treating the cancer subject throughout the progression of cancer and/or in cases of recurrence (e.g., after a first line treatment, a second line treatment, and/or a third line treatment).

The disclosure provides individual biomarkers (e.g., DDIT4 or SCAMP3) and sets of biomarkers (e.g., two or more of the biomarkers listed in Table 3 and/or Table 4), the expression levels of which, as detected in a biological sample (e.g., a tumor sample, such as a biopsy) obtained from a cancer subject (e.g., a human with cancer), are indicative of responsiveness to dovitinib or a pharmaceutically acceptable salt thereof or a hydrate thereof. The biomarkers were identified using methods similar to those previously described in, e.g., Chen et al. (*Mol. Cancer Ther.* 11:34-33, 2012), Wang et al. (*J. Nat. Cancer Inst.* 105:1284-1291, 2013), and Knudsen et al. (PLOS One, 9: e87415, 2014), Buhl et al (PLOS One 13 (3): e0194609, 2018) each of which are incorporated by reference herein in their entirety. In particular, an algorithm based on growth inhibition values (GI50) of a cell line (e.g., NCI60 cells) is used. The cell line is subjected to treatment with dovitinib or a pharmaceutically acceptable salt thereof or a hydrate thereof and baseline gene expression is determined (e.g., by microarray analysis, RT-PCR, qPCR, or next generation sequencing). After normalization, genes with, e.g., a Pearson correlation coefficient greater than 0.25 or below-0.25 were classified as biomarkers of sensitivity or resistance, respectively. In particular, a correlation coefficient of 0.25 or greater was used as a statistically significant cut-off for establishing whether the expression levels of, e.g., the genes shown in Table 3 and/or Table 4, correlate with the likelihood of cancer treatment sensitivity, such as sensitivity to dovitinib or a pharmaceutically acceptable salt thereof or a hydrate thereof, as described in van't Veer et al. *Nature* 415 (6871): 530-536, 2002, hereby incorporated by reference.

Thus, after normalization, expression levels of one or more of the biomarkers shown in Table 3 and/or Table 4 in a sample (e.g., a tumor sample) from a subject that are above a cutoff value of the 50th percentile in a reference population with the same diagnosis as the subject, or greater (e.g., 60th percentile, 70th percentile, or 80th percentile, or greater), indicate sensitivity and/or resistance, respectively, of the subject to treatment with dovitinib or a pharmaceutically acceptable salt thereof or a hydrate thereof.

Additionally, the predicted responsiveness of a cancer subject may be determined from, e.g., the difference score, which may be defined as the difference between the mean score (e.g., mean of the expression level) of the one or more biomarkers of sensitivity of Table 3 (e.g., DDIT4) and the mean score (e.g., mean of the expression level) of the one or more biomarkers of resistance of Table 4 (e.g., SCAMP3). The difference score of the cancer subject can then be compared to the difference score in a cell (e.g., a cancer cell) or tissue (e.g., a tumor tissue) known to be sensitive or resistant to treatment with dovitinib or a pharmaceutically acceptable salt thereof or a hydrate thereof.

For example, the cancer subject (e.g., a subject with cancer recurrence) may be determined to be responsive to treatment with dovitinib or a pharmaceutically acceptable salt thereof or a hydrate thereof if the difference score is compared to a score from a reference population (e.g., a score determined using a tumor sample(s) from subjects diagnosed with the same type(s) of tumor as the subject), in which an expression level at the 50th percentile of the reference population, or the 60th percentile, or the 70th percentile, or the 80th percentile, or the 90th percentile, or greater, indicates that the sample (or the subject from whom the sample was taken) is predicted to be responsive to treatment with dovitinib or a pharmaceutically acceptable salt thereof or a hydrate thereof. The confidence of the prediction increases as the percentile level increases (e.g., an expression level above the 90th percentile of a reference population indicates a greater likelihood of treatment responsiveness than an expression level at the 50th percentile). Conversely, an expression level in the tested sample of below the 50th percentile of the reference population indicates that the sample (or the subject from whom the sample was taken) is predicted to be non-responsive to treatment with dovitinib or a pharmaceutically acceptable salt thereof or a hydrate thereof.

Additionally, the mean score (i.e., mean of the expression level) of the one or more biomarkers of sensitivity of Table 3 and/or the mean score (i.e., mean of the expression level) of the one or more biomarkers of resistance of Table 4 can be used to predict responsiveness of a cancer subject (e.g., a subject with cancer recurrence) to dovitinib or a pharmaceutically acceptable salt thereof or a hydrate thereof. After determining the mean score of the biomarker(s) in a sample (e.g., a tumor sample) from the cancer subject, the mean score of the biomarker(s) in the sample may be compared to the mean score of the biomarker(s) in a cell (e.g., a cancer cell) or tissue (e.g., a tumor tissue) known to be sensitive to treatment with dovitinib or a pharmaceutically acceptable salt thereof or a hydrate thereof. If the mean score of the biomarker(s) in the sample from the cancer subject is substantially similar to the mean score of the biomarker(s) in the cell or tissue known to be sensitive to dovitinib or a pharmaceutically acceptable salt thereof or a hydrate thereof, then the cancer subject is predicted to be responsive to treatment with dovitinib or a pharmaceutically acceptable salt thereof or a hydrate thereof. Alternatively, if the mean score of the biomarker(s) in the sample from the cancer subject is substantially dissimilar to the mean score of the biomarker(s) in the cell or tissue known to be sensitive to dovitinib or a pharmaceutically acceptable salt thereof or a hydrate thereof, then the cancer subject is predicted to be non-responsive to treatment with dovitinib or a pharmaceutically acceptable salt thereof or a hydrate thereof.

For example, the cancer subject (e.g., a subject with cancer recurrence) may be determined to be responsive to treatment with dovitinib or a pharmaceutically acceptable salt thereof or a hydrate thereof if the mean score (i.e., mean of the expression level) of the one or more biomarkers of sensitivity of Table 3 is compared to a mean score from a reference population (e.g., a mean score determined using a tumor sample(s) from subjects diagnosed with the same type(s) of tumor as the subject), in which an expression level at the 50th percentile of the reference population, or the 60th percentile, or the 70th percentile, or the 80th percentile, or the 90th percentile, or greater, indicates that the sample (or the subject from whom the sample was taken) is predicted to be responsive to treatment with dovitinib or a pharmaceutically acceptable salt thereof or a hydrate thereof. Conversely, an expression level in the tested sample of below the 50th percentile of the reference population indicates that the sample (or the subject from whom the sample was taken) is predicted to be non-responsive to treatment with dovitinib or a pharmaceutically acceptable salt thereof or a hydrate thereof.

Alternatively, the cancer subject (e.g., a subject with cancer recurrence) may be determined to be non-responsive to treatment with dovitinib or a pharmaceutically acceptable salt thereof or a hydrate thereof if the mean score (i.e., mean of the expression level) of the one or more biomarkers of resistance of Table 4 is compared to a mean score from a reference population (e.g., a mean score determined using a tumor sample(s) from subjects diagnosed with the same type(s) of tumor as the subject), in which an expression level at the 50th percentile of the reference population, or the 60th percentile, or the 70th percentile, or the 80th percentile, or the 90th percentile, or greater, indicates that the sample (or the subject from whom the sample was taken) is predicted to be non-responsive to treatment with dovitinib or a pharmaceutically acceptable salt thereof or a hydrate thereof.

In a particular example, the level(s) of any of the biomarkers from Table 3 and/or Table 4 can be used to predict sensitivity or resistance to treatment of a cancer using dovitinib or a pharmaceutically acceptable salt thereof or a hydrate thereof using any of the methods (e.g., analytical methods) described in PCT Patent Publication No. WO 2020/254383 and U.S. Pat. No. 10,835,531, each of which is incorporated by reference in its entirety.

Kits

A dosage form of stenoparib or a pharmaceutically acceptable salt thereof or a hydrate thereof and/or a dosage form of dovitinib or a pharmaceutically acceptable salt thereof or a hydrate thereof described herein may be provided in a kit. The kit may include (a) a compound used in a method described herein (e.g., stenoparib or a pharmaceutically acceptable salt thereof or a hydrate thereof or dovitinib or a pharmaceutically acceptable salt thereof or a hydrate thereof), and, optionally (b) informational material. Alternatively, the kit may include (a) stenoparib or a pharmaceutically acceptable salt thereof or a hydrate thereof, b) dovitinib or a pharmaceutically acceptable salt thereof or a hydrate thereof, and optionally, (c) informational material. The informational material can be descriptive, instructional, marketing, or other material that relates to the methods described herein and/or the use of the dosage form for the methods described herein. The informational material may contain methods described herein directed to a combination therapy of stenoparib and dovitinib or pharmaceutically acceptable salts thereof and/or use of the dosage form for the methods described herein directed to a combination therapy of stenoparib and dovitinib or pharmaceutically acceptable salts thereof.

The informational material of the kit is not limited in its form. In one instance, the informational material can include information about production of the compound(s), molecular weight of the compound, concentration, date of expiration, batch or production site information, and so forth. In one instance, the informational material relates to methods for administering the compound (e.g., stenoparib or a pharmaceutically acceptable salt thereof or a hydrate thereof and/or dovitinib or a pharmaceutically acceptable salt thereof or a hydrate thereof).

In addition to a dosage form described herein, the kit can include other components or ingredients, such as a container (s) of a solvent or buffer, a stabilizer, a preservative, a flavoring agent (e.g., a bitter antagonist or a sweetener), a fragrance, a dye or coloring agent, for example, to tint or color one or more components in the kit. Other component (s) can be included in the kit, but in different compositions or containers distinct from the composition or containing with stenoparib or a pharmaceutically acceptable salt thereof or a hydrate thereof and/or dovitinib or a pharmaceutically acceptable salt thereof or a hydrate thereof. In such instances, the kit can include instructions for admixing a compound described herein (e.g., stenoparib or a pharmaceutically acceptable salt thereof or a hydrate thereof) and a different compound described herein (e.g., dovitinib or a pharmaceutically acceptable salt thereof or a hydrate thereof), or for using a compound described herein (e.g., stenoparib or a pharmaceutically acceptable salt thereof or a hydrate thereof and/or dovitinib or a pharmaceutically acceptable salt thereof or a hydrate thereof) together with the other component(s).

In some instances, the components of the kit are stored under inert conditions (e.g., under nitrogen or another inert gas such as argon). In some instances, the components of the kit are stored under anhydrous conditions (e.g., with a desiccant). In some instances, the components are stored in a light blocking container, such as an amber vial.

A dosage form described herein can be provided in any form, e.g., liquid, dried or lyophilized form. The compounds described herein may be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a dosage form described herein. In some instances, the kit contains separate containers, dividers or compartments for the composition and informational material. For example, the composition can be contained in a bottle, vial, or syringe, and the informational material can be contained in a plastic sleeve or packet. In other instances, the separate elements of the kit are contained within a single, undivided container. For example, the dosage form is contained in a bottle, vial or syringe that has attached thereto the informational material in the form of a label. In some instances, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a dosage form described herein.

The containers of the kits can be airtight, waterproof (e.g., impermeable to changes in moisture or evaporation), and/or light-tight.

The kit optionally includes a device suitable for delivery of the dosage form, e.g., a syringe, pipette, forceps, measured spoon, swab (e.g., a cotton swab or wooden swab), or any such device.

The kits of the disclosure can include dosage forms of varying strengths to provide a subject with doses suitable for one or more of the initiation phase regimens, induction phase regimens, or maintenance phase regimens described herein. Alternatively, the kit can include a scored tablet to allow the user to administer divided doses, as needed.

EXAMPLES

The following examples, which are intended to illustrate, rather than limit, the disclosure, are put forth to provide those of ordinary skill in the art with a description of how the compositions and methods described herein may be used, made, and evaluated. The examples are intended to be purely exemplary of the disclosure and are not intended to limit the scope of what the inventors regard as their invention.

Example 1. Treatment of Cancer with BID Dosing Stenoparib Monotherapy

Stenoparib potently inhibits both PARP1 and PARP2 in cell-free assays in vitro. Human recombinant PARP1 and mouse recombinant PARP2 were inhibited with IC50 values of 1.0 and 1.2 nmol/L, respectively.

The effect of stenoparib on cell proliferation was assessed in three human cancer cell lines and $IC_{50}$ values were determined. Stenoparib inhibited cell proliferation in an 8-day assay in the BRCA1 mutant human triple negative breast cancer cell line MDA-MB-436 with an $IC_{50}$ value of 0.219 μmol/L. In an 8-day cell proliferation assay in the SR human B cell lymphoma cell line, stenoparib inhibited proliferation with an IC50 value of 1.055 μmol/L. Stenoparib inhibited cell proliferation in a 6-day assay in the human acute myeloid leukemia MV-4-11-luc2/AcGFP cell line with an IC50 value of 1.105 μmol/L.

In an in vitro study, stenoparib inhibited proliferation of the murine lymphocytic leukemia parent cell line P388/S and the P-gp overexpressing P388/VMDRC.04 line to a similar extent, with IC50 values of 2.14 and 1.39 μmol/L, respectively. Addition of the P-gp antagonist verapamil had little effect on inhibition of proliferation by stenoparib in either cell line (IC50 values of 2.34 and 1.82 μmol/L in P388/S and P388/VMDRC.04, respectively). Taken together, these data indicate that P-gp overexpression has no effect on inhibition by stenoparib.

Anti-tumor activity was observed for stenoparib in the BRCA1 mutant MDA-MB-436 human breast cancer subcutaneous xenograft model. Consecutive 28-day administration of Stenoparib at doses of 30 and 100 mg/kg resulted in statistically significant tumor growth inhibition. Stenoparib treatment was well-tolerated at both doses; there was no significant body weight loss.

Stenoparib inhibited PARP activity in tumor tissue from MDA-MB-436 xenografts following a single dose at 30 or 100 mg/kg. PARP activity was assessed in tumor tissue from MDA-MB-436 xenografts following a single dose of Stenoparib at various time points from 1 to 36 hours post-dose. PARP activity was completely inhibited in all tumors at 1 and 6 hours post-dose. At 12 hours, low levels of PARP activity were observed in the 30 mg/kg treated animals but not the 100 mg/kg dosed animals, and at 24 hours PARP activity appeared restored to control levels in both groups of mice.

Administration of stenoparib at 100 mg/kg for 28 days caused statistically significant anticancer activity in the human acute myeloid leukemia (AML) MV-4-11-luc2/AcGFP survival model. Reduced disease burden, as measured by luciferase signal, was observed at 100 mg/kg stenoparib and this translated into a statistically significant survival benefit. No statistically significant reduction in disease burden by luciferase signal or survival benefit was recorded for stenoparib at 10 and 30 mg/kg doses. Stenoparib administration at 10, 30 or 100 mg/kg was well-tolerated without any significant body weight loss.

Stenoparib monotherapy was examined in a finalized Phase 1 study (An Open-Label, Multicenter, Phase ½ Study of Poly (ADP-Ribose) Polymerase (PARP) Inhibitor E7449 as Single Agent in Subjects With Advanced Solid Tumors or With B-cell Malignancies and in Combination With Temozolomide (TMZ) or With Carboplatin and Paclitaxel in Subjects With Advanced Solid Tumors [E7449-E044-101]), and featured a once daily dosing of stenoparib as a single 600 mg dose. None of the 35 subjects assessed had a best overall response (BOR) of CR based on investigator assessment using RECIST 1.1. The overall objective response rate (ORR; CR+PR) was 4.9% (n=2) with 1 subject each in the 600 mg (MTD) and 800 mg dose groups with a BOR of PR. Overall, a BOR of stable disease was observed in 13 subjects (31.7%). Both PR were predicted by DRP® for stenoparib after analyzing biopsies from 13 of the 41 subjects.

Figure 1B:
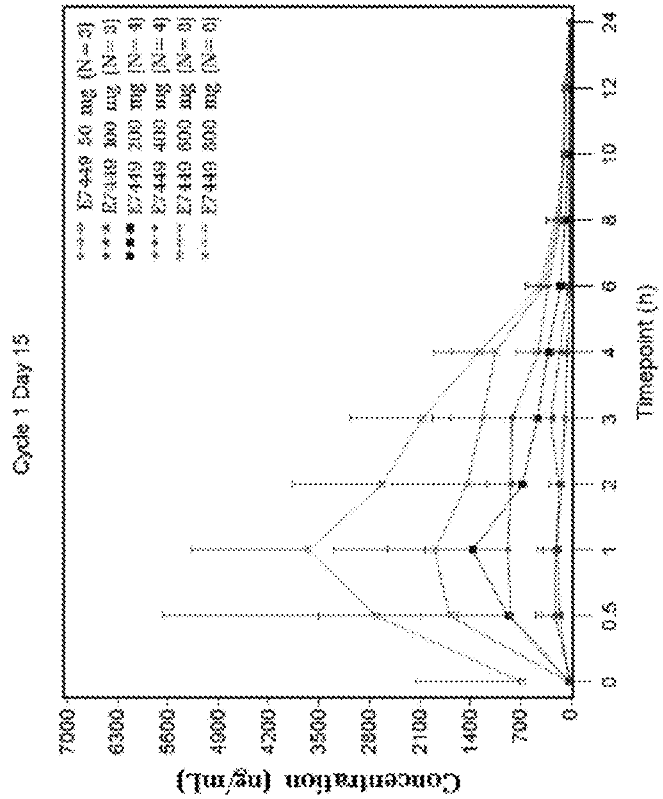
Figure 2A:
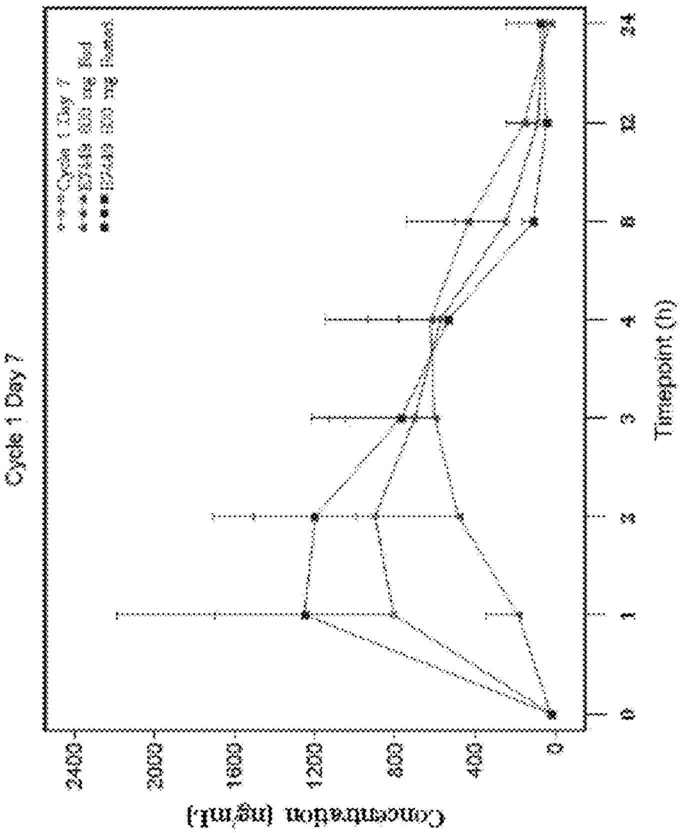
FIG. 2A and FIG. 2B are graphs showing the pharmacokinetics of stenoparib administration after food intake. The different lines represent 600 mg doses of stenoparib (E7449) administered at time 0 with or without food intake. Concentration of stenoparib in blood plasma is shown in ng/ml. Food intake vs fasting comparisons were made after administration of the Cycle 1 Day 7 dose (FIG. 2A) and after the Cycle 1 Day 15 dose (FIG. 2B).
Figure 2B:
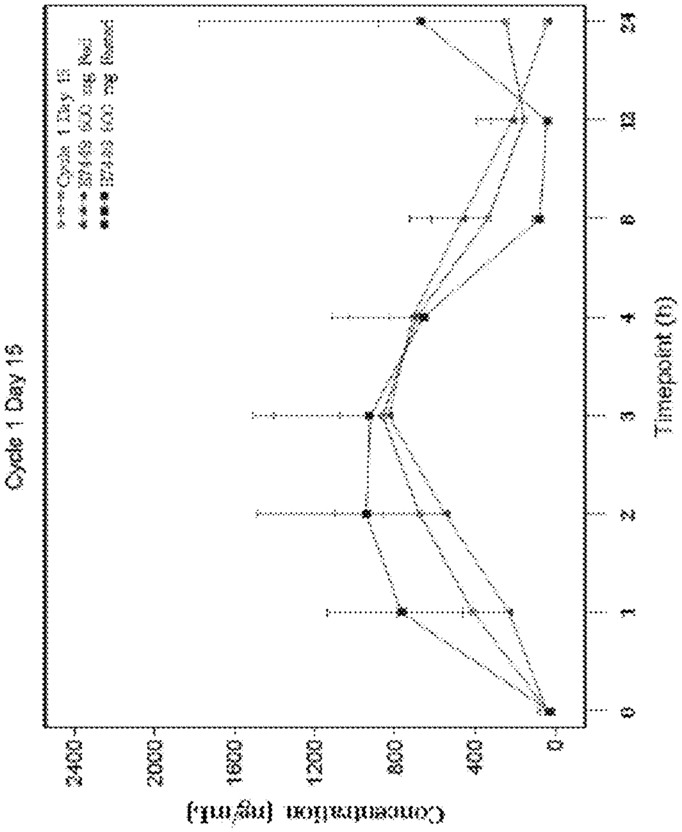

Stenoparib was well absorbed with tmax ranging from 0.5 to 4 hours across subjects and dose groups. The elimination half-life was approximately 8 hours with less than 1.5% of the administered dose recovered in urine. Following single or multiple oral doses between 50 mg and 800 mg a proportional absorption of stenoparib (e.g., in plasma) was found (FIG. 1A and FIG. 1B). At the 600 mg dose, food delayed stenoparib absorption and reduced $C_{max}$ by 60%, and increased AUC by 10% (FIG. 2A and FIG. 2B) in plasma.

Dose dependent inhibition of PARP activity, as demonstrated by percent change in PAR levels, was observed. Maximal inhibition of PARP activity was observed at the MTD dose (600 mg) of single agent stenoparib. Evaluation of PAR levels at the MTD dose of stenoparib (600 mg) in the food effect cohort demonstrated that PAR levels show maximal decrease at 2 to 4 hours post-dose with up to 90% inhibition in PAR levels (from baseline) observed. Sustained PARP inhibition was observed with a 70% or greater decrease in PAR levels observed at 24 hours post-dose. Greater decrease in PAR levels was observed with increasing plasma concentration of stenoparib and with the maximal inhibition observed corresponding to the peak plasma concentration in measurements obtained at Day −2 and Cycle 1 Day 15. A greater decrease in PAR levels was observed with a corresponding higher $C_{max}$ when stenoparib was administered without food than when administered with food.

The present study evaluates the safety and tolerability, antitumor activity, pharmacokinetics, and determine the maximum tolerated dose (MTD) of stenoparib monotherapy (at BID regimen) in subjects with advanced solid tumors.

Dose Selection

In the above-mentioned Phase 1 trial, stenoparib, 600 mg, administered orally once daily, resulted in substantial and sustained PARP inhibition throughout the dosing interval and together with the efficacy observations supported the once daily dosing. However, the relative short half-life around 8 hours speaks to the possibility of increasing the daily dosing by changing from a QD dosing to a BID (i.e., twice per day) dosing.

Stenoparib, 600 mg, administered orally once daily was identified as the MTD in the phase I study, and was suggested as the RP2D for the subsequent phase II part of that study.

A breast cancer study was initiated in June 2018 and discontinued for futility after enrollment of 16 subjects. Twelve subjects were evaluable for response: Nine had PD and three subjects had SD.

The DLT from the phase one study was limited to fatigue and one case of anaphylactic reaction and no significant hematotoxicity or hepatotoxicity was observed though this would have been expected from the preclinical studies.

Safety data from the finalized Phase 1 study together with preliminary data from the Phase 2 study in metastatic breast cancer showed only dose-dependent drug related toxicity for fatigue and phototoxicity (average dose/sqm for each toxicity grade). At doses of 400 mg or higher fatigue was found in 30 subjects (grade 1-2: 25/42 (about 60%) and grade 3: 5/42 (about 12%)), and phototoxicity in 15 subjects (grade 1-2 14/42 (33%) and grade 3: 1/42 (2.6%)). Phototoxicity was in the Danish study primarily seen in 2 subjects treated during the hot summer period in 2018.

However, there does not seem to be dose related hematological and hepatological toxicity, that were the toxicities expected to be dose limiting from the preclinical studies and compared to other PARP inhibitors. Anemia was registered in only few subjects at doses of 400 mg and above 3/42 (7%) (all grade 2) and 4/42 had increased liver enzymes (grade 2: 1/42 (2.6%) and grade 3: 3/42 (7%)).

Gastrointestinal side-effects were registered in some subjects: nausea 14/42 (33%), vomiting 7/42 (16%) and diarrhea 13/42 (25%) all grade 1-2 apart from two cases of grade 3 diarrhea.

The efficacy was lower than expected with the only 2 subjects obtaining partial remission had received 600 and 800 mg respectively and furthermore had a relatively low body weight (61.4 and 63.7 kg). Thus, there is a risk that the recommended once daily dosing decided from the DLT in the phase 1 study may be too low. As discussed above, the half-life of stenoparib was discovered to be about 8 hours, so the initial dosing in the present study is a 200 mg am (morning) and 400 mg pm (evening), with a stepwise dose expansion of 200 mg daily to determine MTD using a 3+3 design.

Objectives

The primary objective of this study is to determine the maximum tolerated dose (MTD) of stenoparib monotherapy given twice daily (BID) in subjects with advanced solid tumors.

The secondary objectives of this study are to evaluate the anti-tumor activity of stenoparib monotherapy, evaluate the pharmacokinetics (PK) of stenoparib monotherapy, and evaluate the safety and tolerability of stenoparib monotherapy.

Study Outcome Measures

The MTD (e.g., of stenoparib) is defined as 1 dose level below the dose in which dose limiting toxicities (DLTs) are observed in ≥33% of the participants during the first 14 days of the main treatment period.

The secondary anti-tumor activity outcome measures in this study are:

- To evaluate the objective response rate (ORR) of stenoparib monotherapy.
  - ORR is defined as the proportion of subjects who achieve a Complete Response (CR) or Partial Response (PR) as assessed by RECIST v1.1.
- To evaluate the duration of overall response (DOR) of stenoparib monotherapy.
  - DOR is defined as the time in months from the first documented CR or PR per RECIST v. 1.1 to disease recurrence or disease progression (PD) whichever occurs first.
- To evaluate progression free survival (PFS) of stenoparib monotherapy.
  - PFS is defined as the time from study treatment initiation to either first observation of progressive disease or occurrence of death.
- To evaluate overall survival (OS) of stenoparib monotherapy.
  - OS is defined as the time from study treatment initiation to death from any cause or last day known to be alive.

Determining MTD of Stenoparib

The determination of the maximum tolerated dose of stenoparib follows an accelerated titration method followed by a standard "3+3" design. The MTD is defined as one dose level (cohort) below the dose in which dose limiting toxicities (DLTs) were observed in ≥33% of the participants.

The calculation of the sample size for this trial is based on the traditional 3+3 dose escalation scheme which is conducted as follows:

- Subjects are treated in cohorts of one (Cohort 1) or three (Cohorts 2-3) subjects, each receiving the same dose. For the assessment of a DLT, subjects are observed for 14 days.
- In Cohort 1, if the one subject does not exhibit a DLT, the next cohort of three subjects will receive the next higher dose (Cohort 2). In Cohort 2, if none of the three subjects exhibits a DLT, the next cohort of three subjects will receive the next higher dose (Cohort 3).
- Otherwise, if at least one subject of a cohort exhibits a DLT, a further cohort of three subjects is treated at the same dose level (cohort) without escalating the dose.
- If exactly one out of the six subjects treated at this dose exhibits a DLT, the trial continues as planned at the next higher dose level (cohort).
- If two or more subjects out of the six subjects treated at this dose exhibit a DLT, the dose escalation stops at that level and the next lower dose is considered as the MTD. When the escalation has stopped, additional subjects will be treated at the MTD to a total of six subjects.

Cohort escalation (e.g., the decision to progress from one cohort (dose level) to another) does not proceed until all of the following events have occurred:

(1) All study subjects in a given cohort (dose level) have been enrolled, and (2) All such subjects have been followed for at least 14 days from the initiation of study treatment, and (3) None of the DLTs outlined below have occurred, and further dose escalation is recommended

- Hematological
  - Grade 4 neutropenia [or Grade 3 neutropenia with fever (>38.5 °C in axilla)] for ≥7 days
  - Grade 4 thrombocytopenia (Grade 3 thrombocytopenia with bleeding) lasting >7 days.
- Other non-hematological toxicity
  - Grade 3 fatigue, or a 2-point decline in Eastern Cooperative Oncology Group (ECOG) performance status that persists for >7 days.
  - Nausea, vomiting or diarrhea that persists at Grade 3 or 4 despite maximal medical therapy.
  - Any Grade 3 or higher non-hematological laboratory abnormalities that require hospitalization.

Figure 3:
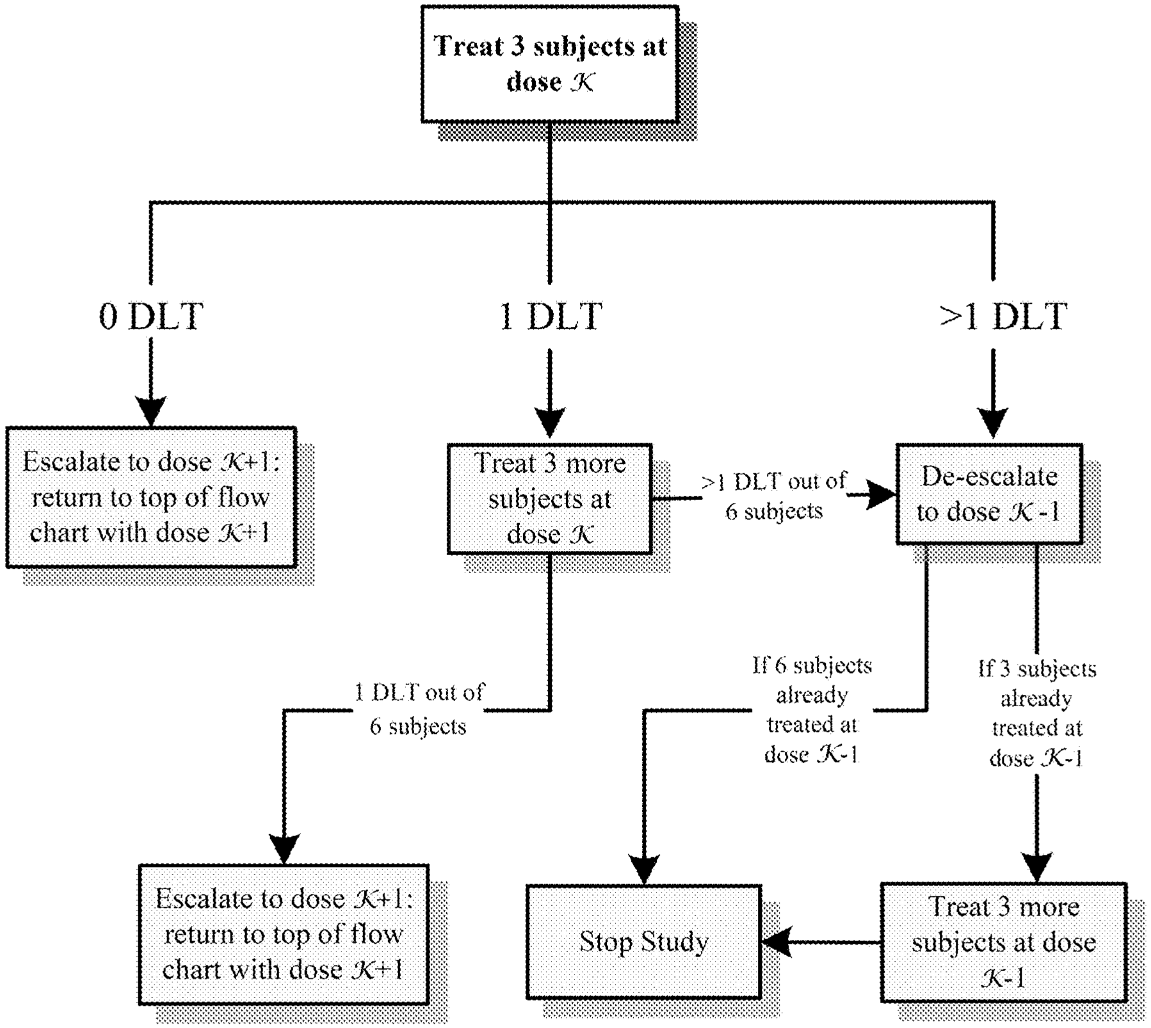
FIG. 3 is a diagram showing a 3+3 dose escalation study design for determining the maximum tolerated dose (MTD), e.g., of stenoparib or of dovitinib.

The MTD determination study design is illustrated in FIG. 3.

Inclusion Criteria

Subjects are eligible for enrollment in the study if they meet the following criteria at time of Screening:

1. Age 18 years or older.
2. Histologically or cytological documented solid tumor.
3. Available tumor biopsy (most recent) for DRP® analysis.
4. Measurable disease by computed tomography (CT) scan or magnetic resonance imaging (MRI) if possible.
5. Performance status of Eastern Cooperative Oncology Group (ECOG)≤1.
6. Recovered to Grade <1 or baseline from prior surgery or from acute toxicity prior radiotherapy, or from treatment with cytotoxic, hormonal or biologic agents.
7. ≥2 weeks must have elapsed since any prior surgery or therapy with granulocyte colony-stimulating factor (G-CSF) and granulocyte-macrophage colony-stimulating factor (GM-CSF).

8. Subjects with intracranial disease must be on stable or decreased level of steroid therapy (e.g. dexamethasone) for at least 7 days prior to baseline MRI. Non-enzymatic inducing anti-epileptic drugs are allowed.
9. Adequate conditions as evidenced by the following clinical laboratory values:
   a. Absolute neutrophils count (ANC) ≥1500/mm3 ($1.5\times10^3$/mL)
   b. Hemoglobin >10.0 g/dL
   c. Platelets ≥100,000/mm3 (≥$100\times10^9$/L)
   d. Alanine aminotransferase (ALT) and aspartate aminotransferase (AST)≤3×ULN or ≤5×ULN in presence of liver metastases
   e. Serum bilirubin≤1.5 ULN
   f. Alkaline phosphatase≤2.5×ULN
   g. Creatinine≤1.5 ULN
   h. Blood urea nitrogen (BUN)≤2×ULN.
10. Life expectancy equal or longer than 3 months.
11. The subject is willing to provide written informed consent to participate in the study after reading the informed consent form and the information provided and has had the opportunity to discuss the study with the investigator or designee.
12. The subject is able to communicate satisfactorily with the investigator and to participate in, and comply with, the requirements of the study.
13. The subject is able to understand the nature of the study and any potential hazards associated with participating in it.
14. Negative pregnancy test for female subjects of childbearing potential. Women of childbearing potential (WOCBP) and Women of non-childbearing potential are eligible to participate. Both women of childbearing potential and women of non-childbearing potential should use an approved method of birth control and agree to continue to use this method for the duration of the study (and for 90 days after taking the last dose of study drug). All male subjects/partners must agree to consistently and correctly use a condom for the duration of the study and for 90 days after taking the study drug. In addition, subjects may not donate sperm for the duration of the study and for 90 days after taking study drug.

Exclusion Criteria

Subjects meeting any of the following criteria at time of Screening are excluded from enrollment in the clinical study:

1. Concurrent chemotherapy, radiotherapy, hormonal therapy, or other investigational drug except non-disease related conditions (e.g., insulin for diabetes) during study period.
2. Other malignancy with exception of curative treated non-melanoma skin cancer or cervical carcinoma in situ within 5 years prior to entering the study.
3. Any active infection requiring parenteral or oral antibiotic treatment.
4. Known HIV positivity.
5. Known active hepatitis B or C.
6. Clinically significant (i.e., active) cardiovascular disease:
   a. Stroke within ≤6 months prior to day 1
   b. Transient ischemic attack (TIA) within $6 months prior to day 1
   c. Myocardial infarction within ≤6 months prior to day 1
   d. Unstable angina
   e. New York Heart Association (NYHA) Class II or greater congestive heart failure (CHF)
   f. Serious cardiac arrhythmia requiring medication.
7. Other medications or conditions, including surgery, that in the Investigator's opinion would contraindicate study participation for safety reasons or interfere with the interpretation of study results.
8. Inability to take oral medication, or malabsorption syndrome or any other uncontrolled gastrointestinal condition (e.g., nausea, diarrhea, or vomiting) that might impair the bioavailability of stenoparib and dovitinib.
9. Requiring immediate palliative treatment of any kind including surgery and/or radiotherapy.
10. Female subjects who are pregnant or breast-feeding (pregnancy test with a positive result before study entry).

Study Treatment

The dose levels for stenoparib monotherapy BID dosing that are tested in this study are shown below in Table 5:

TABLE 5

Dosing for Stenoparib MTD Determination for Stenoparib Monotherapy

| Dose Cohorts Dose Cohort | Stenoparib Monotherapy Dose (BID) |
|---|---|
| Cohort 1 | 600 mg (morning dose: 200 mg + evening dose: 400 mg) |
| Cohort 2 | 800 mg (morning dose: 400 mg + evening dose: 400 mg) |
| Cohort 3 | 1000 mg (morning dose: 400 mg + evening dose: 600 mg) |

On Day 1 of first treatment cycle (C1D1), subjects are administered stenoparib monotherapy as oral capsules taken twice daily. Each treatment cycle consists of 28 days.

Blood samples are collected for Stenoparib PK analysis at the following time points:

C1D1: prior to drug administration (morning dose), 1 h (±15 min), 3 h (±15 min), 4 h (±15 min), 6 h (±15 min), 12 h (±1 h, the sample should be taken before the evening dose)

C1D2: prior to drug administration (morning dose)

C1D7: prior to drug administration (morning dose)

C1D15: prior to drug administration (morning dose).

CXD1: prior to drug administration (morning dose) for the first day of all subsequent treatment cycles Once the MTD has been determined, subjects enrolled in lower dose cohorts are allowed to escalate the dose to the MTD, if acceptable per the Investigator's discretion. Subjects are eligible for continuing treatment in absence of progressive disease or unacceptable toxicity or withdrawal of consent.

Treatment Phase

Each treatment cycle is 28 days. Treatment consists of one or more treatment cycles, i.e., dosing cycles. A subject is considered to have completed the treatment phase once they complete the end of treatment (EOT) visit conducted 30 (+7) days after the last treatment visit.

A twice daily dose of stenoparib will be administered as hard gelatin capsules, independent of food intake in a 28-day cycle. The capsules are to be administered twice a day about the same time each treatment day.

Dose Modification for Stenoparib

The dose level of stenoparib can be modified based on observed toxicity. Details of dose modification are summarized below in Table 6:

TABLE 6

| Stenoparib Dose Modification | | |
|---|---|---|
| Stenoparib-Related Toxicity[a] | During Therapy | Approximate dose Adjustment[b] |
| Grade 1 | | |
| All occurrences | Continue treatment | Maintain dose level |
| Grade 2 | | |
| $1^{st}$ occurrence | Interrupt b until resolved to Grade 0-1 or baseline | Maintain dose level |
| $2^{nd}$ occurrence (same toxicity or new toxicity) | | $1^{st}$ dose reduction of stenoparib with 200 mg primarily, of the morning dose, secondarily, the evening dose |
| $3^{rd}$ occurrence (same toxicity or new toxicity) | | $2^{nd}$ dose reduction of stenoparib with another 200 mg primarily, of the morning dose, secondarily, the evening dose |
| $4^{th}$ occurrence (same toxicity or new toxicity) | | Discuss with sponsor |
| Grade 3 | | |
| $1^{st}$ occurrence | Interrupt[b] until resolved to Grade 0-1 or baseline | $1^{st}$ dose reduction of stenoparib to with 200 mg primarily, of the morning dose, secondarily, the evening dose |
| $2^{nd}$ occurrence (same toxicity or new toxicity) | | 2nd dose reduction of stenoparib with another 200 mg primarily, of the morning dose, secondarily, the evening dose |
| $3^{rd}$ occurrence (same toxicity or new toxicity) | Discontinue treatment | Not Applicable |
| Grade 4[c] | | |
| 1st occurrence | Interrupt until resolved to Grade 0-1 or baseline | $1^{st}$ dose reduction of stenoparib with 400 mg primarily, of the morning dose, secondarily, the evening dose |
| 2nd occurrence (same toxicity or new toxicity) | Discontinue treatment | Discuss with sponsor |

For grading see Common Toxicity Criteria for Adverse Events (CTCAE v5.0; cancer.gov, Nov. 27, 2017) [a]: Excluding alopecia and nausea, vomiting and diarrhea not receiving adequate treatment. [b]: A delay of stenoparib for more than 21 days due to any toxicity will require a discussion with the sponsor before treatment can be resumed. [c]: Excluding laboratory abnormalities judged to be non-life-threatening, in which case manage as Grade 3.

Example 2. Treatment of Cancer with BID Dosing Stenoparib and QD Dosing Dovitinib This study evaluates safety and tolerability, antitumor activity, and pharmacokinetics of stenoparib (MTD) and dovitinib as combination therapy and determines the MTD of dovitinib when given in combination with the MTD of stenoparib determined in Example 1.

Objectives

The primary objective of this study is to determine the MTD of dovitinib given in combination with stenoparib (MTD) in subjects with advanced solid tumors.

The secondary objectives of this study are to evaluate the anti-tumor activity of stenoparib in combination with dovitinib, evaluate the pharmacokinetics (PK) of stenoparib in combination with dovitinib, and evaluate the safety and tolerability of stenoparib in combination with dovitinib.

Study Outcome Measures

The MTD (e.g., of stenoparib) is defined as 1 dose level below the dose in which dose limiting toxicities (DLTs) are observed in ≥33% of the participants during the first 14 days of the main treatment period.

The secondary anti-tumor activity outcome measures in this study are:

- To evaluate the objective response rate (ORR) of stenoparib in combination with dovitinib.
  - ORR is defined as the proportion of subjects who achieve a Complete Response (CR) or Partial Response (PR) as assessed by RECIST v1.1.
- To evaluate the duration of overall response (DOR) of stenoparib in combination with dovitinib.
  - DOR is defined as the time in months from the first documented CR or PR per RECIST v. 1.1 to disease recurrence or disease progression (PD) whichever occurs first.
- To evaluate progression free survival (PFS) of stenoparib in combination with dovitinib.
  - PFS is defined as the time from study treatment initiation to either first observation of progressive disease or occurrence of death.
- To evaluate overall survival (OS) of stenoparib in combination with dovitinib.
  - OS is defined as the time from study treatment initiation to death from any cause or last day known to be alive.

Determining MTD of Dovitinib

The determination of the maximum tolerated dose of dovitinib follows the accelerated titration method followed by a standard "3+3" design described in Example 1 for stenoparib. The MTD is defined as one dose level (cohort) below the dose in which dose limiting toxicities (DLTs) were observed in ≥33% of the participants.

Inclusion and Exclusion Criteria

This study shares the same Inclusion and Exclusion Criteria as described above in Example 1.

Study Treatment

The dose levels for dovitinib dosing for combination treatment with stenoparib that are tested in this study are shown below in Table 7:

TABLE 7

| Dosing for Dovitinib MTD Determination for Stenoparib and Dovitinib Combination Therapy | |
|---|---|
| Dose Cohorts Dose Cohort | Combination Stenoparib and Dovitinib Dosing |
| Cohort 1 | Stenoparib (MTD) + 300 mg dovitinib |
| Cohort 2 | Stenoparib (MTD) + 400 mg dovitinib |
| Cohort 3 | Stenoparib (MTD) + 500 mg dovitinib |

Dovitinib will be administered once daily (morning) on a 5 days on and 2 days off schedule. In a 28 day cycle, dovitinib will be administered Cycle (C) 1 Day (D) 1 (C1D1)-C1D5, C1D8-C1D12, C1D15-C1D19, and C1D22-C1D26.

Dovitinib (TKI258), a pan-TKI, is an inhibitor of type III-V receptor tyrosine kinases (RTKs) that mediate both endothelial and tumor cell proliferation and survival. Dovitinib is formulated as a film-coated tablet of 100 mg strength.

Blood samples will be collected for stenoparib and dovitinib PK analysis at the following time points (in relation to stenoparib dosing):

C1D1: prior to drug administration (morning dose), 0.5 h (±15 min), 1 h (±15 min), 2 h (±15 min), 3 h (±15 min), 4 h (±15 min), 6 h (±15 min), 8 h (±15 min), 10 h (±1 h), 12 h (±1 h, to be taken before the evening dose)

C1D2: prior to drug administration (morning dose)

C1D7: prior to drug administration (morning dose)

C1D15: prior to drug administration (morning dose), 0.5 h (+15 min), 1 h (+15 min), 2 h (+15 min), 3 h (+15 min), 4 h (+15 min), 6 h (+15 min), 8 h (+15 min), 10 h (+1 h), 12 h (+1 h, to be taken before the evening dose)

CXD1: prior to drug administration (morning dose) for the first day of all subsequent treatment cycles Once the MTD has been determined, subjects enrolled in lower dose cohorts will be allowed to escalate the dose to the MTD, if acceptable per the Investigator's discretion. Subjects will be eligible for continuing treatment in absence of progressive disease or unacceptable toxicity or withdrawal of consent.

Treatment Phase

Each treatment cycle is 28 days. Treatment consists of one or more treatment cycles, i.e., dosing cycles. A subject is considered to have completed the treatment phase once they complete the EOT visit conducted 30 (+7) days after the last treatment visit.

A twice daily dose of stenoparib will be administered as hard gelatin capsules, independent of food intake in a 28 days cycle. Dovitinib tablets are supplied as 100 mg film-coated tablets in a blister pack. The capsules are to be administered twice a day about the same time each treatment day. The morning dose of stenoparib is administered at the same time as dovitinib.

Dovitinib will be administered once daily (morning) on a 5 days on and 2 days off schedule independent of food intake at the same time as the stenoparib morning dose. In a 28 day cycle, dovitinib will be administered C1D1-C1D5, C1D8-C1D12, C1D15-C1D19, and C1D22-C1D26.

Dose Modification

Dose modification for dovitinib treatment may be allowable according to Table 8 below.

TABLE 8

| Dose modification rules for dovitinib | |
|---|---|
| Dovitinib-Related Toxicity intensity[a] | Dose modification[b, c] |
| Cardiovascular | |
| Hypertension | Treatment-emergent hypertension should be treated as per standard practice. |
| Systolic blood pressure (SBP) <160 mmHg and/or diastolic blood pressure (DBP) <100 mm Hg, with or without anti-hypertensive medication | Maintain dose level |
| ≥160 mmHg and/or DBP ≥100 mm Hg, with or without anti- hypertensive medication, but not immediately life-threatening | Delay the dovitinib treatment and initiate/intensify antihypertensive therapy. Dovitinib may be restarted in conjunction with standard anti- hypertensive medication if BP is controlled (i.e., BP <160/100 mmHg). Once BP is controlled after suspending dovitinib, maintain dose level or reduce one dose level at the discretion of the healthcare provider. |
| Life-threatening consequences (e.g., malignant hypertension, transient or permanent neurologic deficit, hypertensive crisis); urgent intervention indicated | Discontinue dovitinib treatment permanently. |
| Left Ventricular Systolic Dysfunction | |
| Left ventricular ejection fraction (LVEF) ≥50%/lower limit of normal (LLN) (echocardiogram (ECHO)), or ≥45%/LLN (multigated acquisition (MUGA) scan) | Maintain dose level |
| LVEF <50%/LLN (ECHO), or <45%/LLN (MUGA), or Symptomatic due to drop in ejection fraction responsive to intervention | Delay dovitinib treatment until resolved to ≥50%/LLN (ECHO) or ≥45%/LLN (MUGA), then reduce one dose level. |

TABLE 8-continued

| Dose modification rules for dovitinib | |
|---|---|
| Dovitinib-Related Toxicity intensity[a] | Dose modification[b, c] |
| Refractory or poorly controlled heart failure due to drop in ejection fraction; intervention such as ventricular assist device, intravenous vasopressor support or heart transplant indicated | Discontinue dovitinib treatment. |
| **Other Cardiovascular** | |
| Grade 1 | Maintain dose level |
| Grade 2 | Maintain dose level<br>If asymptomatic decrease of LVEF by absolute value of 20% and to < LLN, delay dovitinib treatment until resolved to ≤ grade 1, then reduce one dose level. |
| Grade 3 | Delay dovitinib treatment until resolved to ≤ grade 1, then reduce one dose level. |
| Grade 4 | Discontinue study treatment |
| **Gastrointestinal** | |
| Diarrhea | At the first sign of abdominal cramping, loose stools, or onset of diarrhea, it is recommended that the subject be treated according to institutional standard of care. |
| Grade 1 (despite maximal anti- diarrheal medication) | Maintain dovitinib dose level |
| Grade 2 (despite maximal anti- diarrheal medication) | Delay dovitinib treatment, until resolved to ≤ grade 1, then re- start at the current dose level.<br>If diarrhea returns as ≥ grade 2, then suspend dose until resolved to ≤ grade 1, then reduce one dose level. |
| Grade 3/4 (despite maximal anti- diarrheal medication) | Delay dovitinib treatment until resolved to ≤ grade 1, then reduce one dose level. |
| Nausea | Suspend dose for CTCAE grade 2-3 nausea only if it could not be controlled despite the use of standard anti-emetics. |
| Grade 1 (despite standard anti- emetics) | Maintain dovitinib dose level |
| Grade 2 (despite standard anti- emetics) | Delay dovitinib treatment, until resolved to ≤ grade 1, and then re-start at the current dose level.<br>If nausea returns as > grade 2, then suspend dose until resolved to ≤ grade 1, then reduce one dose level. |
| Grade 3 (despite standard anti- emetics) | Delay dovitinib treatment until resolved to ≤ grade 1, then reduce one dose level. |
| Vomiting | Suspend dose for CTCAE grade 2-4 vomiting only if it cannot be controlled despite the use of standard anti-emetics. |
| Grade 1 (despite standard anti- emetics) | Maintain dovitinib dose level |
| Grade 2 (despite standard anti- emetics) | Delay dovitinib treatment, until resolved to ≤ grade 1, and then re-start at the current dose level.<br>If nausea returns as > grade 2, then suspend dose until resolved to ≤ grade 1, then reduce one dose level. |
| Grade 3/4 (despite standard anti- emetics) | Delay study treatment until resolved to ≤ grade 1, then reduce 1 dose level. |
| **Hematologic** | |
| Febrile neutropenia (Grade 3 or 4) (Per protocol) fever of unknown origin without clinically or microbiologically documented infection (absolute neutrophil count (ANC) 1.0 × $10^9$/L, fever ≥38.5° C.) | Delay dovitinib treatment until resolved, then reduce one dose level. |
| ≥Grade 3 anemia judged to be a hemolytic process secondary to study treatment | Discontinue dovitinib treatment. |
| ≥Grade 3 lymphopenia considered clinically significant | Requires dovitinib dose interruption until resolved to ≤ grade 1, then reduce dose level. |
| **Neutropenia/Neutrophil Count Decreased** | |
| Grade 1 or 2 | Maintain dovitinib dose level. |
| Grade 3 | Delay dovitinib treatment until resolved to ≤ grade 2, then: |
| Grade 4 | If resolved by ≤7 days after suspending dovitinib, maintain dose level.<br>If resolved by >7 days after suspending dovitinib, reduce one dose level. |

TABLE 8-continued

| Dose modification rules for dovitinib | |
|---|---|
| Dovitinib-Related Toxicity intensity[a] | Dose modification[b, c] |
| **Thrombocytopenia/Platelet Count Decreased** | |
| Grade 1 or 2 | Maintain dovitinib dose level. |
| Grade 3 | Delay dovitinib treatment until resolved to ≤ grade 1, then:<br>If resolved by ≤7 days after suspending dovitinib, maintain dose level.<br>If resolved by >7 days after suspending dovitinib, reduce one dose level. |
| Grade 4 | Delay dovitinib treatment until resolved to ≤ grade 1, then reduce one dose level. |
| **Hepatic** | |
| ≥grade 3 alkaline phosphatase or GGT | Isolated values of ≥ grade 3 alkaline phosphatase or GGT values will NOT require dose interruption. |
| **Alanine Aminotransferase (ALT) or Aspartate Transaminase (AST)** | |
| ≤3.0 × upper limit of normal (ULN) | Maintain dovitinib dose level with liver function tests (LFTs)[e] monitored as per protocol. |
| >3.0 to ≤5.0 × ULN, without bilirubin elevation to >2.0 × ULN | Maintain dovitinib dose level with weekly monitoring of LFTs[e], or more frequently if clinically indicated, until resolved to ≤ grade 1 or baseline. |
| >5.0 × ULN | Delay dovitinib treatment until resolved to ≤ grade 1 or baseline, then reduce one dose level.<br>Monitor LFTs[e] weekly, or more frequently if clinically indicated, for 8 weeks; then, every 2 weeks for 4 weeks; then, every 4 weeks as per protocol.<br>Following re-introduction of dovitinib, if ALT or AST elevations >3 × ULN recur as assessed on 2 separate measurements no more than 1 week apart, then study treatment should be permanently discontinued.<br>If study treatment is permanently discontinued, then subjects should be monitored weekly (including LFTs[e]), or more frequently if clinically indicated, until AST or ALT have resolved to ≤ grade 1 or stabilization (i.e., no CTCAE grade change over 4 weeks). |
| **Total Bilirubin** | |
| ≤1.5 × ULN | Maintain dovitinib dose level with LFTs[e] monitored as per protocol. |
| >1.5 to 3.0 × ULN with ALT or AST ≤3.0 × ULN | Maintain dovitinib dose level with LFTs[e] monitored as per protocol. |
| >3.0 × ULN | Discontinue dovitinib treatment permanently.<br>Subjects should be monitored weekly (including LFTs[e]), or more frequently if clinically indicated, until total bilirubin has resolved to ≤ grade 1 or stabilization (i.e., no CTCAE grade change over 4 weeks).<br>Note: If grade 3 or grade 4 hyperbilirubinemia is due to the indirect component only, and hemolysis as the etiology has been ruled out as per institutional guidelines (e.g., review of peripheral blood smear and haptoglobin determination), then reduce one dose level and continue dovitinib treatment at the discretion of the healthcare provider. |
| **ALT or AST, and Concurrent Bilirubin** | |
| ALT or AST >3.0 × ULN and Total Bilirubin >2.0 × ULN | Discontinue dovitinib treatment permanently.<br>Subjects should be monitored weekly (including LFTs[e]), or more frequently if clinically indicated, until ALT/AST and total bilirubin have resolved to ≤ grade 1 or stabilization (i.e., no CTCAE grade change over 4 weeks). |
| **Renal Serum Creatinine** | |
| Grade 1 or 2 | Maintain dose level |
| Grade 3 | Delay dovitinib treatment until resolved to ≤ grade 1 or baseline, then reduce one dose level |
| Grade 4 | Discontinue dovitinib treatment |

TABLE 8-continued

| Dose modification rules for dovitinib | |
|---|---|
| Dovitinib-Related Toxicity intensity[a] | Dose modification[b, c] |
| Amylase and/or Lipase Elevations | |
| Asymptomatic Grade 1 or 2 | Maintain dovitinib dose level |
| Asymptomatic Grade 3 or 4 | Subjects who develop grade 3 or 4 hyperlipasemia or hyperamylasemia without clinical or other evidence of pancreatitis may continue study medication without interruption. |
| Pancreatitis | |
| Grade 2 | Maintain dovitinib dose level |
| Grade 3 or 4 | Discontinue dovitinib treatment |
| Hand-Foot Syndrome | |
| Grade 1 or 2 | Maintain dovitinib dose level |
| Grade 3 | Delay dovitinib treatment until resolved to ≤ grade 1 then reduce 1 dose level. |
| Grade 4 | Discontinue dovitinib treatment |
| Other Clinically Significant Adverse Events | |
| Grade 1 or 2 | Maintain dovitinib dose level |
| Grade 3 (except hyperlipidemia[d]) | Delay dovitinib treatment until resolved to ≤ grade 1 or baseline, then maintain dose level or reduce one dose level at the discretion of the healthcare provider. |
| Grade 4 | Delay treatment until resolved to ≤ grade 1 or baseline, then reduce one dose level or discontinue dovitinib at the discretion of the healthcare provider. |

All dose modifications should be based on the worst preceding toxicity.

[a]Common Terminology Criteria for Adverse Events (CTCAE) v4.03 (cancer.gov; Jun. 14, 2010)

[b]Subjects are allowed two dose reductions: a dose reduction to 400 mg from 500 mg, and, if necessary, a dose reduction to 300 mg from 400 mg.

[c]If a subject requires a dose interruption of >21 days starting from the first day a dose was missed, then the subject must be discontinued from the study. Subjects who discontinue the study for a study related adverse event including an abnormal laboratory value must be followed at least once a week for 30 days and subsequently at 30 days intervals until resolution or stabilization of the event, whichever comes first.

[d]Grade 3 hyperlipidemia (hypercholesterolemia and/or hypertriglyceridemia) should be managed using standard therapies. Fluvastatin and Rosuvastatin may have potential of drug to drug interactions. If these statins are prescribed, close clinical monitoring including serum lipids is required since dovitinib could reduce the exposure of statins. Statins should be prescribed according to product label/data sheets for HMG-CoA reductase inhibitors. Treatment of hyperlipidemia should take into account the pre-treatment status and dietary habits. Blood tests to monitor hyperlipidemia must be taken in the fasting state. Grade 2 or higher hypercholesterolemia (>300 mg/dL or 7.75 mmol/L) or Grade 2 or higher hypertriglyceridemia (>2.5 × ULN) should be treated with fibrate, or appropriate lipid-lowering medication in addition to diet.

[e]LFTs include albumin, ALT, AST, total bilirubin (fractionated [direct and indirect], if total bilirubin: 2.0 × ULN), alkaline phosphatase (fractionated [quantification of isoenzymes], if alkaline phosphatase ≥ Grade 2), and γ-glutamyl transferase (GGT).

Example 3. Administration of Stenoparib BID to a Subject to Treat a Cancer

According to the methods disclosed herein, a subject, such as a human subject, with a solid tumor cancer (e.g., ovarian cancer) can be treated with a composition containing stenoparib or a pharmaceutically acceptable salt thereof or a hydrate thereof. The subject may be determined to be responsive to stenoparib or a pharmaceutically acceptable salt thereof or a hydrate thereof prior to treatment by using the Stenoparib DRP® described herein.

The subject may be administered stenoparib or a pharmaceutically acceptable salt thereof or a hydrate thereof orally twice a day, e.g., as a first dose and a second dose, according to a dosing regimen. The dosing regimen may include 2 to 8 dosing cycles. Each dosing cycle may be 28 days in length.

The subject may be administered a first dose of about 200 mg of stenoparib or a pharmaceutically acceptable salt thereof or a hydrate thereof (e.g., as one 200 mg hard gel capsule) and a second dose of about 400 mg of stenoparib or a pharmaceutically acceptable salt thereof or a hydrate thereof (e.g., as two 200 mg hard gel capsules) during each day of the dosing regimen; a first dose of about 400 mg of stenoparib or a pharmaceutically acceptable salt thereof or a hydrate thereof (e.g., as two 200 mg hard gel capsules) and a second dose of about 400 mg of stenoparib or a pharmaceutically acceptable salt thereof or a hydrate thereof (e.g., as two 200 mg hard gel capsules) during each day of the dosing regimen; or a first dose of about 400 mg of stenoparib or a pharmaceutically acceptable salt thereof or a hydrate thereof (e.g., as two 200 mg hard gel capsules) and a second dose of about 600 mg of stenoparib or a pharmaceutically acceptable salt thereof or a hydrate thereof (e.g., as three 200 mg hard gel capsules) during each day of the dosing regimen. The subject may be administered the second dose about 12 hours after administration of the first dose during each day of the dosing regimen. The subject may be administered the first dose and the second dose of stenoparib or the pharmaceutically acceptable salt thereof or the hydrate thereof at about the same time during each day of the dosing regimen.

Example 4. Administration of Stenoparib BID and Dovitinib QD to a Subject to Treat a Cancer According to the methods disclosed herein, a subject, such as a human subject, with a solid tumor cancer (e.g., prostate or ovarian cancer) can be treated with a first composition containing stenoparib or a pharmaceutically acceptable salt thereof or a hydrate thereof and a second composition containing dovitinib or a pharmaceutically acceptable salt thereof or a hydrate thereof. The subject may be determined to be responsive to stenoparib or a pharmaceutically acceptable salt thereof or a hydrate thereof and/or dovitinib or a pharmaceutically acceptable salt thereof or a hydrate thereof prior to treatment by using the Stenoparib DRPR and/or the Dovitinib DRP® described herein.

The subject may be administered stenoparib or a pharmaceutically acceptable salt thereof or a hydrate thereof orally twice a day, e.g., as a first dose and a second dose, and dovitinib or a pharmaceutically acceptable salt thereof or a hydrate thereof orally once a day, e.g., as a single dose, according to a dosing regimen. The subject may be administered dovitinib on a 5 days on and 2 days off schedule. The dosing regimen may include 2 to 8 dosing cycles. Each dosing cycle may be 28 days in length. For example, during a 28-day dosing cycle, the subject may be administered dovitinib or the pharmaceutically acceptable salt thereof or the hydrate thereof on Days 1-5, 8-12, 15-19, and 22-26, and not on Days 6, 7, 13, 14, 20, and 21.

The subject may be administered a first dose of about 200 mg of stenoparib or a pharmaceutically acceptable salt thereof or a hydrate thereof (e.g., as one 200 mg hard gel capsule) and a second dose of about 400 mg of stenoparib or a pharmaceutically acceptable salt thereof or a hydrate thereof (e.g., as two 200 mg hard gel capsules) during each day of the dosing regimen; a first dose of about 400 mg of stenoparib or a pharmaceutically acceptable salt thereof or a hydrate thereof (e.g., as two 200 mg hard gel capsules) and a second dose of about 400 mg of stenoparib or a pharmaceutically acceptable salt thereof or a hydrate thereof (e.g., as two 200 mg hard gel capsules) during each day of the dosing regimen; or a first dose of about 400 mg of stenoparib or a pharmaceutically acceptable salt thereof or a hydrate thereof (e.g., as two 200 mg hard gel capsules) and a second dose of about 600 mg of stenoparib or a pharmaceutically acceptable salt thereof or a hydrate thereof (e.g., as three 200 mg hard gel capsules) during each day of the dosing regimen. The subject may be administered the second dose about 12 hours after administration of the first dose during each day of the dosing regimen. The subject may be administered the first dose and the second dose of stenoparib or the pharmaceutically acceptable salt thereof or the hydrate thereof at about the same time during each day of the dosing regimen.

In addition, the subject may be administered a single dose of about 300 mg of dovitinib or a pharmaceutically acceptable salt thereof or a hydrate thereof (e.g., as three 100 mg film-coated tablets) during each day of the dosing regimen; a single dose of about 400 mg of dovitinib or a pharmaceutically acceptable salt thereof or a hydrate thereof (e.g., as four 100 mg film-coated tablets) during each day of the dosing regimen; or a single dose of about 500 mg of dovitinib or a pharmaceutically acceptable salt thereof or a hydrate thereof (e.g., as five 100 mg film-coated tablets) during each day of the dosing regimen. The subject may be administered the single dose of dovitinib or the pharmaceutically acceptable salt thereof or the hydrate thereof prior to administering the first dose of stenoparib or the pharmaceutically acceptable salt thereof or the hydrate thereof during each day of the dosing regimen that includes administration of dovitinib or the pharmaceutically acceptable salt thereof or the hydrate thereof.

Example 5: Phase 2, Prospective Open Label, Single Arm Study to Investigate Anti-Tumor Effect and Tolerability of 2X-121 in Patients with Advanced Ovarian Cancer Selected by the 2X-121 DRP®

The primary objective of this study was to evaluate the anti-tumor efficacy of 2X-121 (i.e., stenoparib) as single agent therapy at 600 mg daily as QD (once daily) regimen compared to BID (twice-a-day) regimen in advanced ovarian cancer patients selected by the 2X-121 DRP®.

Patient population: Histologically or cytologically documented epithelial ovarian carcinoma including high-grade serous, endometrioid, clear cell, carcinosarcoma, undifferentiated, and mixed histological subtypes (independent of BRCA1 and homologous recombination (HR) deficiency (HRD) status) and with 2 or more previous chemotherapies/antibody therapies including treatment with other PARPi for advanced, refractory, or recurrent ovarian cancer. Patients were selected with DRP-2×121-Ovary (also known as stenoparib-DRP®) using the genes listed in Table 1 and 2.

Results of First Interim Analysis:

22 patients were screened for BID dosing, and 23 patients had been screened for QD dosing, with 17 and 12 DRP-positive patients, respectively. Two patients consented but did not receive first dose and were not part of the Interim Analysis Population (IAP) or safety population. Table 5 below shows the baseline characteristics in the IAP.

TABLE 5

Baseline characteristics in the Interim Analysis Population in terms of BRCA mutation status and homologous recombination deficiency (HRD) status.

| | QD (N = 18) | BID (N = 10) |
|---|---|---|
| prior PARP treatment | | |
| Yes | 28% | 90% |
| No | 72% | 10% |
| tumor BRCA1/2 | | |
| Mut | 0% | 20% |
| WT | 28% | 0% |
| unknown | 72% | 80% |
| blood BRCA1/2 | | |
| Mut | 0% | 0% |
| WT | 33% | 70% |
| unknown | 67% | 30% |
| HRD status | | |
| positive | 0% | 20% |
| negative | 0% | 0% |
| unknown | 100% | 80% |

28 patients entered treatment: 11 from without DRP screening, 7 from QD (600 mg stenoparib daily) after DRP screening, and 10 from BID (200 mg stenoparib morning and 400 mg stenoparib evening) after DRP screening. The Interim Analysis Population (IAP) and safety population consisted of 28 patients (10 BID and 18 QD). Five patients received a first dose but dropped out before any tumor evaluation. Table 6 below shows the best overall tumor response in the IAP population.

TABLE 6

Tumor response (evaluated using RECIST 1.1)

| Tumor response | QD (N = 18 IAP) | BID (N = 10 IAP) |
|---|---|---|
| CR | 0 (0%) | 1 (10%) unconfirmed |
| PR | 0 (0%) | 0 (0%) |
| SD | 3 (17%) | 3 (30%) |

TABLE 6-continued

| Tumor response (evaluated using RECIST 1.1) | | |
|---|---|---|
| Tumor response | QD (N = 18 IAP) | BID (N = 10 IAP) |
| SD > 16w | 1 (6%) | 1 (10%) |
| PD | 9 (50%) | 0 (0%) |
| Not evaluated | 5 (28%) | 5 (50%) |

Table 7 below shows the CA125 response evaluated according to Gynecologic Cancer Intergroup (GCIG) guidelines. Only patients with a baseline of CA125 twice the upper normal limit of 70 unit/ml who received at least one dose were included in IAP. Only patients who had completed 2 cycles were determined to be evaluable for CA125 response. Two QD patients and four BID patients were below 70 units/ml. The CA125 test was confirmed with a second measurement that was lower than or within 10% of the previous measurement.

TABLE 7

| CA125 test response (GCIG) | | |
|---|---|---|
| CA125 response | QD (N = 16 IAP) | BID (N = 6 IAP) |
| CR | 0 (0%) | 1 (17%) unconfirmed |
| PR | 0 (0%) | 0 (0%) |
| SD | 3 (19%) | 1 (17%) |

Figure 4A:
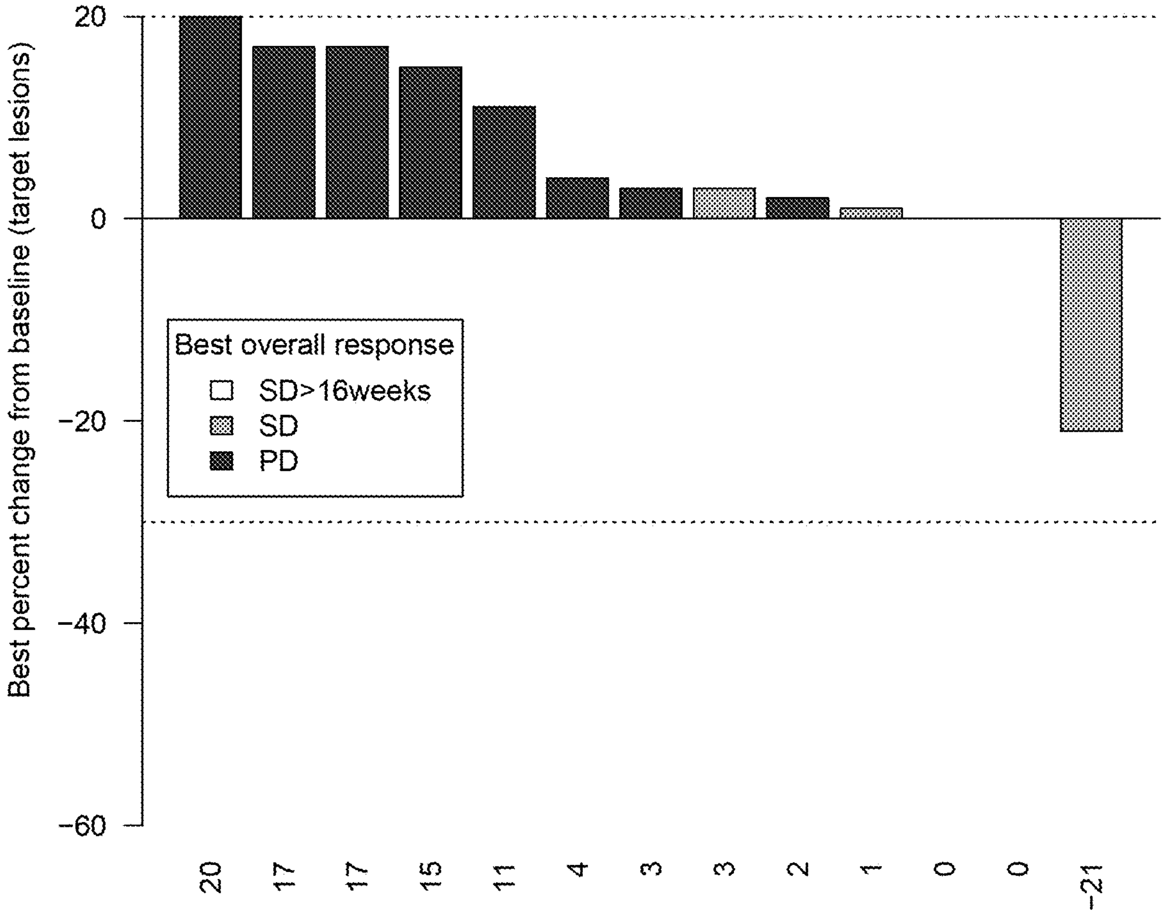
FIG. 4A and FIG. 4B are waterfall plots showing the best change in tumor diameter from baseline in the IAP QD population (FIG. 4A) and the IAP BID population (FIG. 4B). CR: complete response; SD: stable disease; PD: disease progression. Numerical values below each bar report the % change value of the corresponding bar. The CR is unconfirmed, and consists of target lymph node lesions that all turn normal. This CR patient also has CA125 CR unconfirmed.
Figure 4B:
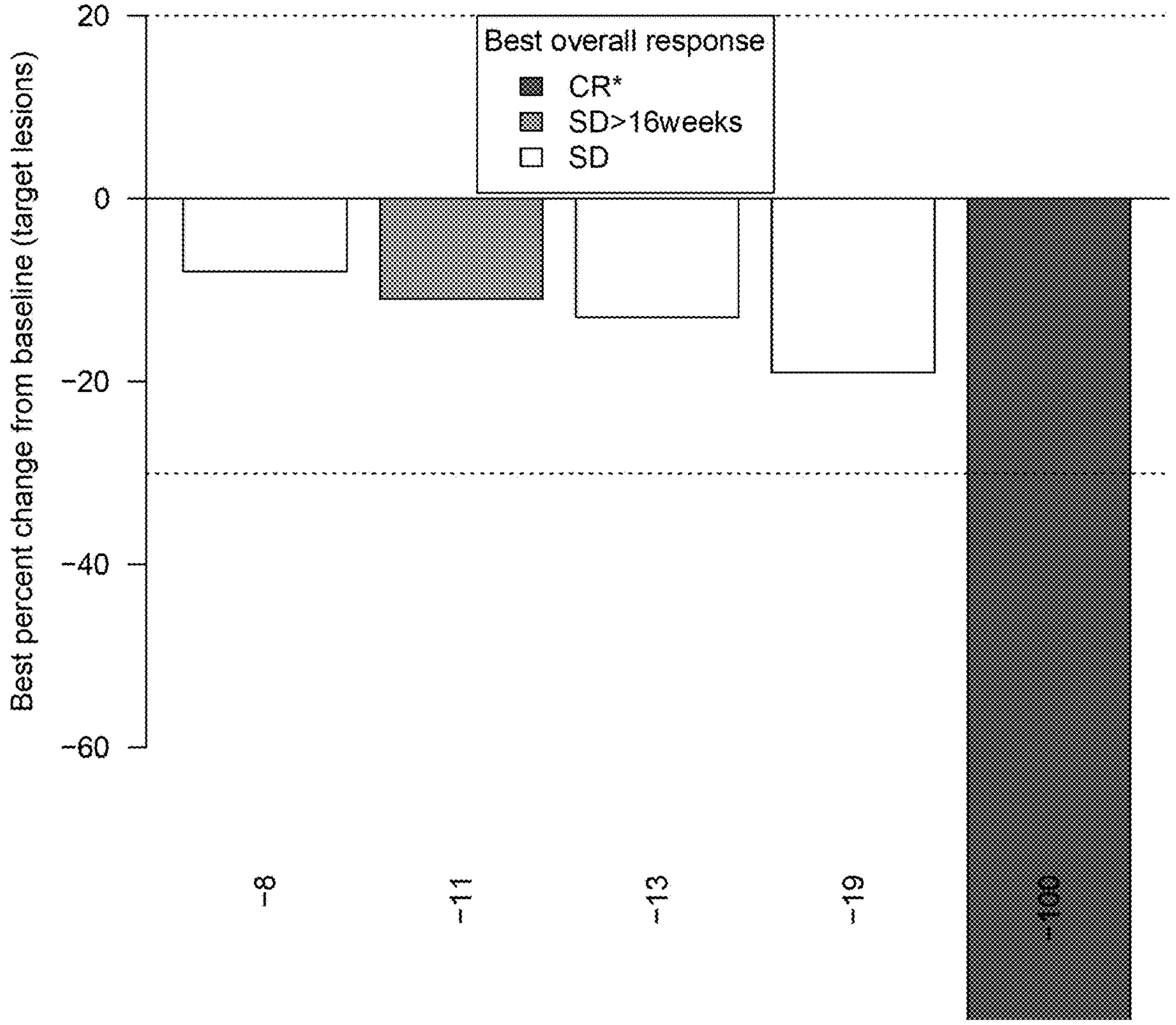
Figure 5:
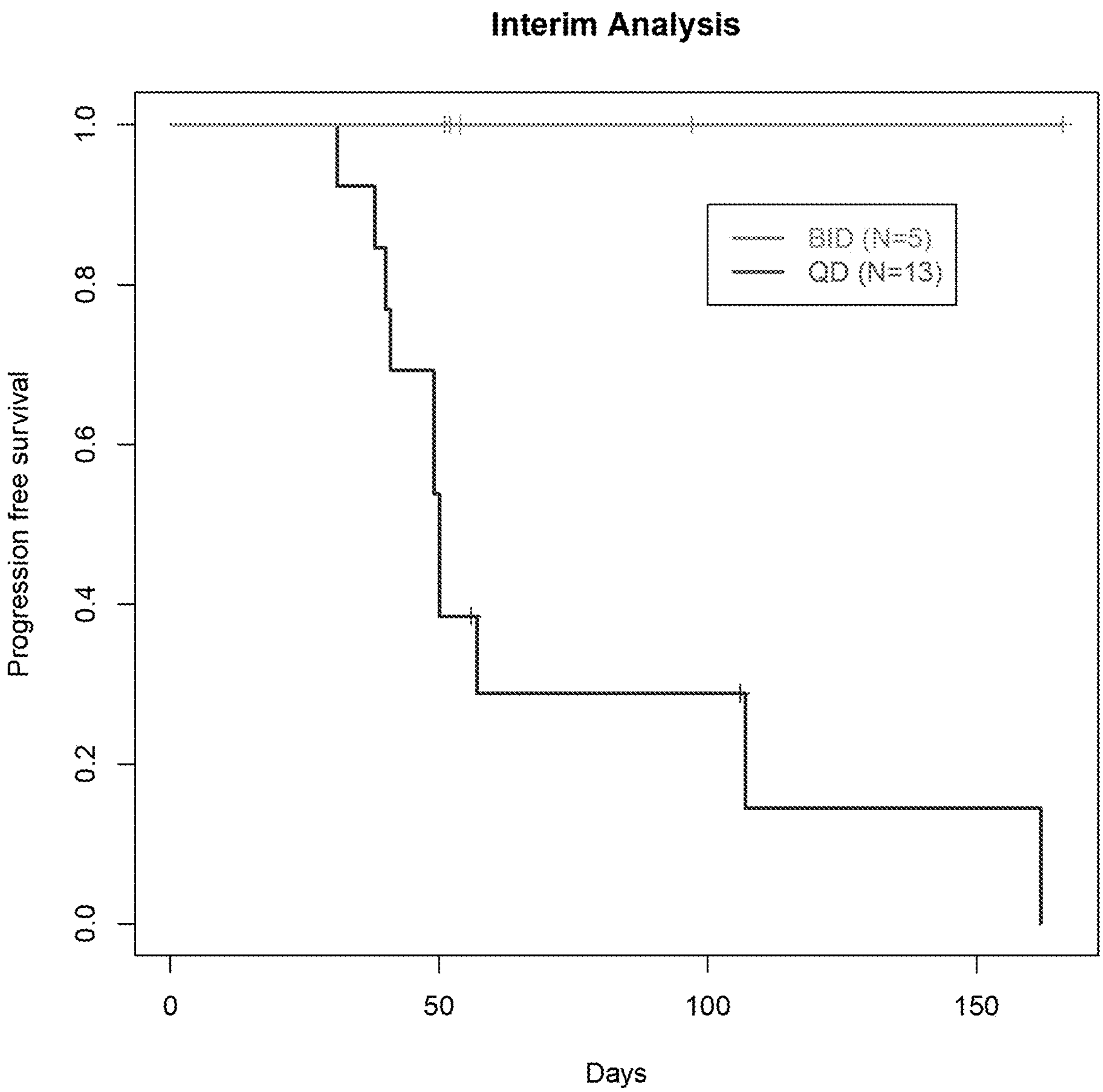
FIG. 5 is a Kaplan-Meier plot of progression-free survival in the IAP population stratified by stenoparib dosing: QD vs BID. Censored patients, for whom a date of progression or death has not yet been established, are indicated with a vertical line on each curve.

FIG. 4A and FIG. 4B show the best change in tumor diameter from baseline in the IAP QD population (FIG. 4A) and the IAP BID population (FIG. 4B). Progression free survival in the IAP population is shown in FIG. 5. The mean of best change in tumor diameter from baseline in the QD population (FIG. 4A) was 4% tumor growth. The CR in the BID pollution (FIG. 4B) was unconfirmed, and consisted of target lymph node lesions that all turned normal. This CR patient also had CA125 CR unconfirmed status. The mean of best change in tumor diameter from baseline in the BID population (FIG. 4B) was 29% tumor reduction. The median PFS was not reached in the BID population, and was 50 days (1.6 months) in the QD population.

Analysis of DRP Scores

DRP scores correlation to best change in tumor diameter was assessed for the three cohorts:

US QD (no DRP selection): CC=0.30

UK QD (DRP selection): Pearson CC=0.41

US BID (DRP selection): Pearson CC=−0.49

To demonstrate a correlation between a DRP score and a reduction in tumor diameter, the correlation must be negative. Only the BID population exhibited such a negative correlation. These surprising results demonstrated that stenoparib DRP was surprisingly effective at predicting effectiveness of stenoparib BID treatment in patients with ovarian cancer.

In order to calculate a correlation coefficient for DRP scores and the RECIST best response category, the RECIST response categories were numerically encoded as follows: complete response (CR)=1, partial response (PR)=2, stable disease (SD)>16w=3, SD=4, disease progression (PD)=5. The resulting CC was obtained for the three for the three cohorts:

DFCI QD (no DRP selection): Pearson CC=0.37

UK QD (DRP selection): Pearson CC=0.93

US BID (DRP selection): Pearson CC=−0.60

For a correlation between a DRP score and a clinically beneficial response, the correlation must be negative. Only BID has such a negative correlation. These surprising results likewise demonstrated that stenoparib DRP was surprisingly effective at predicting effectiveness of stenoparib BID treatment in patients with ovarian cancer.

Figure 6A:
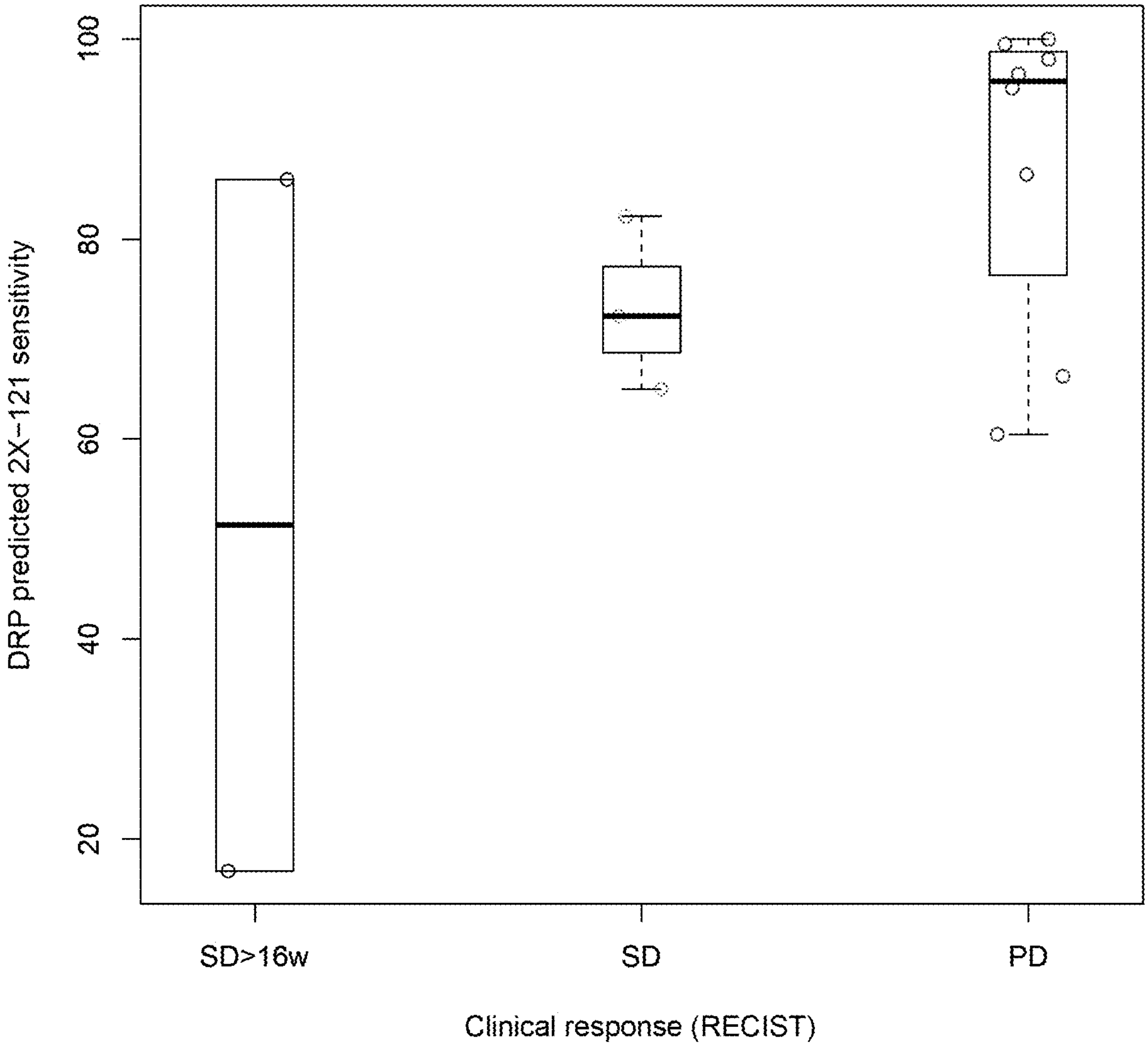
FIG. 6A and FIG. 6B are stripcharts of DRP scores in the individual RECIST categories.
Figure 6B:
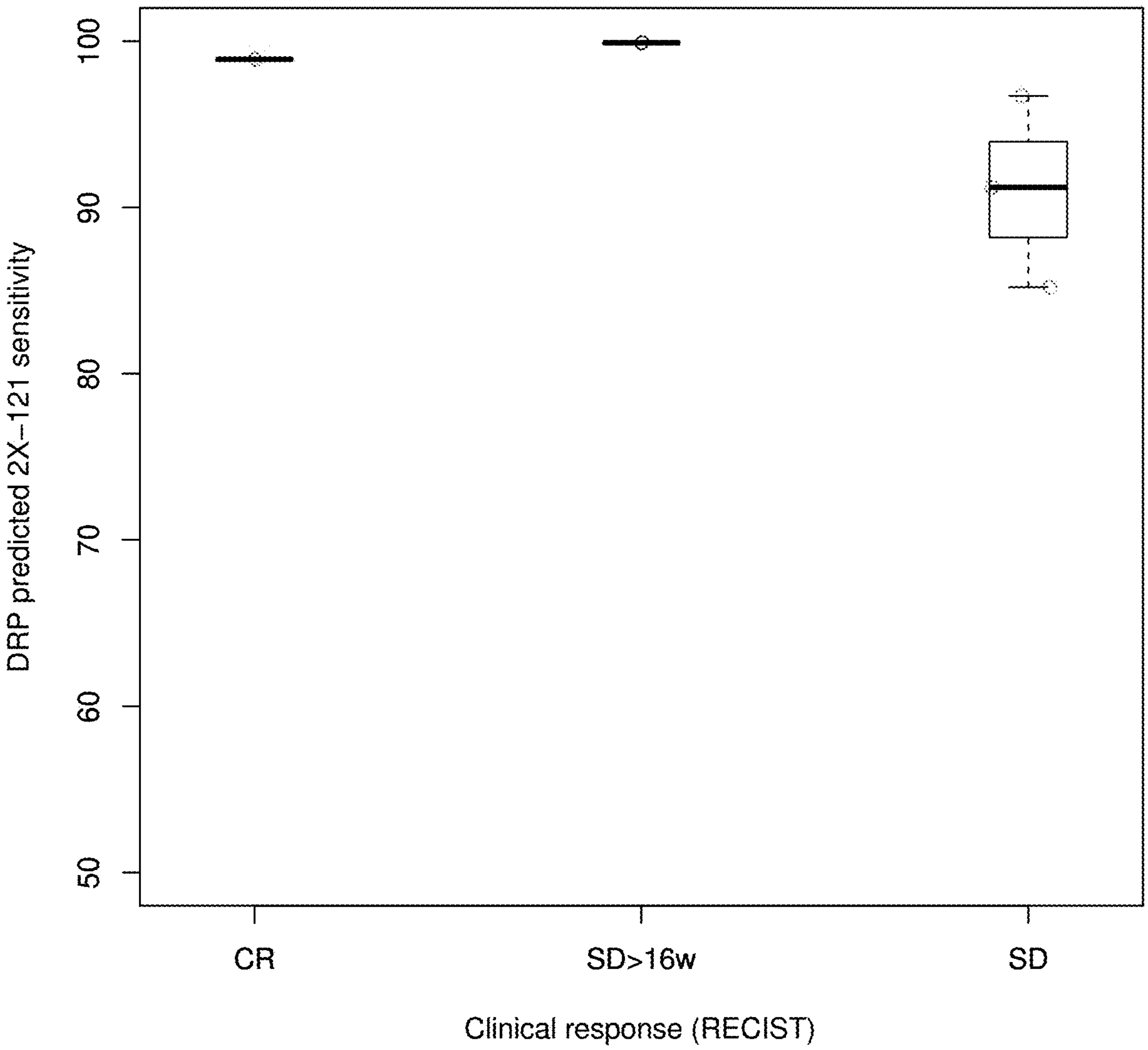

FIG. 6A and FIG. 6B show stripcharts of DRP scores in the individual RECIST categories. There was no apparent association between DRP score and RECIST category for QD dosed patients, as confirmed with a correlation analysis of QD scores. FIG. 6A shows a stripchart for QD dosed patients and FIG. 6B shows a stripchart for BID dosed patients. A correlation to RECIST category was found for BID dosed patients, as confirmed by the correlation analysis above. As is clear from the data, BID dosing was considerably more robust and effective than QD dosing.

Safety

Adverse events and treatment-related adverse events in the safety population (N=28) are listed in Table 8 and Table 9 below. There was a bias in this evaluation in that most BID patients had been in treatment for a shorter duration than the QD patients, and thus had a longer period of time to experience adverse events. The Adverse events listed for the QUADRA trial in the niraparib FDA approval were included for comparison (see Moore et al., Lancet Oncol. 20:636-648, 2019).

TABLE 8

| Adverse events in the safety population (N = 28) | | | |
|---|---|---|---|
| | Grade 1-4 | Grade 3-4 | Grade 5 |
| 600 mg QD (N = 18) | 100% | 61% | 6% |
| 600 mg BID (N = 10) | 70% | 20% | 0% |
| 300 mg QD niraparib (N = 463) | NA | NA | 2% |

TABLE 9

| Treatment-related adverse events | | | | | |
|---|---|---|---|---|---|
| | Grade 1 | Grade 2 | Grade 3 | Grade 4 | Grade 5 |
| 600 mg QD (N = 18) | 94% | 83% | 33% | 0% | 0% |
| 600 mg BID (N = 10) | 70% | 60% | 20% | 0% | 0% |
| 300 mg QD niraparib (N = 463) | 90% | | 56% | 20% | <1% |

Myelotoxicity that was observed for other PARP inhibitors (i.e., niraparib) is shown below in Table 10. In the published Phase I trial of 2X-121 (Plummer, *Br J Cancer* 2020. 123 (4): 525-533, 2020), there was no myelotoxicity among adverse events found in more than 5% of patients. Because myelotoxicity appeared to be a rare event for 2X-121, 14 patients with metastatic breast cancer that received 600 mg QD in a phase II trial were included in Table 10.

TABLE 10

| Myelotoxicity that was observed for other PARP inhibitors | | | | |
|---|---|---|---|---|
| | 2X-121 BID + QD (N = 42) | | Niraparib QD (N = 463) | |
| | Grade 1-4 | Grade 3-4 | Grade 1-4 | Grade 3-4 |
| Neutropenia | 2% | 0% | 20% | 13% |
| Anemia | 21% | 7% | 51% | 27% |
| Thrombocytopenia | 0% | 0% | 52% | 28% |

Dose modifications in patients with advanced ovarian cancer are shown and compared to niraparib in Table 11 below.

TABLE 11

| Dose modifications in patients with advanced ovarian cancer | | | |
|---|---|---|---|
| | Reduction | Interruption | Discontinuation |
| 600 mg QD (N = 18) | 28% | 83% | 11% |
| 600 mg BID (N = 9) | 40% | 50% | 0% |
| 300 mg QD niraparib (N = 463) | 47% | 62% | 21% |

CONCLUSION

BID dosing was more effective than QD dosing (FIG. 4A, FIG. 4B, and FIG. 5). Myelosuppression occurred less with 2X-121 (QD and BID) compared to approved PARP inhibitor niraparib. DRP scores showed correlation to clinical benefit in BID dosed patients, but not in QD dosed patients.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Although specific dosing regimens (e.g., including a pharmaceutical composition including stenoparib, or a pharmaceutically acceptable salt thereof, optionally with a pharmaceutical composition including dovitinib, or a pharmaceutically acceptable salt thereof) have been disclosed, a number of other embodiments and modifications may be made without departing from the spirit and scope of the invention. It should be apparent, however, to those skilled in the art that many more modifications besides those already described are possible without departing from the inventive concepts described herein. The inventive subject matter, therefore, is not to be restricted except in the spirit of the disclosure.

All patents, patent publications and publications mentioned herein are incorporated herein by reference in their entirety to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

Other embodiments are within the claims.

The invention claimed is:

1. A method of treating a cancer in a subject in need thereof comprising administering to the subject a dosing regimen comprising a first dose and a second dose of a composition comprising stenoparib or a pharmaceutically acceptable salt thereof or a hydrate thereof per day.

2. The method of claim 1, wherein:

(a) the dosing regimen comprises 2-100 dosing cycles;

(b) an amount of stenoparib or the pharmaceutically acceptable salt thereof or the hydrate thereof administered in the first dose is less than or equal to an amount of stenoparib or the pharmaceutically acceptable salt thereof or the hydrate thereof administered in the second dose;

(c) the first dose comprises between about 200 mg to about 400 mg of stenoparib or the pharmaceutically acceptable salt thereof or the hydrate thereof; and/or (d) the second dose comprises between about 400 mg to about 600 mg of stenoparib or the pharmaceutically acceptable salt thereof or the hydrate thereof.

3. The method of claim 2, wherein the dosing regimen comprises 2 to 8 dosing cycles.

4. The method of claim 1, wherein:

(i) the first dose comprises about 400 mg of stenoparib or the pharmaceutically acceptable salt thereof or the hydrate thereof and the second dose comprises about 400 mg of stenoparib or the pharmaceutically acceptable salt thereof or the hydrate thereof; or (ii) the first dose comprises about 400 mg of stenoparib or the pharmaceutically acceptable salt thereof or the hydrate thereof and the second dose comprises about 600 mg of stenoparib or the pharmaceutically acceptable salt thereof or the hydrate thereof.

5. The method of claim 1, wherein:

(a) the cancer:

(i) is a solid tumor cancer;

(ii) is locally advanced or metastatic;

(iii) comprises a BRCA mutation; and/or (iv) is homologous recombination (HR) deficient; and/or (b) the subject is non-responsive to at least one cancer therapy other than stenoparib or a pharmaceutically acceptable salt thereof or a hydrate thereof.

6. The method of claim 5, wherein the cancer is a solid tumor cancer, and wherein the cancer is an ovarian cancer, a breast cancer, a colon cancer, a pancreatic cancer, or a prostate cancer.

7. The method of claim 6, wherein the cancer is ovarian cancer, and wherein the ovarian cancer is an epithelial ovarian carcinoma.

8. The method of claim 7, wherein the epithelial ovarian carcinoma is a high-grade serous epithelial ovarian carcinoma, an endometrioid epithelial ovarian carcinoma, a clear cell epithelial ovarian carcinoma, an epithelial ovarian carcinosarcoma, an undifferentiated epithelial ovarian carcinoma, or an epithelial ovarian carcinoma of mixed histological subtypes.

9. The method of claim 1, wherein the subject is non-responsive to at least one cancer therapy other than stenoparib or a pharmaceutically acceptable salt thereof or a hydrate thereof, and wherein the at least one cancer therapy comprises a PARP inhibitor.

10. The method of claim 1, wherein the composition is formulated as a capsule or a tablet.

11. The method of claim 10, wherein the composition is formulated as a capsule, and wherein each capsule comprises about 50 mg, about 100 mg, or about 200 mg of stenoparib or the pharmaceutically acceptable salt thereof or the hydrate thereof.

12. The method of claim 1, wherein the method comprises, prior to administration of the composition, determining the responsiveness of the subject to treatment with stenoparib or the pharmaceutically acceptable salt thereof or the hydrate thereof by:

(a) determining the expression level of one or more biomarkers of sensitivity selected from the group consisting of SRSF7, UCHL1, MLLT11, ADD2, PRMT1, SRSF3, PRMT5, COCH, RUVBL1, MARCKSL1, CHERP, MTSS1, LSM4, RAPGEF5, PRPF4, DESI2, RNPS1, SNX10, CUL3, CHD4, MSH2, HNRNPM, SRSF1, NELL2, PAICS, HOXA10, BUB1B, E2F5, MAGED4/MAGED4B/SNORA11D/SNORA11E, PRPF8, SORD, HNRNPU, PEX5, HYPK/MIR1282/SERF2/SERF2-C15ORF63, STRAP, NDUFAB1, FARSA, STOML2, ERH, HSBP1, DDX39A, ODC1, TAF5, TBC1D31, TRA2B, NUDC, DDX23, PRPF31, UBE2S, TCF4, MLF2, CCDCl81, RPF1, PASK, NUP88, RNASEH2A, FBL, LOC101928747/RBMX/SNORD61, NXF1, PLEKHO1, GAR1, RPA1, ZNF24, BOP1 MIR7112, RAB3B, SLC35G2, DKC1/MIR664B/SNORA56, PSMC3IP, DNAJC7, RRP1B, NME1, SNRPA, DBN1, KIAA0020, SUPV3L1, ZNF573, FAM134B, TOX3, HSPD1, ACLY, MSANTD3-TMEFF1/TMEFF1, AKIRIN1, UBE2M, MTF2, EWSR1, SKP2, TMEM97, HNRNPD, ILKAP, NASP, SNRPD1, TIMM44, PKN1, STAU2, DNAAF2, SNRPD2, FUS, ATP6V1G2-DDX39B/DDX39B/SNORD84, PDSS1, TPGS2, SLIRP, NCL, ANP32A, SAFB, STIP1, CEP68, C8orf33, MRPL11, POLR21, MCAM/MIR6756, ECSIT MDK, PUF60, PFN2, SYNCRIP, TSPAN3, SLC16A1, POLR2H, MAP3K7, CSRP2, BCL11A, PNKP, DNAJC6, FDFT1, FADS1/MIR1908, RPARP-AS1, DHRS7, CCNB1IP1, CCT3/LOC101927137, DDX18, AARSD1/PTGES3L/PTGES3L-AARSD1, HNRNPDL, ATXN7L3B, MRPS14, SOX4, ELOVL2, KCNJ8, TRIAP1, EIF2B1, FBXL14, MAPRE2, ORC4, MDN1, KNOP1, KBTBD11, FADS2, RANBP1, PLEKHB1, HSPE1, ITFG2/LOC100507424, SFPQ, RFC3, SDR39U1, PBK, PHB, KHDRBS1, PDAP1, SSRP1, and B3GALT2; and/or (b) determining the expression level of one or more biomarkers of resistance selected from the group consisting of HLA-E, GADD45B, CLIC1, LASP1, APOBEC3B, LGALS1, TAPBP, AHNAK, BHLHE40, S100A11, LITAF, ZBTB38, TCIRG1, S100A11P1, CTSA, FXYD5, YPEL5, HLA-C, STOM, PLIN3, IRF1, LMNA, NPC2, P4HB, KLF6, RHOC, SRGN, STAT1, PIEZO1, LGALS3, CD97, HLA-B, FNDC3B/LOC101928615, CKLF/CKLF-CMTM1, IFI35, TIPARP, TAP1, MICALL2, RRBP1, ZFP36, TNIP1, CD59, LDLRAP1, FLNB, PSG6, CBX7, RARRES3, CFLAR, SUN2, EHD2, MAP3K5, NOL12/TRIOBP, ARPC1B, TNFSF10, HLA-G, RP11-395B7.7, LEPROT, BTN3A2/BTN3A3, INPP4B, DUSP1, EVI2A, EHD1, EPAS1, IQGAP1, CLIC3, NACC2, TGFBI, IER3, MICA, CNN2, VEGFA, MBNL1, ISG15, TNFAIP8, COPG1, PSMB9, ZFP36L1, IL6ST, SHC1, GSTK1, CAV1, KRT7, TFPI, RHOG, CDH11, ABCC3, HLA-J, MYL12A, MRPS10, RRAS, TMEM2, SIDT2, RAB11FIP1, RTP4, SPTBN1, TMEM189/TMEM189-UBE2V1/UBE2V1/UBE2V2, ITGA5, CDC42EP1, OSER1, CHST15, MDFIC, CAV2, CARD10, RAC2, MLPH, F2R, ICAM3, CRIM1/LOC101929500, EVI2B, PFKFB3, MIR6513/TMBIM1, APOL3, CD55, TRAM2, S100A4, PIP4K2A, RPN2, IFIT3, PLAC8, SDF4, MVP, RNH1, EIF1, SERPINB1, ASL, CD99, USP4, TACC1, PDXK, BST2, LOC101928916/NNMT, DUSP5, COMT, LY6E, ACSL5, GBP2, TNFRSF1B, PTRF, CYR61, BTN3A1, PLEC, CTNND1/TMX2-CTNND1, TNFRSF14, ABCC10, SELPLG, GPX4, EDEM1, MIR6787/SLC16A3, DMBT1, PSMB8, COL1A1, FOS, CYLD, ADAMTS1, ALDOA, GATA6, YWHAB, CIB1, OPTN, IFI16, PTGER4, CCND1, PDLIM5, HLA-F, CYP1B1, SVIL, TAGLN2, IFI27, FLII, STAT6, WWP2, FLNC, PARP12, VPS13D, IFITM2, CTSZ, C19orf10, DAPK1, LOC101928189/RSRP1, MYOF, ATP2B4, AXL, LY96, FN1, CREB3L1, TNFSF12-TNFSF13/TNFSF13, POFUT2, WDR1, SLC7A7, MICB, GATA3, LRRFIP1, RNASET2, and ITM2A.

13. A method of treating a cancer in a subject in need thereof comprising administering to the subject a dosing regimen comprising:

(a) administering a first dose and a second dose of a first composition comprising stenoparib or a pharmaceutically acceptable salt thereof or a hydrate thereof per day; and (b) administering a dose of a second composition comprising dovitinib or a pharmaceutically acceptable salt thereof or a hydrate thereof.

14. The method of claim 13, wherein:

(i) the dosing regimen comprises 2-100 dosing cycles;

(ii) the method comprises administering the first and second doses of the first composition each day of the dosing cycle and administering the second composition on a 5 days on/2 days off schedule during the dosing cycle;

(iii) an amount of stenoparib or the pharmaceutically acceptable salt thereof or the hydrate thereof administered in the first dose of the first composition is less than or equal to an amount of stenoparib or the pharmaceutically acceptable salt thereof or the hydrate thereof administered in the second dose of the first composition;

(iv) the first dose of the first composition comprises between about 200 mg to about 400 mg of stenoparib or the pharmaceutically acceptable salt thereof or the hydrate thereof;

(v) the second dose of the first composition comprises between about 400 mg to about 600 mg of stenoparib or the pharmaceutically acceptable salt thereof or the hydrate thereof; and/or (vi) the dose of the second composition comprises between about 300 mg to about 500 mg of dovitinib or the pharmaceutically acceptable salt thereof or the hydrate thereof.

15. The method of claim 14, wherein the dosing regimen comprises 2-8 dosing cycles.

16. The method of claim 13, wherein:

(A)

(a) the first dose of the first composition comprises about 400 mg of stenoparib or the pharmaceutically acceptable salt thereof or the hydrate thereof and the second dose of the first composition comprises about 400 mg of stenoparib or the pharmaceutically acceptable salt thereof or the hydrate thereof; or (b) the first dose of the first composition comprises about 400 mg of stenoparib or the pharmaceutically acceptable salt thereof or the hydrate thereof and the second dose of the first composition comprises about 600 mg of stenoparib or the pharmaceutically acceptable salt thereof or the hydrate thereof; and/or (B)

(a) the dose of the second composition comprises about 300 mg of dovitinib or the pharmaceutically acceptable salt thereof or the hydrate thereof;

(b) the dose of the second composition comprises about 400 mg of dovitinib or the pharmaceutically acceptable salt thereof or the hydrate thereof; or (c) the dose of the second composition comprises about 500 mg of dovitinib or the pharmaceutically acceptable salt thereof or the hydrate thereof.

17. The method claim 13, wherein the cancer:

(a) is a solid tumor cancer;

(b) is locally advanced or metastatic;

(c) comprises a BRCA mutation; and/or (d) is homologous recombination (HR) deficient.

18. The method of claim 13, wherein the cancer is a solid tumor cancer, and wherein the cancer is an ovarian cancer, a breast cancer, a colon cancer, a pancreatic cancer, or a prostate cancer.

19. The method of claim 13, wherein the first composition is formulated as a capsule or a tablet and/or the second composition is formulated as a tablet.

20. The method of claim 19, wherein:

(a) the first composition is formulated as a capsule, and wherein each capsule of the first composition comprises about 50 mg, about 100 mg, or about 200 mg of stenoparib or the pharmaceutically acceptable salt thereof or the hydrate thereof; and/or (b) the second composition is formulated as a tablet, and wherein each tablet of the second composition comprises about 100 mg of dovitinib or the pharmaceutically acceptable salt thereof or the hydrate thereof.

21. The method of claim 13, wherein the method comprises, prior to the administration of the first and second compositions:

(I) determining the responsiveness of the subject to treatment with stenoparib or a pharmaceutically acceptable salt thereof or a hydrate thereof by:

(a) determining the expression level of one or more biomarkers of sensitivity selected from the group consisting of SRSF7, UCHL1, MLLT11, ADD2, PRMT1, SRSF3, PRMT5, COCH, RUVBL1, MARCKSL1, CHERP, MTSS1, LSM4, RAPGEF5, PRPF4, DESI2, RNPS1, SNX10, CUL3, CHD4, MSH2, HNRNPM, SRSF1, NELL2, PAICS, HOXA10, BUB1B, E2F5, MAGED4/MAGED4B/SNORA11D/SNORA11E, PRPF8, SORD, HNRNPU, PEX5, HYPK/MIR1282/SERF2/SERF2-C15ORF63, STRAP, NDUFAB1, FARSA, STOML2, ERH, HSBP1, DDX39A, ODC1, TAF5, TBC1D31, TRA2B, NUDC, DDX23, PRPF31, UBE2S, TCF4, MLF2, CCDC181, RPF1, PASK, NUP88, RNASEH2A, FBL, LOC101928747/RBMX/SNORD61, NXF1, PLEKHO1, GAR1, RPA1, ZNF24, BOP1 MIR7112, RAB3B, SLC35G2, DKC1/MIR664B/SNORA56, PSMC3IP, DNAJC7, RRP1B, NME1, SNRPA, DBN1, KIAA0020, SUPV3L1, ZNF573, FAM134B, TOX3, HSPD1, ACLY, MSANTD3-TMEFF1/TMEFF1, AKIRIN1, UBE2M, MTF2, EWSR1, SKP2, TMEM97, HNRNPD, ILKAP, NASP, SNRPD1, TIMM44, PKN1, STAU2, DNAAF2, SNRPD2, FUS, ATP6V1G2-DDX39B/DDX39B/SNORD84, PDSS1, TPGS2, SLIRP, NCL, ANP32A, SAFB, STIP1, CEP68, C8orf33, MRPL11, POLR21, MCAM/MIR6756, ECSIT, MDK, PUF60, PFN2, SYNCRIP, TSPAN3, SLC16A1, POLR2H, MAP3K7, CSRP2, BCL11A, PNKP, DNAJC6, FDFT1, FADS1/MIR1908, RPARP-AS1, DHRS7, CCNB1IP1, CCT3/LOC101927137, DDX18, AARSD1/PTGES3L/PTGES3L-AARSD1, HNRNPDL, ATXN7L3B, MRPS14, SOX4, ELOVL2, KCNJ8, TRIAP1, EIF2B1, FBXL14, MAPRE2, ORC4, MDN1, KNOP1, KBTBD11, FADS2, RANBP1, PLEKHB1, HSPE1, ITFG2/LOC100507424, SFPQ, RFC3, SDR39U1, PBK, PHB, KHDRBS1, PDAP1, SSRP1, and B3GALT2; and/or (b) determining the expression level of one or more biomarkers of resistance selected from the group consisting of HLA-E, GADD45B, CLIC1, LASP1, APOBEC3B, LGALS1, TAPBP, AHNAK, BHLHE40, S100A11, LITAF, ZBTB38, TCIRG1, S100A11P1, CTSA, FXYD5, YPEL5, HLA-C, STOM, PLIN3, IRF1, LMNA, NPC2, P4HB, KLF6, RHOC, SRGN, STAT1, PIEZO1, LGALS3, CD97, HLA-B, FNDC3B/LOC101928615, CKLF/CKLF-CMTM1, IFI35, TIPARP, TAP1, MICALL2, RRBP1, ZFP36, TNIP1, CD59, LDLRAP1, FLNB, PSG6, CBX7, RARRES3, CFLAR, SUN2, EHD2, MAP3K5, NOL12/TRIOBP, ARPC1B, TNFSF10, HLA-G, RP11-395B7.7, LEPROT, BTN3A2/BTN3A3, INPP4B, DUSP1, EVI2A, EHD1, EPAS1, IQGAP1, CLIC3, NACC2, TGFBI, IER3, MICA, CNN2, VEGFA, MBNL1, ISG15, TNFAIP8, COPG1, PSMB9, ZFP36L1, IL6ST, SHC1, GSTK1, CAV1, KRT7, TFPI, RHOG, CDH11, ABCC3, HLA-J, MYL12A, MRPS10, RRAS, TMEM2, SIDT2, RAB11FIP1, RTP4, SPTBN1, TMEM189/TMEM189-UBE2V1/UBE2V1/UBE2V2, ITGA5, CDC42EP1, OSER1, CHST15, MDFIC, CAV2, CARD10, RAC2, MLPH, F2R, ICAM3, CRIM1/LOC101929500, EVI2B, PFKFB3, MIR6513/TMBIM1, APOL3, CD55, TRAM2, S100A4, PIP4K2A, RPN2, IFIT3, PLAC8, SDF4, MVP, RNH1, EIF1, SERPINB1, ASL, CD99, USP4, TACC1, PDXK, BST2, LOC101928916/NNMT, DUSP5, COMT, LY6E, ACSL5, GBP2, TNFRSF1B, PTRF, CYR61, BTN3A1, PLEC, CTNND1/TMX2-CTNND1, TNFRSF14, ABCC10, SELPLG, GPX4, EDEM1, MIR6787/SLC16A3, DMBT1, PSMB8, COL1A1, FOS, CYLD, ADAMTS1, ALDOA, GATA6, YWHAB, CIB1, OPTN, IFI16, PTGER4, CCND1, PDLIM5, HLA-F, CYP1B1, SVIL, TAGLN2, IFI27, FLIL, STAT6, WWP2, FLNC, PARP12, VPS13D, IFITM2, CTSZ, C19orf10, DAPK1, LOC101928189/RSRP1, MYOF, ATP2B4, AXL, LY96, FN1, CREB3L1, TNFSF12-TNFSF13/TNFSF13, POFUT2, WDR1, SLC7A7, MICB, GATA3, LRRFIP1, RNASET2, and ITM2A; and/or (II) determining the responsiveness of the subject to treatment with dovitinib or a pharmaceutically acceptable salt thereof or a hydrate thereof by:

(a) determining the expression level of one or more biomarkers of sensitivity selected from the group consisting of DDIT4, ZNF395, lncRNA, LSM4, SEL1L3, FABP5, TRIM22, TPK1, SLC16A3, INSIG1, HOXA10-HOXA9/HOXA9/MIR196B, DPP4, LDLR, HSPE1, VEGFA, TMSB10, CAV2, P4HA1, APOL1, PTPRE, DPYSL2, ANP32B, STAT6, RPL27A/SNORA3, EPB41L2, RPL38, and RNU86/RPL3/SNORD83B; and/or (b) determining the expression level of one or more biomarkers of resistance selected from the group consisting of SCAMP3, BAG5, ABCF1, 46087, EMC3, UCP2, TUG1, CLPTM1, IGFBP5, MAGEA1, ATM, GATA3, SPDEF, LDOC1, HRAS, SRM, ZNF331, TOB1, APITD1/CORT, NDUFV1, BAG6, CUL3, CCDC90A, CERS2, LOC100506032/NBPF10/NBPF11/NBPF12/NBPF15/NBPF16/NBPF24/NBPF7/NBPF8/NBPF9, PPP1R11, and CKB.

22. The method of claim 1, wherein the dosing regimen comprises a dosing cycle comprising administration of the composition for 28 days±1 to 5 days.

23. The method of claim 1, wherein the second dose is administered to the subject at least 11 to 13 hours after administration of the first dose.

24. The method of claim 1, wherein the first dose comprises about 200 mg of stenoparib or the pharmaceutically acceptable salt thereof or the hydrate thereof and the second dose comprises about 400 mg of stenoparib or the pharmaceutically acceptable salt thereof or the hydrate thereof.

25. The method of claim 1, wherein the first dose comprises about 300 mg of stenoparib or the pharmaceutically acceptable salt thereof or the hydrate thereof and the second dose comprises about 300 mg of stenoparib or the pharmaceutically acceptable salt thereof or the hydrate thereof.

26. The method of claim 1, wherein the cancer is advanced ovarian cancer.

27. The method of claim 1, wherein the subject is administered the composition orally.

28. The method of claim 1, wherein:

(a) the dosing regimen comprises 2-8 dosing cycles, each comprising administration of the composition for 28 days±1 to 5 days;

(b) the second dose is administered to the subject at least 11 to 13 hours after administration of the first dose;

(c) the first dose comprises about 200 mg of stenoparib or the pharmaceutically acceptable salt thereof or the hydrate thereof and the second dose comprises about 400 mg of stenoparib or the pharmaceutically acceptable salt thereof or the hydrate thereof;

(d) the cancer is advanced ovarian cancer; and (e) the subject is administered the composition orally.

29. The method of claim 13, wherein the dosing regimen comprises a dosing cycle comprising 28 days±1 to 5 days.

30. The method of claim 13, wherein the second dose is administered to the subject at least 11 to 13 hours after administration of the first dose.

31. The method of claim 29, wherein the dosing regimen comprises 28 days, and wherein the second composition is administered to the subject as a single dose on Days 1-5, Days 8-12, Days 15-19, and Days 22-26 of each said dosing cycle.

32. The method of claim 13, wherein (A) the first dose of the first composition comprises about 200 mg of stenoparib or the pharmaceutically acceptable salt thereof or the hydrate thereof and the second dose of the first composition comprises about 400 mg of stenoparib or the pharmaceutically acceptable salt thereof or the hydrate thereof; and (B)

(a) the dose of the second composition comprises about 300 mg of dovitinib or the pharmaceutically acceptable salt thereof or the hydrate thereof;

(b) the dose of the second composition comprises about 400 mg of dovitinib or the pharmaceutically acceptable salt thereof or the hydrate thereof; or (c) the dose of the second composition comprises about 500 mg of dovitinib or the pharmaceutically acceptable salt thereof or the hydrate thereof.

33. The method of claim 13, wherein:

(A) the first dose of the first composition comprises about 300 mg of stenoparib or the pharmaceutically acceptable salt thereof or the hydrate thereof and the second dose of the first composition comprises about 300 mg of stenoparib or the pharmaceutically acceptable salt thereof or the hydrate thereof; and (B)

(a) the dose of the second composition comprises about 300 mg of dovitinib or the pharmaceutically acceptable salt thereof or the hydrate thereof;

(b) the dose of the second composition comprises about 400 mg of dovitinib or the pharmaceutically acceptable salt thereof or the hydrate thereof; or (c) the dose of the second composition comprises about 500 mg of dovitinib or the pharmaceutically acceptable salt thereof or the hydrate thereof.

34. The method claim 13, wherein the cancer is advanced ovarian cancer.

35. The method of claim 13, wherein the subject is administered the first composition orally and/or the subject is administered the second composition orally.

36. The method of claim 13, wherein:

(a) the dosing regimen comprises 2-8 28-day dosing cycles, wherein the second composition is administered to the subject as a single dose on Days 1-5, Days 8-12, Days 15-19, and Days 22-26 of each said dosing cycle;

(b) the second dose is administered to the subject at least 11 to 13 hours after administration of the first dose;

(c) the first dose comprises about 200 mg of stenoparib or the pharmaceutically acceptable salt thereof or the hydrate thereof and the second dose comprises about 400 mg of stenoparib or the pharmaceutically acceptable salt thereof or the hydrate thereof;

(d) the dose of the second composition comprises about 300, 400, or 500 mg of dovitinib or the pharmaceutically acceptable salt thereof or the hydrate thereof (d) the cancer is a solid tumor cancer; and (e) the subject is administered the first and second compositions orally.

* * * * *